# (12) United States Patent
Ono et al.

(10) Patent No.: US 7,888,123 B2
(45) Date of Patent: *Feb. 15, 2011

(54) METHOD FOR INTRODUCING A GENE INTO LABYRINTHULOMYCOTA

(75) Inventors: Kazuhisa Ono, Higashi-Hiroshima (JP);
Tsunehiro Aki, Higashi-Hiroshima (JP);
Seiji Kawamoto, Higashi-Hiroshima (JP)

(73) Assignee: Fujifilm Corporation, Tokyo (JP)

( * ) Notice: Subject to any disclaimer, the term of this patent is extended or adjusted under 35 U.S.C. 154(b) by 379 days.

This patent is subject to a terminal disclaimer.

(21) Appl. No.: 11/413,173

(22) Filed: Apr. 28, 2006

(65) Prior Publication Data

US 2006/0275904 A1 Dec. 7, 2006

(30) Foreign Application Priority Data

Apr. 28, 2005 (JP) ............................. 2005-131443

(51) Int. Cl.
*C12N 15/74* (2006.01)
*C12P 21/06* (2006.01)
*C12N 5/02* (2006.01)
*C07H 21/04* (2006.01)

(52) U.S. Cl. .................... 435/471; 435/134; 435/320.1; 435/476; 435/252.3; 536/23.1; 536/24.1; 536/24.2; 536/23.5

(58) Field of Classification Search ........................ None
See application file for complete search history.

(56) References Cited

U.S. PATENT DOCUMENTS

| 6,706,507 B2 | 3/2004 | Kudoh et al. |
| 2003/0166207 A1* | 9/2003 | Roessler et al. ............. 435/193 |
| 2006/0137043 A1 | 6/2006 | Puzio et al. |

FOREIGN PATENT DOCUMENTS

| JP | 9-284 A | 1/1997 |
| JP | 2003-189846 A | 7/2003 |
| JP | 2004-173695 | 6/2004 |
| JP | 2005-503125 A | 2/2005 |
| JP | 2005-102680 A | 4/2005 |
| WO | WO 98/07873 | 2/1998 |
| WO | WO 02/083869 A2 | 10/2002 |
| WO | WO 2004/052228 A2 | 6/2004 |
| WO | WO 2004/058956 A1 | 7/2004 |

OTHER PUBLICATIONS

Miblitz et al. In Targeted integration into a rRNA locus results in uniform and high level expression of transgenes in *Leishmania amastigotes* (Molecular and Biochemical Parasitology, vol. 107 , 2000, pp. 251-261).*
Score Report us-11-413-173.rge, Result 3, Jianzhong,H. and Xianzhang,J.,Submitted (Sep. 22, 2004) College of Bioengineering, Fujian Normal University, 172# Chengpu Road, Cangshan District, Fuzhou, Fujian 350007, China *Schizochytrium* FJU-512 gene for 18S rRNA.*
Avisory Action issued Apr. 9, 2009, in co-pending U.S. Appl. No. 11/413,141.
Final Office Action issued Dec. 10, 2008, in co-pending U.S. Appl. No. 11/413,141.
Non-final Office Action issued Jul. 23, 2009, in co-pending U.S. Appl. No. 11/413,141.
Non-final Office Action issued Mar. 18, 2008, in co-pending U.S. Appl. No. 11/413,141.
Notice of Allowance issued Feb. 26, 2010, in co-pending U.S. Appl. No. 11/413,141.
Berkamp RJ et al., "Multiple-copy integration of the alpha-galactosidase gene from Cyamopsis tetragonoloba into the ribosomal DNA of Kluyveromyces lactis," Curr Genet, Apr. 1992, vol. 21, No. 4-5, pp. 365-370.
Japanese Office Action issued Oct. 26, 2010, with regard to corresponding Japanese Patent Application JP2005-131443, with English translation.
Le Dall MT et al., "Multiple-copy integration in the yeast Yarrowia lipolytica," Curr Genet, Jul. 1994, vol. 26, No. 1, pp. 38-44.
Lopes TS et al., "High-copy-number integration into the ribosomal DNA of *Saccharomyces cerevisiae*: a new vector for high-level expression," Gene, Jul. 15, 1989, vol. 79, No. 2, pp. 199-206.

* cited by examiner

*Primary Examiner*—Nancy Vogel
*Assistant Examiner*—Catherine Hibbert
(74) *Attorney, Agent, or Firm*—Birch, Stewart, Kolasch & Birch, LLP.

(57) ABSTRACT

An object of the present invention is to provide a transformation system for Labyrinthulomycota that allows the elucidation of biosynthetic mechanisms of lipids such as PUFA and carotenoids as well as for the construction of a high production system and the design and development of novel functional lipid molecules by the control of the mechanisms. The present invention provides a method for introducing a transgene into a cell of Labyrinthulomycota, which comprises introducing into a cell of Labyrinthulomycota a recombinant vector comprising a transgene and a nucleotide sequence which is homologous to a part of chromosomal DNA of Labyrinthulomycota and is capable of homologous recombination with the chromosomal DNA, and then inducing homologous recombination in this homologous nucleotide sequence.

5 Claims, 17 Drawing Sheets

Fig.3

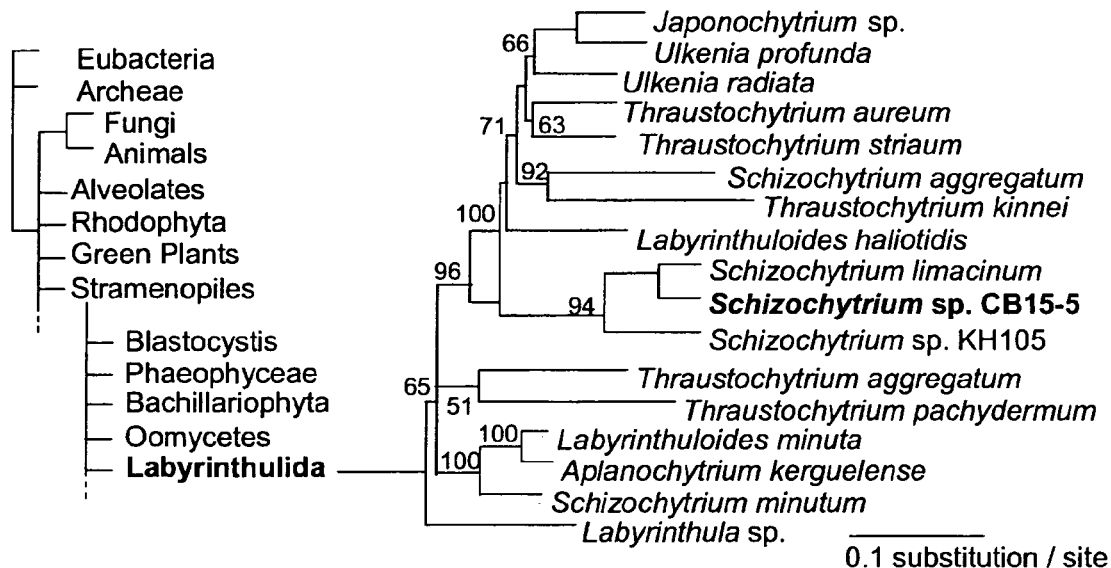

Fig.4

```
                     1         10        20        30        40        50        60        70        80
                     |---------+---------+---------+---------+---------+---------+---------+---------|
     Schizochytrium  MADDEVQALVIDNGSGMCKAGFAGDDAPRAVFPSIVGRPKHPGIMVGMDQKDAYVGDEAQSKRGVLTLKYPIEHGIVTNW
     phytophathora   MADEDVQALVVDNGSGMCKAGFAGDDAPRAVFPSIVGRPKHLGIMVGMDQKDAYVGDEAQSKRGVLTLKYPIEHGIVTNW
            fucus    MADEDVQALVVDNGSGMCKAGF-GDDAPRAVFPSIVGRPKHPGIMVGMDQKDAYVGDEAQSKRGVLTLKYPIEHGIVTNW
     Saccharomyces   MDSEVAALVIDNGSGMCKAGFAGDDAPRAVFPSIVGRPRHQGIMVGMGQKDSYVGDEAQSKRGILTLRYPIEHGIVTNW
        Consensus    maD.#VqALVI DNGSGMCKAGFaGDDAPRAVFPSIVGRPkH.GIMVGMdQKDaYVGDEAQSKRG!LTLkYPIEHGIVTNW 81        90       100       110       120       130       140       150       160
                     |---------+---------+---------+---------+---------+---------+---------+---------|
     Schizochytrium  DDMEKIWHHTFYNELRVAPEEHPVLLTEAPLNPKANRERMTQIMFETFNVPAMYVNIQAVLSLYASGRTTGAVLDSGDGV
     phytophathora   DDMEKIWHHTFYNELRVAPEEHPVLLTEAPLNPKANRERMTQIMFETFNVPAMYVNIQAVLSLYASGRTTGCVLDSGDGV
            fucus    DDMEKIWHHTFYNELRVAPEEHPVLLTEVPLNPKANKERMTQIMFETFNVLAMYVNIQAVLSLYASGSTTGCVLDSGDGV
     Saccharomyces   DDMEKIWHHTFYNELRVAPEEHPVLLTEAPMNPKSNREKMTQIMFETFNVPAFYVSIQAVLSLYSSGRTTGIVLDSGDGV
        Consensus    DDMEKIWHHTFYNELRVAPEEHPVLLTEaP$NPKaNrErMTQIMFETFNVpAmYVnIQAVLSLYaSGrTTG.VLDSGDGV 161       170       180       190       200       210       220       230       240
                     |---------+---------+---------+---------+---------+---------+---------+---------|
     Schizochytrium  THTVPIYEGYALPHAVLRIDLAGRDLTDYMMKILTERGYSFTTTAEREIVRDIKEKLAYVAQDFDEEMRLAAESSALEKS
     phytophathora   SHTVPIYEGYALPHAIVRLDLAGRDLTDYMMKILTERGYSFTTTAEREIVRDIKEKLTYIALDFDQEMKTAAESSGLEKS
            fucus    SHTVPIYEGYALPHAINRLDLAGRDLTDNLMKVLTERGYSFTTTRERIVRDIREKLTYVALDFDQEMKTAGESSQLEKS
     Saccharomyces   THVVPIYAGFSLPHAILRIDLAGRDLTDYLMKILSERGYSFSTTAEREIVRDIKEKLCYVALDFEQEMQTAAQSSSIEKS
        Consensus    tHtVPIYeGXaLPHAILRiDLAGRDLTDy$MKILtERGYSFtTTaEREIVRDIkEKL.YIAlDF##EM.tAa*SS.IEKS 241       250       260       270       280       290       300       310       320
                     |---------+---------+---------+---------+---------+---------+---------+---------|
     Schizochytrium  YELPDGNFITIGNERFRAPRFLFQPSFIGKEAQGVHDTMFQTIMKCDVDIRKDLYANIVMSGGSTMYEGLAARLEKEMIA
     phytophathora   YELPDGNVIVIGNERFRTPEVLFQPSLIGKEASGIHDCTFQTIMKCDVDIRKDLYCNIVLSGGTTMYPGVGERMTKELTA
            fucus    YELPDGNVIVIGNERFRCPEVLFQPSFIGMESSGIHDCTFKTIMKCDVDIRKDLYGNIVLSGGTTMFPGIGERMTKELTA
     Saccharomyces   YELPDGQVITIGNERFRAPEALFHPSVLGLESAGIDQTTYNSIMKCDVDVRKELYGNIVMSGGTTMFPGIAERMQKEITA
        Consensus    YELPDG#vItIGNERFRaPe.LFqPS.iG.Es.GIh#ttX.tIMKCDVDIRK#LYgNIV$GGtTMXpGIaeRS.KE.tA 321       330       340       350       360       370    376
                     |---------+---------+---------+---------+---------+------|
     Schizochytrium  LAPSTMKIKVVAPPERKYSVWIGGSILASLSTFQQMWISKQEYDESGPSIVHRKCF
     phytophathora   LAPSTMKIKVVAPPERKYSVWIGGSILSSLSTFQQMWISKAEYDESGPSIVHRKCF
            fucus    LAPSTMKIKVVAPPERKYSVWIGGSILASLSTFQQMWISKAEYDESGPSIVHRKCF
     Saccharomyces   LAPSSMKVKIIAPPERKYSVWIGGSILASLTTFQQMWISKQEYDESGPSIVHHKCF
        Consensus    LAPStMKIK!IAPPERKYSVWIGGSILaSLsTFQQMWISKqEYDESGPSIVHrKCF
```

Fig.5

```
                1         10        20        30        40        50        60        70        80
                |---------+---------+---------+---------+---------+---------+---------+---------|
Schizochytrium  MGKTKEHVNLVVIGHVDAGKSTTTGHLIYKCGGIDKRTIEKFEKEAAELGKGSFKYAWVLDKLKAERERGITIDIALWKF
Saccharomyces   MGKEKSHINVVVIGHVDSGKSTTTGHLIYKCGGIDKRTIEKFEKEAAELGKGSFKYAWVLDKLKAERERGITIDIALWKF
Phytophthora                VIGHVDAGKSTTTGHLIYKCGGIDKRTIEKFEKEAAELGKTSFKYAWVLDNLKAERERGITIDIALWKF
Blastocystis    MGKEKPHINLVVIGHVVAGKSTTTGHLIYACGGIDKRTIERFEEGGQRIGKGSFKYAWVLAKMKAERERGITIDISLWKF
Consensus       mgkek.hinlvVIGHVdaGKSTTTGHLIYkCGGIDKRTIEkFEkeaaelGKgSFKYAWVLdk$KAERERGITIDIaLWKF 81        90        100       110       120       130       140       150       160
                |---------+---------+---------+---------+---------+---------+---------+---------|
Schizochytrium  ESPKFDFTVIDAPGHRDFIKNMITGTSQADVAVLVIDSSQGGFEAGIAKDGQTREHALLAFTLGIQQIIVAVNKMDDKTT
Saccharomyces   ETPKYQVTVIDAPGHRDFIKNMITGTSQADCAILIIAGGVGEFEAGISKDGQTREHALLAFTLGVRQLIVAVNKMD---SV
Phytophthora    ESPKYFFTVIDAPGHRDFIKNMITGTSQADCAILVVASGVGEFEAGISKEGQTREHALLAFTLGVKQMVVAINKMDDSSV
Blastocystis    ETRKDFFTIIDAPGHRDFIKNMITGTSQADVAILVIASGAGEFEAGYSKNGQTREHALLANTLGVKQMIVCCNKMDDKSV
Consensus       EtpK.fFTIIDAPGHRDFIKNMITGTSQADvAIL!!asg.GeFEAGisK#GQTREHALLAFTLG!kQm!Va.NKMDdksv 161       170       180       190       200       210       220       230       240
                |---------+---------+---------+---------+---------+---------+---------+---------|
Schizochytrium  MYSEARFNEIVNEVSAYLAKVGFKP--KKIKFVPISGWAGDNMIEKSSNMPWYKG-----------PYLLEALDNIKPP
Saccharomyces   KWDESRFQEIVKETSNFIKKVGYNP--KTVPFVPISGWNGDNMIEATTNAPWYKGWEKETKAGVVKGKTLLEAIDAIEQP
Phytophthora    MYGQARYEEIKSEVTTYLKKVGYKP--AKIPFVPISGWEGDNMIDRSTNMPWYKG-----------PFLLEALDNLNAP
Blastocystis    MYSEARYKEIKNEMTSFLTKVGYAKVEERIPFIPISGFNGDNMIEHSANMPWYKG-----------PTLLEALDNVHPP
Consensus       .ys#aR%.EIknE.t.%1.KVG%.p....!pF!PISGwnGDNMI#.s.NmPWYKG...........ptLLEAlDn..pP 241       250       260       270       280       290       300       310       320
                |---------+---------+---------+---------+---------+---------+---------+---------|
Schizochytrium  KRPIDKPLRLPLQDVYKIGGIGTVPVGRVETGVIKPGMTAYFAPTGVQTEVKSVEMHHESIPEATPGDNVGFNVKNVSVK
Saccharomyces   SRPTDKPLRLPLQDVYKIGGIGTVPVGRVETGVIKPGMVVTFAPAGVTTEVKSVEMHHEQLEQGVPGDNVGFNVKNVSVK
Phytophthora    KRPSDKPLRLPLQDVYKIGGIGTVPVGRVETGVIKPGMVATFGPVGLSTEVKSVEMHHESLPEAVPGDNVGFNVKNVSVK
Blastocystis    KRPVDKPLRLPLQDVYKIGGIGTVPVGRVETGVLKPGMTVTFAPVNVSTEVKSVEMHHESIPQALPGDNVGFNVNNVSVE
Consensus       kRP.DKPLRLPLQDVYKIGGIGTVPVGRVETGVikPGMtvtFaPvgvsTEVKSVEMHHEsip#a.PGDNVGFNVkNVSVk 321       330       340       350       360       370       380       390       400
                |---------+---------+---------+---------+---------+---------+---------+---------|
Schizochytrium  DIKRGNVCGDAKNDPPRGANSFLAQVIVMGHPGEIRAGYAPVLDCHTAHIACKFAEIQNKMDRRSGKILEDAPKFIKSGD
Saccharomyces   EIRRGNVCGDAKNDPPKGCASFNATVIVLNHPGQISAGYSPVLDCHTAHIACRFDELLEKNDRRSGKKLEDHPKFLKSGD
Phytophthora    ELRRGFVASDSKNDPAKATQDFTAQVIVLNHPGQIGNGYSPVLDCHTAHVACKFKEITEKMDRRSGKVLETAPKFVKSGD
Blastocystis    DIHRGNVCGDAKNDPPCKTES-DAQVIVMNHPSGIRPGYCPVVDCHTAHIACKFEKIMSEMDKRTGKVLRENPDIVKNGK
Consensus       #i.RGnVcgDaKNDPp..t.sf.AqVIV$nHPg.Ir.GY.PVIDCHTAHIACkF.ei..kmDrRsGKvLe..PkfvKsGd 401       410       420       430       440       450       46062
                |---------+---------+---------+---------+---------+---------+-|
Schizochytrium  SAMVKMIPSKKMCVESFTEYPPLGRFAVRDMRVTVAVGVIKEVEKGDK
Saccharomyces   AALVKFVPSKPMCVEAFSEYPPLGRFAVRDMRQTVAVGVIKSVDKTEKAAKVTKAAQKAAKK
Phytophthora    ACMVILEPSKPMTVESFQEYPPLGRFAVRDMRQTVAVGVIKSVNKKEASGKGGAKKK
Blastocystis    SMHAQLVPSKPHCVETFSDYPPLGRFAVRDMRQTVAVGIIKSTVRAK
Consensus       s.$v.lvPSKpMcVE.Fs#YPPLGRFAVRDMRqTVAVGIIKsv.k................
```

Fig.6

```
                1         10        20        30        40        50        60        70        80
                |---------+---------+---------+---------+---------+---------+---------+---------|
Schizochytrium  MSADAPIMGINGFGRIGRLVFRTAFETGNVKVVAIND-LLDLDYIAYLLKYDSVHGPFKGTIEIKDGNLVVNGETVKVYS
Phaeodactylum    MPVSLGINGFGRIGRLVMRAALEHPDATVVAVNDPFLTPEYAAYQFKYDSVHGTYSEDVSFEEGYLVVGDKKIRFFS
Phytophthora       SKVGINGFGRIGRLVLRAAAKNPEINVVAVNGPFIATKYMEYMLKYDTVHGRFGGELSHDEQNIYVDGKAIRVFN
Saccharomyces    MVRVAINGFGRIGRLVMRIALSRPNVEVVALNDPFITNDYAAYMFKYDSTHGRYAGEVSHDDKHIIVDGKKIATYQ
Consensus       ....v..gINGFGRIGRLVmRaAle.p#v.VVAvNdpflt.dYaaY.lKYDsvHG.X.g.vs..#gnlvV.gkk!rv%s 81        90        100       110       120       130       140       150       160
                |---------+---------+---------+---------+---------+---------+---------+---------|
Schizochytrium  ERDPSNIPWGENGVEFVCESTGIFTTAEKCQAHLRGGAKRVIISAPPKDDTPHFVMGVNHEDYDGE-DITSNASCTTNCL
Phaeodactylum   ERNPEEIGWGSVGAEIVCESTGVFTTIDKAQAHINGGAEKVVISAPSAD-APHYVMGVNHTTYSGA-TVFSNASCTTNCL
Phytophthora    EMNPANIKWGEEQVQYVVESTGAFTTTEKASAHLKNGVEKVVISAPSSD-APMFVMGVNHELYEKNMHVVSNASCTTNCL
Saccharomyces   ERDPANLPWGSSNVDIAIDSTGVFKELDTAQKHIDAGAKKVVITAPSST-APMFVMGVNEVKYTSDLKIVSNASCTTNCL
Consensus       Er#P.#ipWGe.gv#ivc#STGvFtt.#kaqaHi.gGaekVIIsAPs.d.aPMXVMGVNhe.Y.g...!.SNASCTTNCL 161       170       180       190       200       210       220       230       240
                |---------+---------+---------+---------+---------+---------+---------+---------|
Schizochytrium  APLAKVINDNFGIVEGLMTTVHAMTANQLTVDGPSKGGKDWRAGRSAGAHVIPSSTGAAKAVGKVIPALNGKLTGMAFRV
Phaeodactylum   APLAKVLHEEFGIVEGLMTTIHAGTATQLVVDGPAKRGKDWRAGRSSLANLIPASTGAAKAVGKVIPELNGKLTGMAVRV
Phytophthora    APLAKVVNDKFGIKEGLMTTVHAVTATQKTVDGPSK---KDWRGGRGACFNIIPSSTGAAKAVGKVIPSLNGKLTGMSFRV
Saccharomyces   APLAKVINDAFGIEEGLMTTVHSLTATQKTVDGPSH---KDWRGGRTASGNIIPSSTGAAKAVGKVLPELQGKLTGMAFRV
Consensus       APLAKVin#.FGIvEGLMTTIHa.TAtQltVDGPsk.gKDWRaGRsa.aN.IPsSTGAAKAVGKViPeL#GKLTGMaFRV 241       250       260       270       280       290       300       310       320
                |---------+---------+---------+---------+---------+---------+---------+---------|
Schizochytrium  PTPDVSVVDLTCKIEKPNSYEEIKKVLKAASENELKGILGYTEDAVVSNDFVGNTNSSIFDADAGIMLNDTFVKLISWYD
Phaeodactylum   PTADVSNVDLTIRTEKAVSAAELKAALKKASEGPMKGILGYTEDAVVSQDFVHDPRSSIVDASAGIALNDNFHKVIAWYD
Phytophthora    PTADVSVVDLTARLVNPASYEEIKAAIKSASENEMKGILGYTEEAVVSSDFIGDSHSSIFDAEAGIALTDDFVKLVSWYD
Saccharomyces   PTVDVSVVDLTVKLDKETTYDEIKKVVKAAAEGKLKGVLGYTEDAVVSSDFLGDSHSSIFDASAGIQLSPKFVKLVSWYD
Consensus       PTaDVSvVDLT.r.ekp.syeEiKaalKaAsEne$KG!LGYTE#AVVS.DFvg#..SSIfDAsAGIaLnd.FvKl!sWYD 321       330       341
                |---------+---------+|
Schizochytrium  NERGYSTRLTDLACYIKSTGK
Phaeodactylum   NEWGYSNRLVDLAIYTSGK
Phytophthora    NEWGYS
Saccharomyces   NEYGYSTRVVDLVEHIAKA
Consensus       NEwGYStrlvdla.yi.....
```

Expression amount (M) = 10 (CO-CX) / PCR product MW

|  | 10(CO-CX) | PCR product MW | Expression amount (M) |
|---|---|---|---|
| actin | $1.93 \times 10^{-4}$ | 91932 | $2.10 \times 10^{-6}$ |
| ef1α | $1.00 \times 10^{-4}$ | 92549 | $1.08 \times 10^{-6}$ |
| gapdh | $1.14 \times 10^{-5}$ | 91314 | $1.25 \times 10^{-7}$ |

Fig.14

```
                  1        10        20        30        40        50        60        70
                  I---------+---------+---------+---------+---------+---------+---------I
Actin (Kpn I)   CACTCACAT-TGGTAG-TCTGTAGACATGATTTGGACCTTCTGTAGGCAGAGAGTACCTACTAGGAGCG
Acton (EcoR I)  TAATTCATGTATGGTAGGTATGTAGATAGG---TAGGTGGGAAGTAGTCTGGATGTTTTATCATTAAAGG
    Consensus   ..A.TCA..T.TGGTAG.T.TGTAGA.A.G...T.G......GTAG.C.G...GT.....C....A..G 71        80        90       100       110       120       130       140
                  I---------+---------+---------+---------+---------+---------+---------I
                TCTTCCAATAATCGCCTCGATTTCCCCAACCTGGATGATGCTGGTGGCTCAACTTGAACTAAAACCTGAG
                TTGGACTAGACGCACATGTTTTTATTTAAA--GGACACAACTGGAAG-TCAG-TCAATCTTAG--CTGGG
                T....C.A.A..C.C.T...TTT....AA...GGA.....CTGG...G.TCA..T..A.CT.A...CTG.G 141       150       160       170       180       190       200       210
                  I---------+---------+---------+---------+---------+---------+---------I
                GATGAAG----GAGCCACTCGATT-CCACGCACACCCTTCAGGTGGTCATTTGCAGGTTAG-CGATAGAG
                GTTCTCACCTTTTTCAAATTGATTGCCCCTTGCAACTAGCTATCTAGCTATAGCTGGCTAGTAGATTTTT
                G.T..........C.A.T.GATT.CC.C...CA.C...C.......C..T.GC.GG.TAG..GAT....

211       220       230       240       250       260       270       280
                  I---------+---------+---------+---------+---------+---------+---------I
                GTATCTCTCACAAACACTGTAAATAGTTTTGTGAGTAAATACACACACGAGCACTCCTATAAAGGGTGTG
                GGAAGTCGGGTATTGAAGGTATGCGCACACGTGCA-AATCCCTCCTACAATCACTGCCTCCTAAACCCTT
                G.A..TC....A...A..GTA........GTG...AA...C.C..AC.A.CACT.C.....A......T.

281       290       300       310       320       330       340       350
                  I---------+---------+---------+---------+---------+---------+---------I
                TAAGCTAAGGAAAATCCC---CTCGCAACACACTGAGTATCAAAAGAGGAACCTACGACTAAGAAGGTTA
                CCCTCANCAAGACCTCCAGATATTACTCCAAAGTGAACAAAAGTATTGGTGCACCCTCACAATAATACAA
                ....C......A..TCC.....T..C..CA.A.TGA..A..A..A..GG..C...C....AA.AA....A 351       360       370       380       390       400       410       420
                  I---------+---------+---------+---------+---------+---------+---------I
                TCATAAATGGATGTAATCAGAGGAGGTAACACTGTAAATTTAT GAGACAGTGGAGGGTCTTTGGGCACG
                ACACGCTAAAATGTGCT-AGAGG-GCCCCCACTGAGAAAGGTA GTGATAGAGGAGTGTCTTCGGGCACG
                .CA......ATGT..T.AGAGG.G....CACTG..AA..... G.GA.AG.GGAG.GTCTT.GGGCACG 421       430       440       450       460       470       480       490
                  I---------+---------+---------+---------+---------+---------+---------I
                AAGATCTGCAAGCGCGCCATCAGCAGATCCGCAACCTTCGAGCTCAAGAAGCAACTCAACAGTAGAAGAA
                AAGATCTGCAAGCGCGCCATCAGCAGAACCGCAACCTTCGAGCCCAAGAAGCAACTCAACAGTAGCAGAA
                AAGATCTGCAAGCGCGCCATCAGCAGA.CCGCAACCTTCGAGC.CAAGAAGCAACTCAACAGTAG.AGAA 491       500    51612
                  I---------+------+-I
                CAAGCACCCAACTAGCAAAATG
                CAAGCTCCCAACTAGCAAAATG
                CAAGC.CCCAACTAGCAAAATG
```

METHOD FOR INTRODUCING A GENE INTO *LABYRINTHULOMYCOTA*

TECHNICAL FIELD

The present invention relates to a method for introducing a gene into labyrinthulomycota.

BACKGROUND ART

Labyrinthulomycota is a group of eukaryotic single-cell microorganisms widely distributed in the ocean, and is classified in stramenopile (Kingdom Chromista, Heterokontae) having flagella of unequal length. This organism is an oil-containing microorganism that accumulates therein $C_{22}$ polyunsaturated fatty acid (PUFA) such as docosahexaenoic acid (DHA) known as a functional food ingredient, and has therefore received attention as a source of single cell oil. The single cell oils are lipids produced by microorganisms. Lipids produced by microorganisms include special one not contained in oil-containing plants and in animal fats and oils and one having different composition. Therefore, these lipids are expected to be applied as novel lipid resources to pharmaceutical drugs, functional foods, feed, and the like. Examples of characteristics of microorganism fats and oils include, in addition to its peculiarity different from animal and plant fats and oils as described above, high productivity resulting from rapid proliferation, and ease of breeding of microorganism strains suitable for specific fats and oils production. The oil-containing microorganisms include *Mucor* and *Mortierella* filamentous fungi as γ-linolenic acid (C18:3)-producing microorganisms as well as *Mortierella* filamentous fungi as arachidonic acid (C20:4)-producing microorganisms. The γ-linolenic acid production using the microorganisms has already been put in industrial use. Because $C_{22}$ fatty acids such as DHA grow in demand by the discovery of a variety of its high physiological functions and one of microorganism species of Labyrinthulomycota has a characteristic of producing PUFA as well as carotenoids such as astaxanthin exhibiting similar high physiological functions, which is not seen in existing biological resources, the development of production systems of these functional lipids using Labyrinthulomycota and systems effectively using the functional lipids as microorganism feed has been demanded. However, production mechanisms of PUFA and carotenoid, which are key factors in the development of the production system such as the optimization of culture conditions or molecular breeding, remain unexplained. Particularly, synthetic pathways of DHA in microorganisms of Labyrinthulomycota have not been elucidated.

In Japanese Patent No. 2764572, Japanese Patent Publication (Kokai) No. 2003-189846A (2003), and Molecular Biology of the Gene, Watson et al., Chapter 19, p. 595-620, Toppan, microorganisms known to accumulate polyunsaturated fatty acid including docosahexaenoic acid and other unsaturated fatty acids or carotenoid in the bodies have been explored diligently, and Labyrinthulomycota with high productivity has been found from among a number of microorganism groups. However, the productivity of polyunsaturated fatty acid and carotenoid by these microorganisms of Labyrinthulomycota disclosed therein is less than sufficient.

DISCLOSURE OF THE INVENTION

The development of transformation systems for Labyrinthulomycota provides for gene disruption and the elucidation of synthetic pathways of DHA in Labyrinthulomycota. This solves problems as described above and also leads to the elucidation of biosynthetic mechanisms of carotenoid. Moreover, molecular breeding by this microorganism is also accomplished, leading to the development of production systems of a variety of functional lipids. Moreover, if a gene involved in the biosynthesis of DHA or carotenoid is isolated from such a microorganism, novel sources of DHA and carotenoid can be provided by introducing the gene into other microorganisms, plants, and the like. Phaeophyceae, Bacillariophyta, Oomycetes, and so on belong to the same stramenopile, and transformation systems for a few species of these microorganisms have already been developed. However, transformation systems for Labyrinthulomycota have not been developed at all. Thus, an object of the present invention is to provide a transformation system for Labyrinthulomycota that allows the elucidation of biosynthetic mechanisms of lipids such as PUFA and carotenoids as well as for the construction of a high production system and the design and development of novel functional lipid molecules by the control of the mechanisms. Namely, a problem to be solved by the present invention is to provide a method for introducing a gene into labyrinthulomycota which is capable for the transformation of Labyrinthulomycota by introducing an foreign gene into it.

The present inventors have conducted diligent studies for solving the problems and have successfully introduced a transgene into cells of Labyrinthulomycota in such a way that the cells of Labyrinthulomycota can be transformed by introducing a foreign gene for improving the ability of Labyrinthulomycota to produce useful substances, thereby completing the present invention.

Thus, the present invention provides a method for introducing a transgene into a cell of Labyrinthulomycota, which comprises introducing into a cell of Labyrinthulomycota a recombinant vector comprising a transgene and a nucleotide sequence which is homologous to a part of chromosomal DNA of Labyrinthulomycota and is capable of homologous recombination with the chromosomal DNA, and then inducing homologous recombination in this homologous nucleotide sequence.

Preferably, the recombinant vector is a recombinant vector comprising at least (1) a nucleotide sequence which is homologous to a part of chromosomal DNA of Labyrinthulomycota and is capable of homologous recombination with the chromosomal DNA, (2) a selection marker gene having a promoter sequence located upstream and a terminator sequence located downstream, and (3) a transgene having a promoter sequence located upstream and a terminator sequence located downstream.

Preferably, the recombinant vector is a linearized plasmid.

Preferably, the recombinant vector is introduced into the cell of Labyrinthulomycota by using electroporation, a gene gun, or the drug treatment of the cell membrane.

Preferably, the nucleotide sequence which is homologous to a part of chromosomal DNA of Labyrinthulomycota and is capable of homologous recombination with the chromosomal DNA is an 18S rRNA gene sequence of Labyrinthulomycota.

Preferably, the nucleotide sequence which is homologous to a part of chromosomal DNA of Labyrinthulomycota and is capable of homologous recombination with the chromosomal DNA is a nucleotide sequence of 18S rRNA of *Schizochytrium* sp CB15-5 described in SEQ ID NO: 1.

Preferably, the recombinant vector comprising the transgene is introduced into the cell of Labyrinthulomycota collected from a culture medium that has reached stationary phase.

Preferably, the cell of Labyrinthulomycota is a cell of *Schizochytrium* sp.

BRIEF DESCRIPTION OF THE DRAWINGS

FIG. 3 shows a phylogenetic tree of a 18S rRNA gene;

FIG. 4 shows the comparison of predicted amino acid sequences (actin). The amino acid sequence encoded by the actin gene was examined for its homology to those of related microorganisms.

*Schizochytrium* sp. CB15-5 AB200876 (Labyrinthulida) (SEQ ID NO: 110)

*Phytophthora brassicae* AY244551-1 (Oomycetes) (SEQ ID NO: 111)

*Fucus distichus* U11697 (Phaeophyceae) (SEQ ID NO: 112)

*Saccharomyces cerevisiae* V01288-1 (Fungi) (SEQ ID NO: 113)

Region conserved in Actin protein (54-64 Actins signature, 105-117 Actins and actin-related proteins signature, 357-365 Actins signature) (SEQ ID NO: 114);

FIG. 5 shows the comparison of predicted amino acid sequences (ef1α). The amino acid sequence encoded by the ef1α gene was examined for its homology to those of related microorganisms.

*Schizochytrium* sp. CB15-5 AB200877 (Labyrinthulida) (SEQ ID NO: 115)

*Saccharomyces cerevisiae* X78993-28 (Fungi) (SEQ ID NO: 116)

*Phytophthora infestans* AJ249839-1 (Oomycetes) (SEQ ID NO: 117)

*Blastocystis hominis* D64080-1 (*Blastocystis*) (SEQ ID NO: 118)

Region conserved in Ef1α protein (14-21 ATP/GTP-binding site motif A (P-loop) 61-76 GTP binding elongation factors signature) (SEQ ID NO: 119);

FIG. 6 shows the comparison of predicted amino acid sequences (gapdh). The amino acid sequence encoded by the gapdh gene was examined for its homology to those of related microorganisms.

*Schizochytrium* sp. CB15-5 AB200878 (Labyrinthulida) (SEQ ID NO: 120)

*Phaeodactylum tricornutum* AAF34325 (Bacillariophyta) (SEQ ID NO: 121)

*Phytophthora palmivora* AY292378-1 (Oomycetes) (SEQ ID NO: 122)

Saccharomyces cerevisiae V01300-1 (Fungi) (SEQ ID NO: 123)

Figure 7:
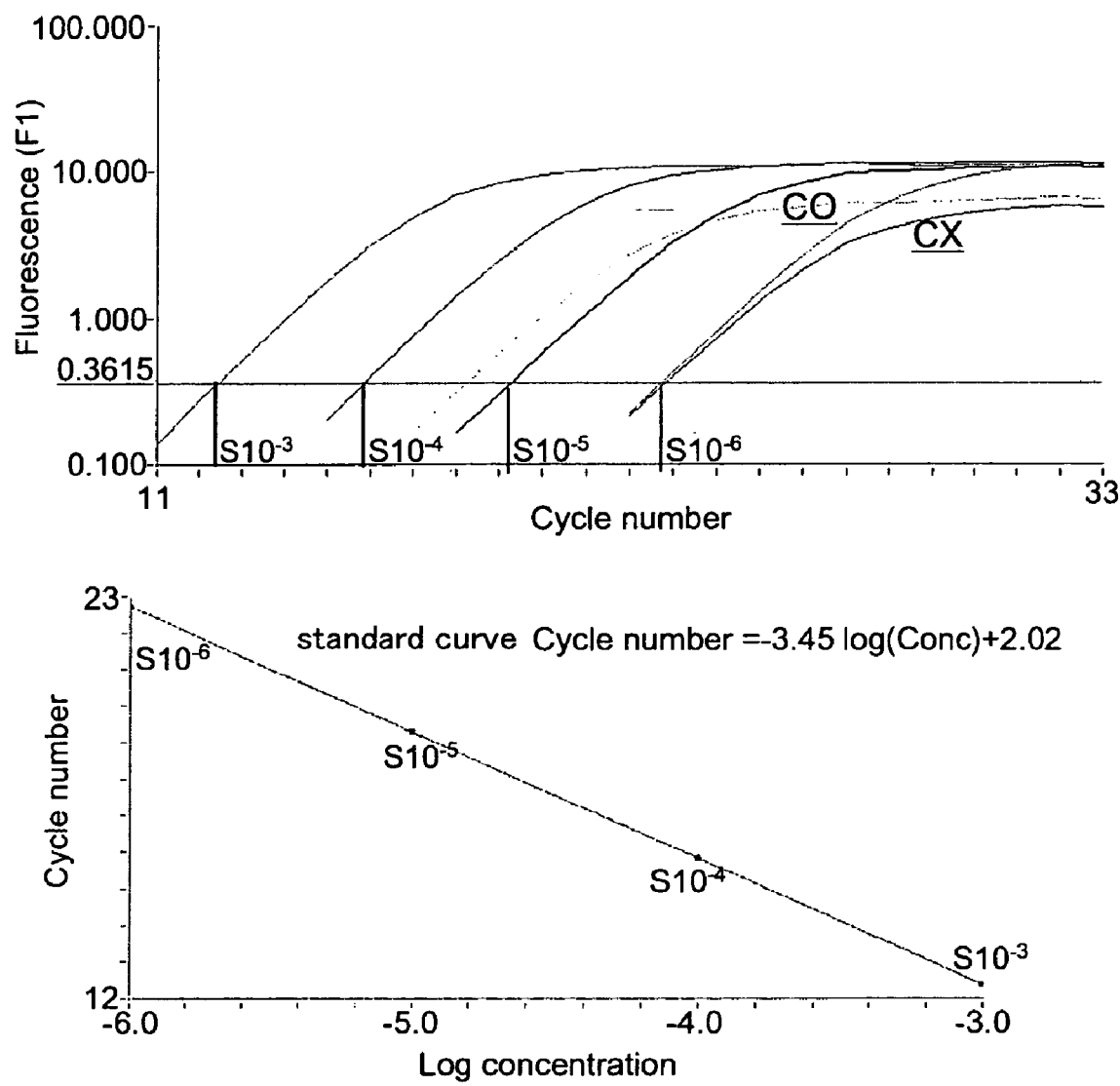
Figure 8:
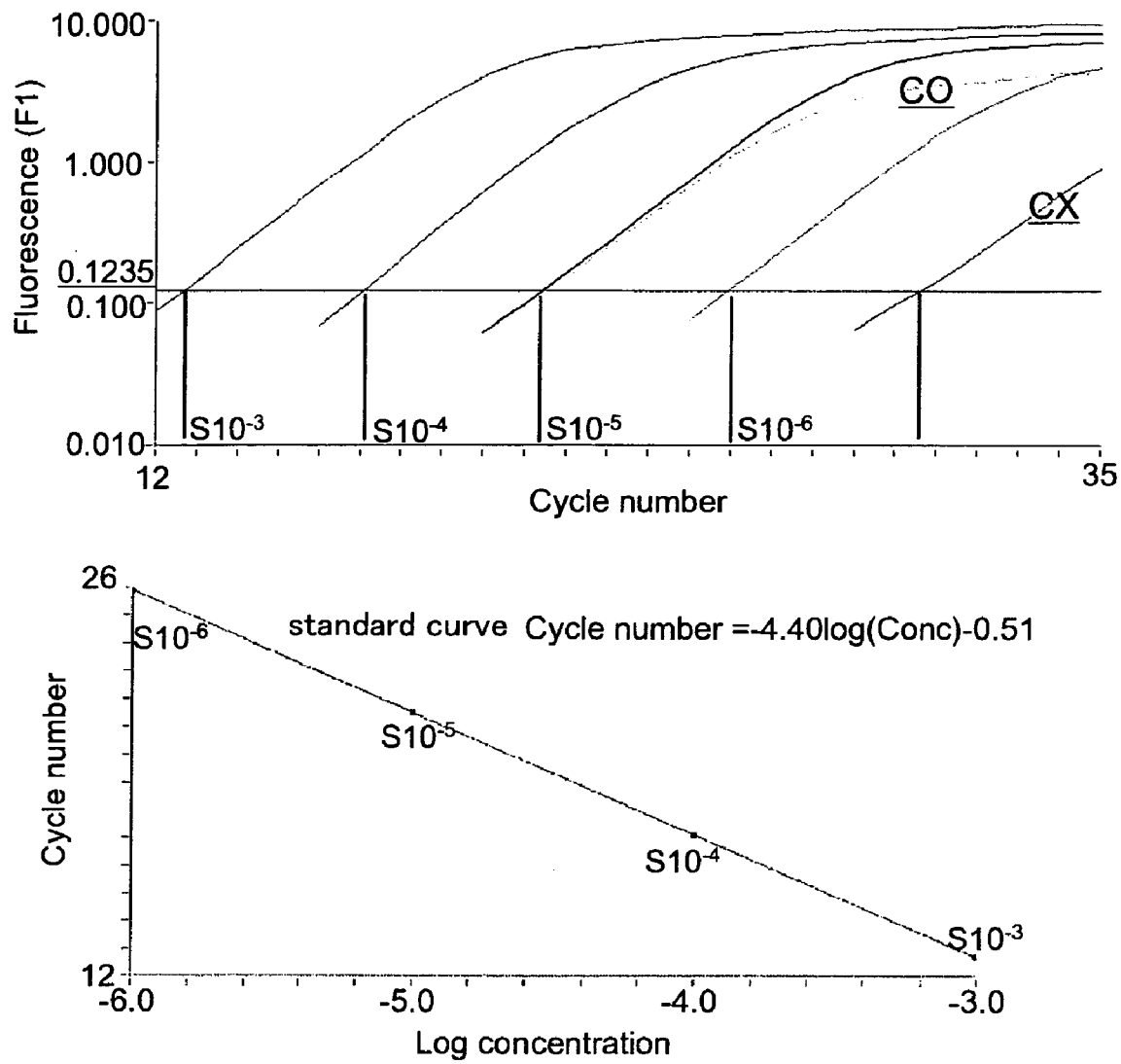
Figure 9:
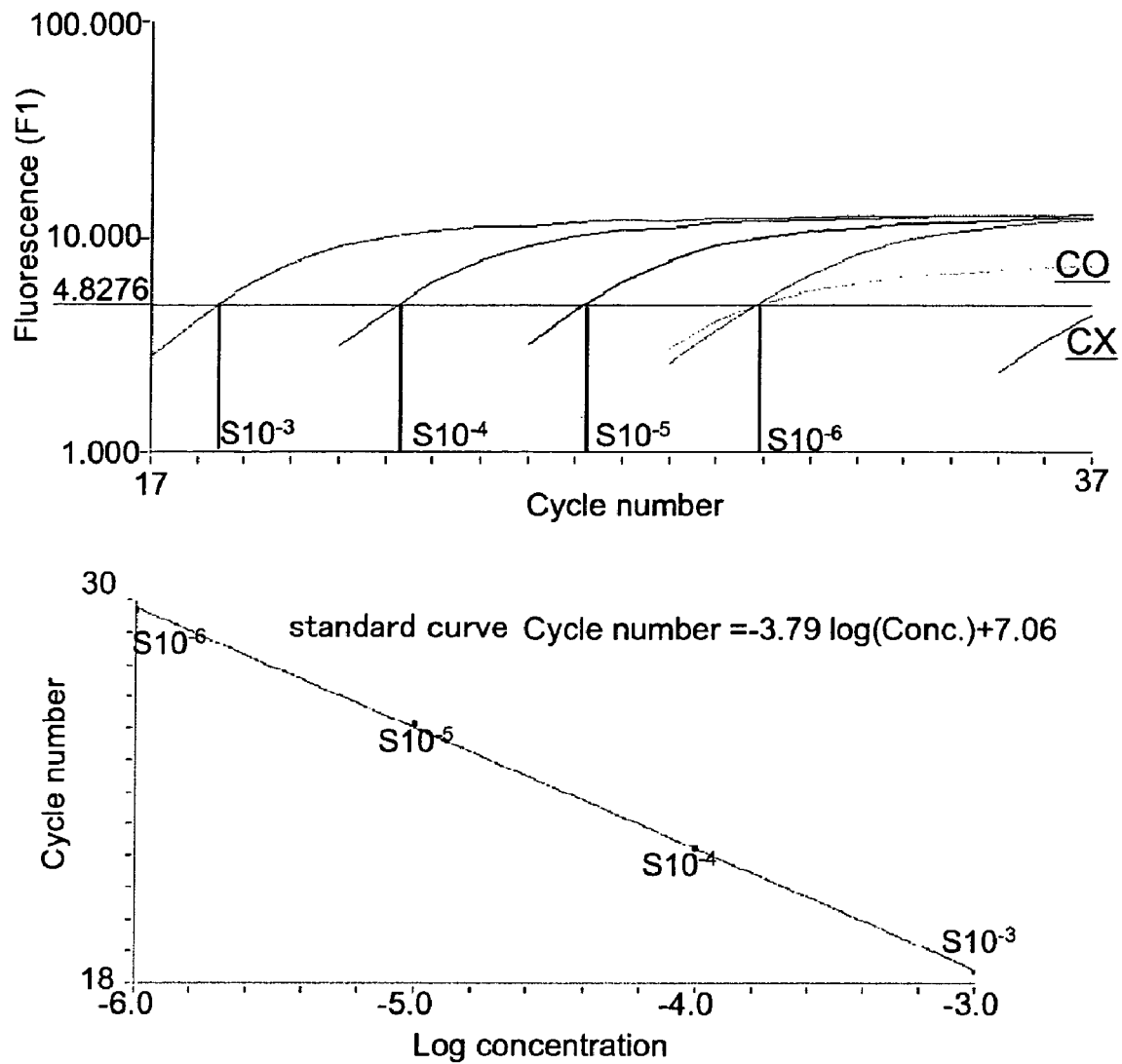
Figure 10:
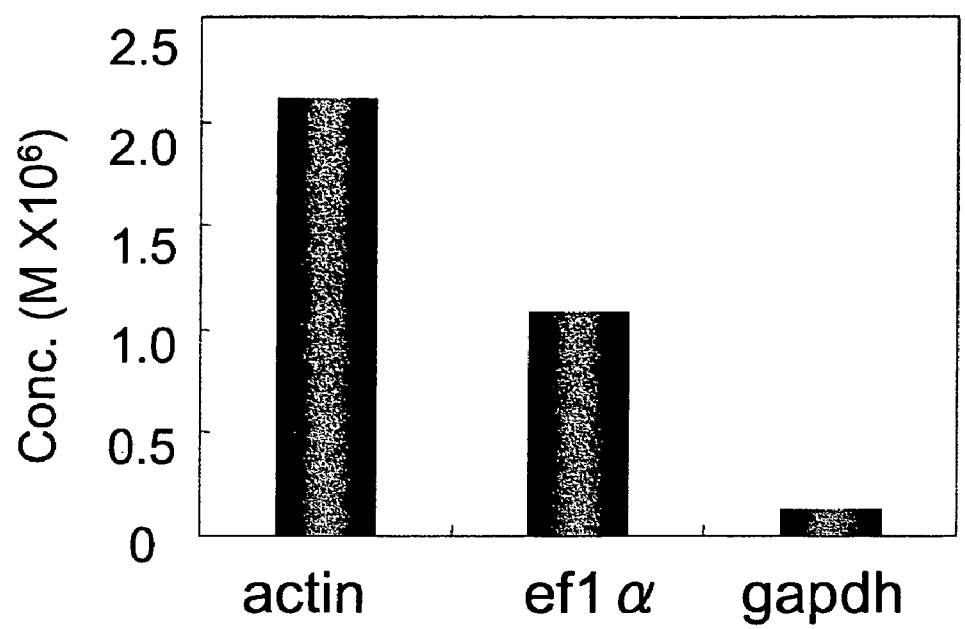
Figure 11:
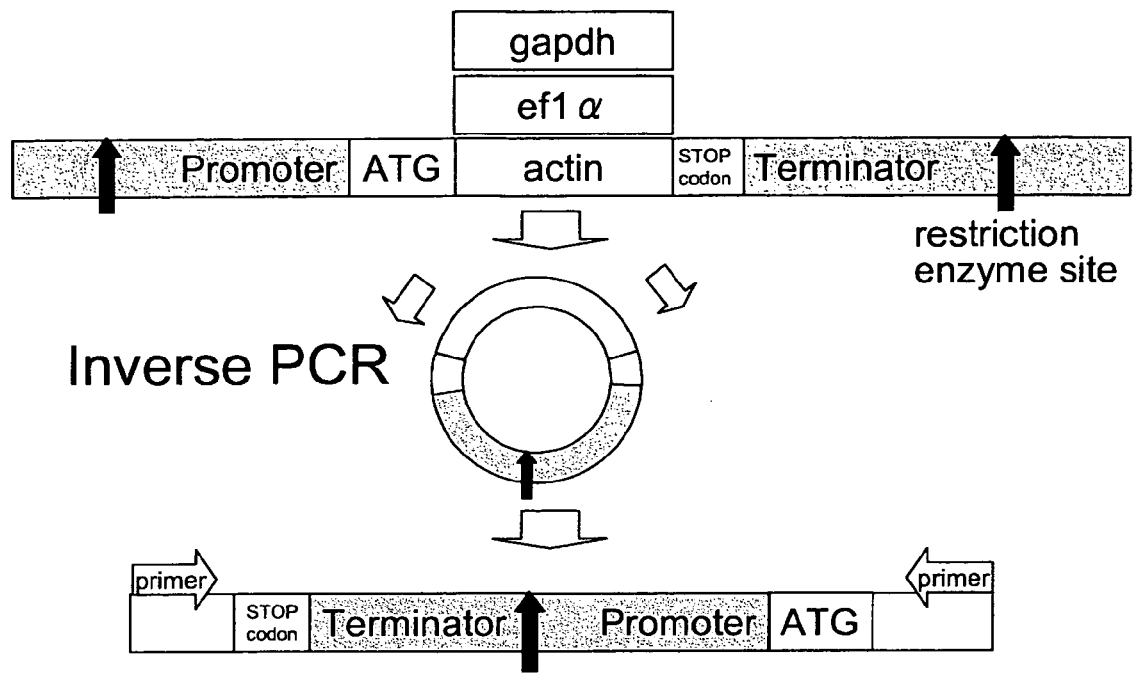
Figure 12:
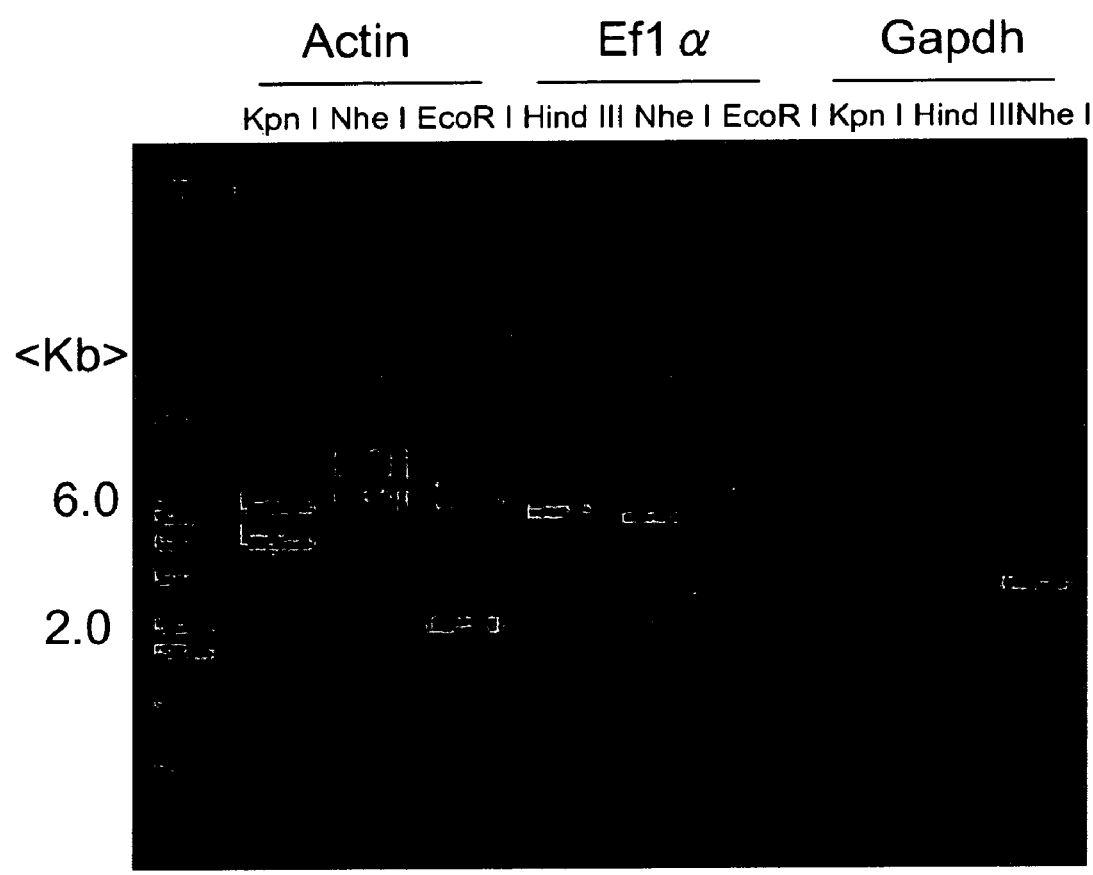
Figure 13:
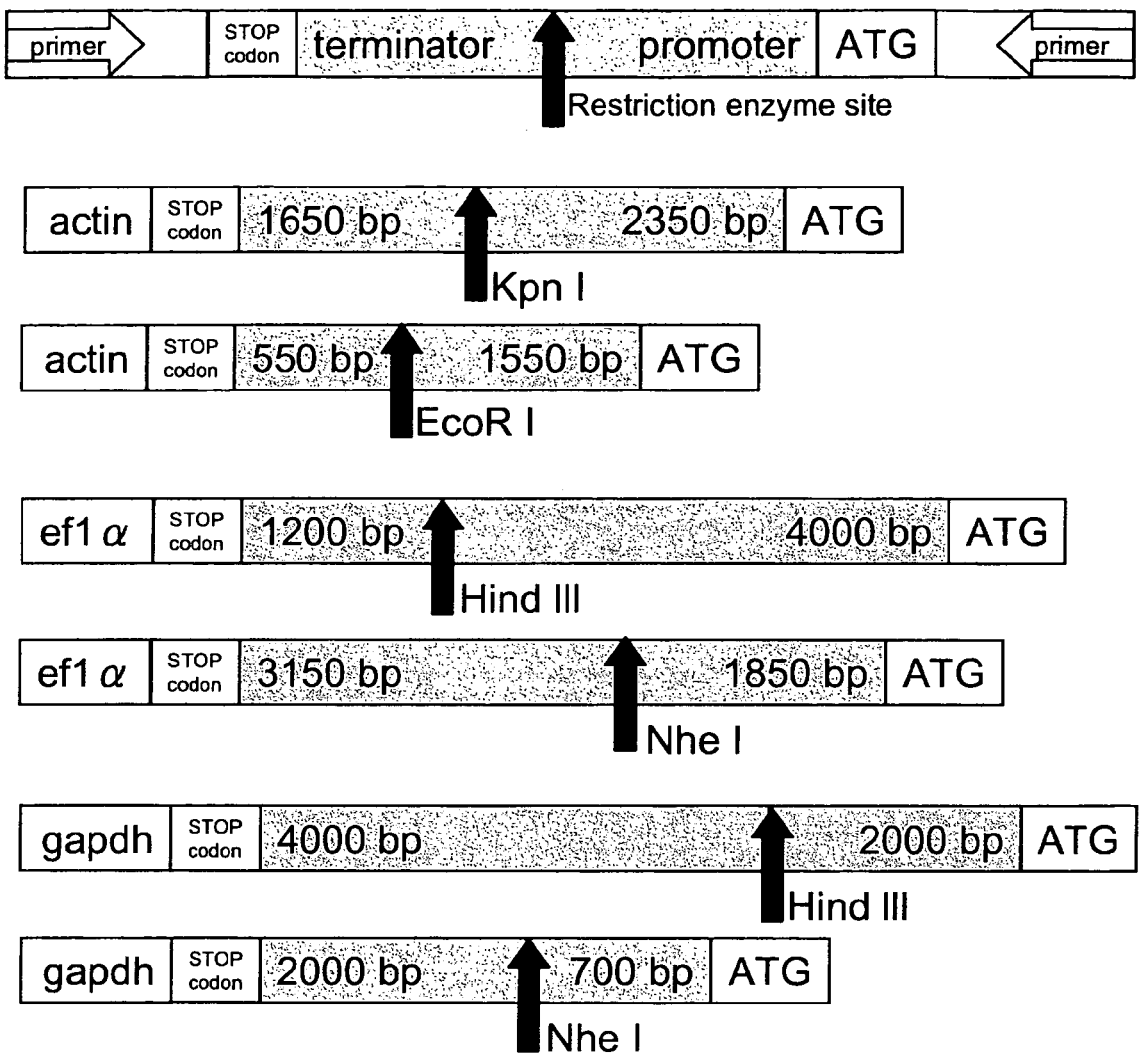
Figure 15:
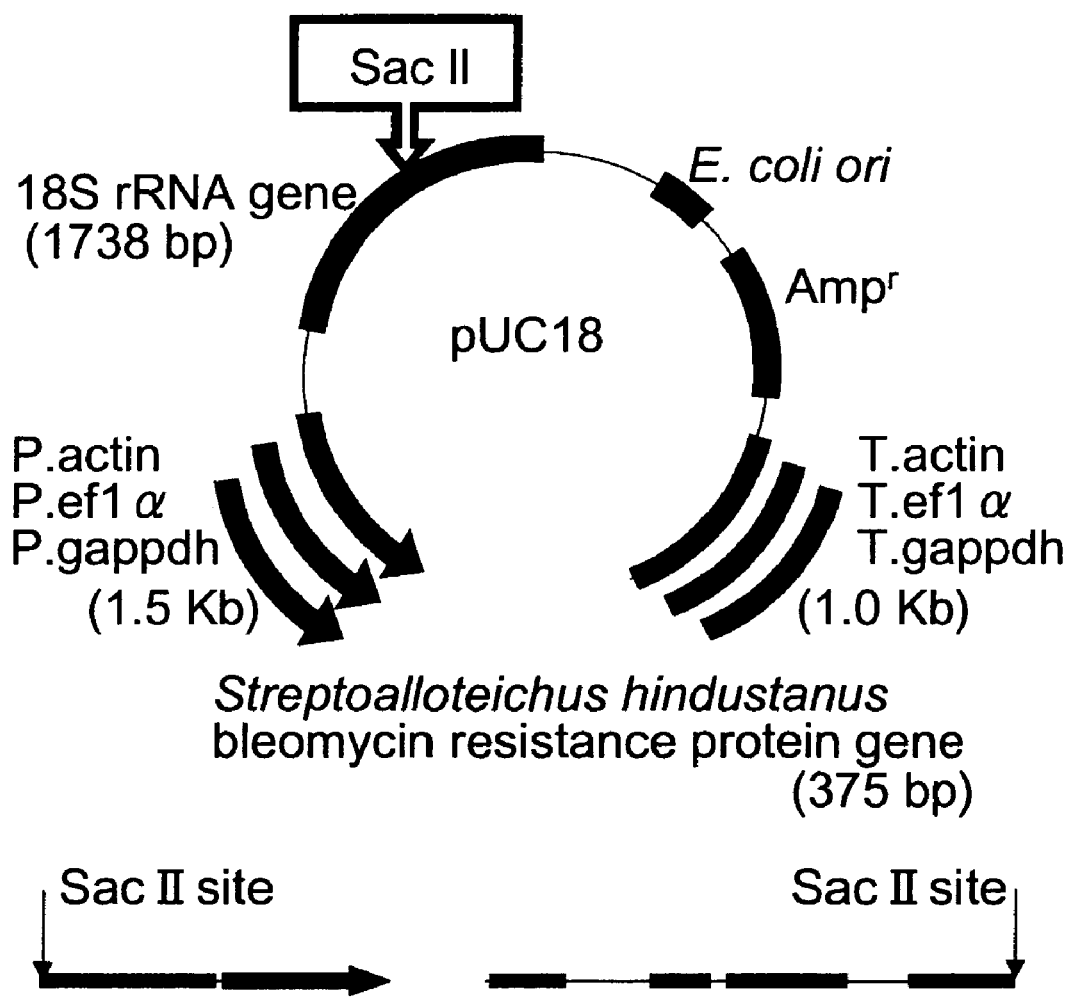
Figure 16:
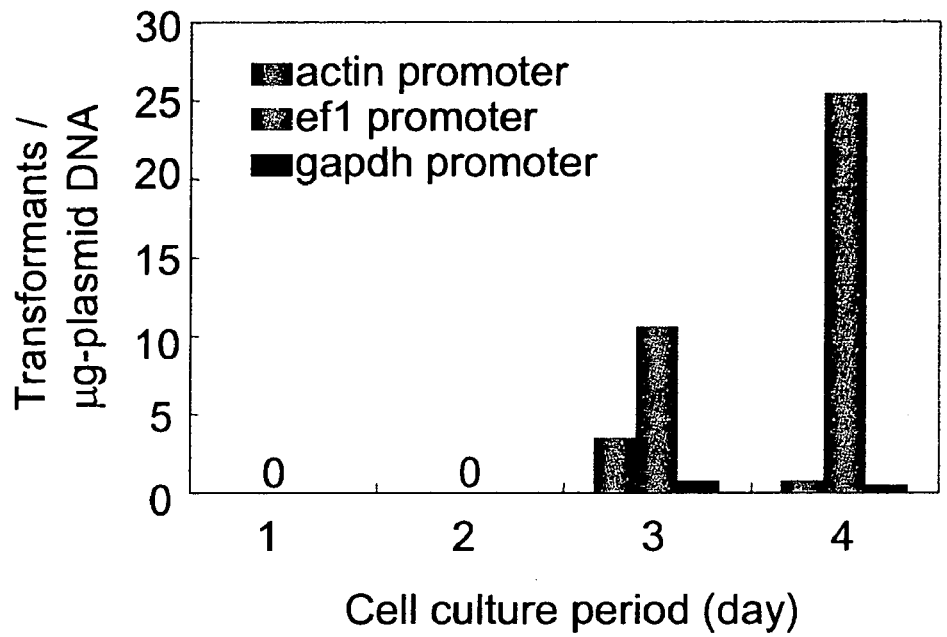
Figure 17:
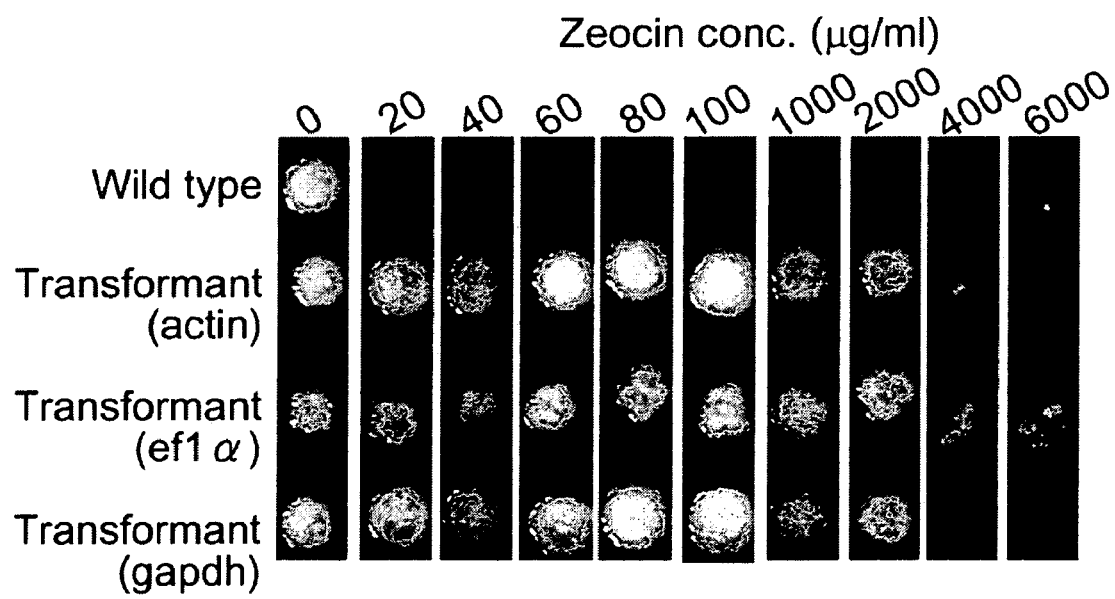
Figure 18:
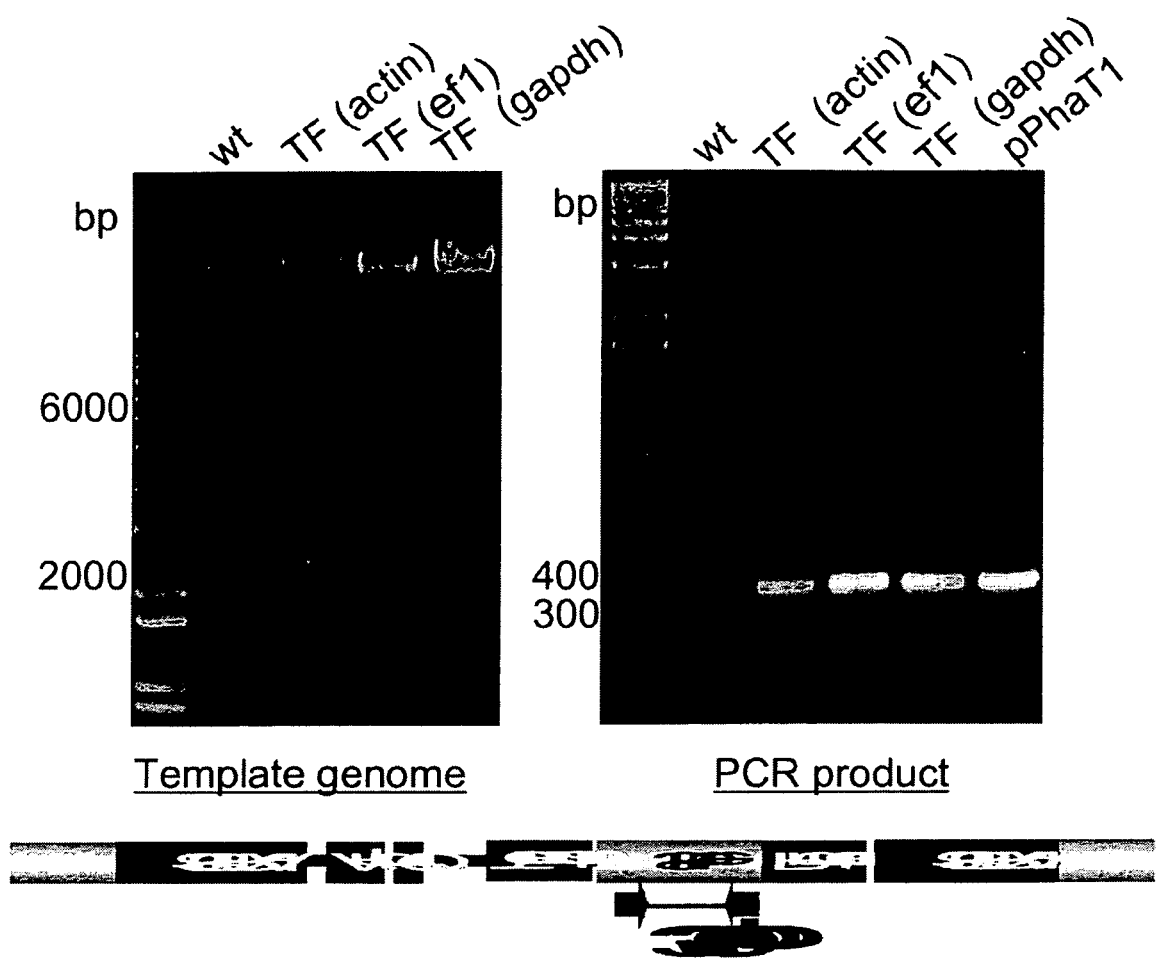
Figure 19:
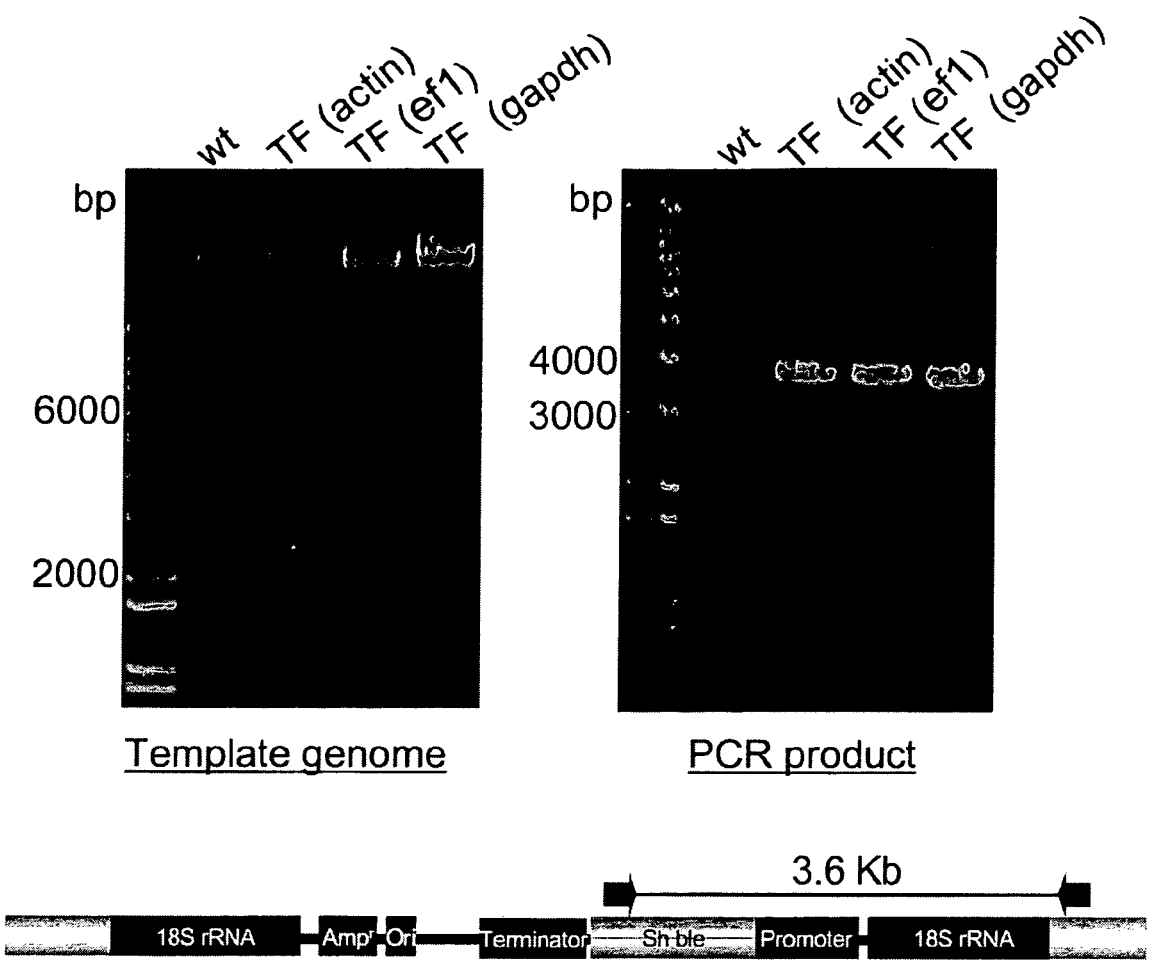
Figure 20:
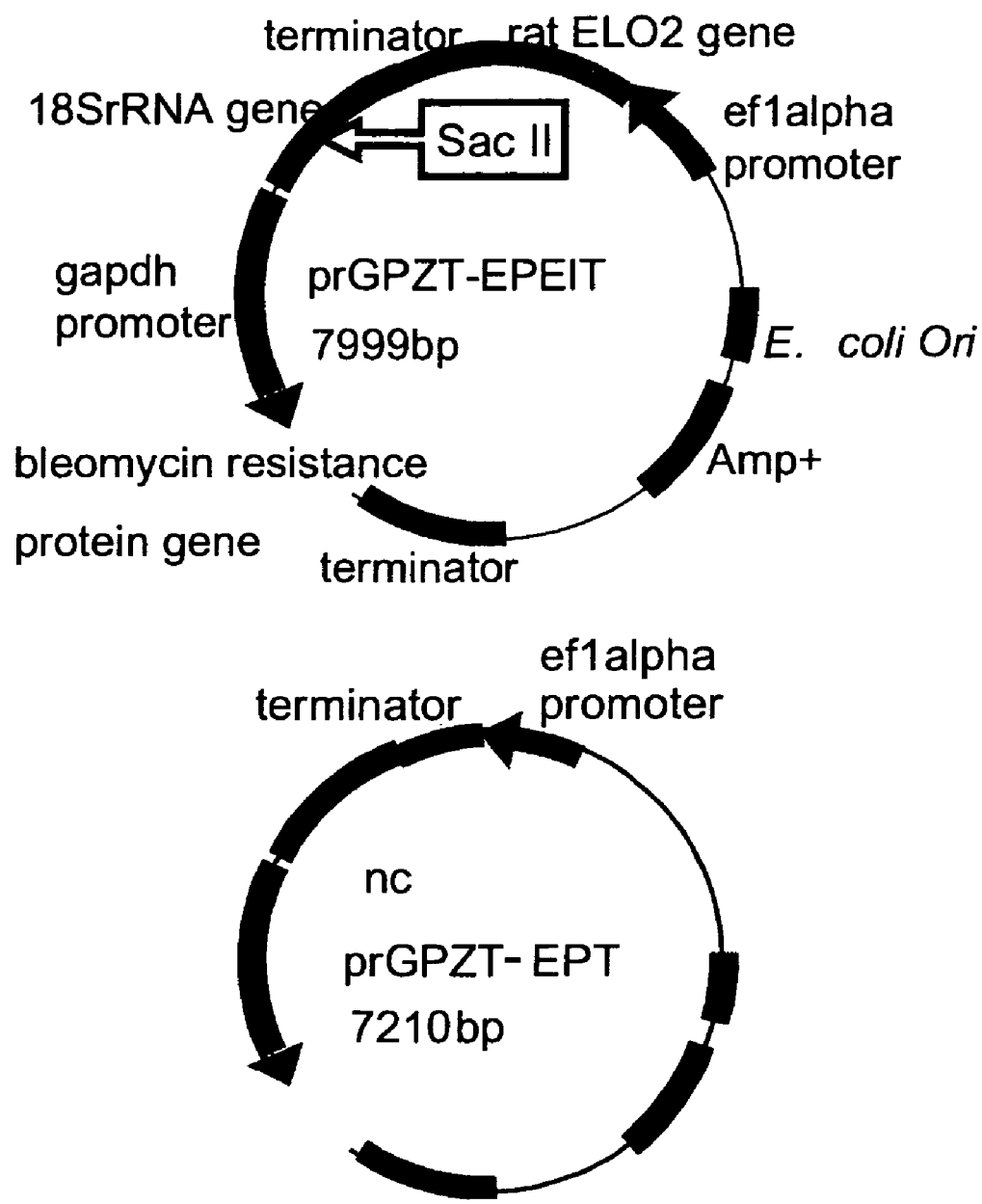

Region conserved in Gapdh protein (151-158 Glyceraldehyde 3-phosphate dehydrogenaseactive site) (SEQ ID NO: 124);

FIG. 7 shows real time PCR (actin) analysis. Data of real time PCR indicating the fluorescence value of each sample in the PCR cycle was analyzed by Fit Point Method of "Light-Cycler Software Ver. 3.5 (Roche)," and a standard curve was prepared with a cycle number of a standard sample at the fluorescence value 0.3615 as the vertical axis against a log value of concentration as the horizontal axis, and was used to calculate a sample concentration from the cycle number of the sample;

FIG. 8 shows real time PCR (ef1α) analysis. Data of real time PCR indicating the fluorescence value of each sample in the PCR cycle was analyzed by Fit Point Method of "Light-Cycler Software Ver. 3.5 (Roche)," and a standard curve was prepared with a cycle number of a standard sample at the fluorescence value 0.1235 as the vertical axis against a log value of concentration as the horizontal axis, and was used to calculate a sample concentration from the cycle number of the sample;

FIG. 9 shows real time PCR (gapdh) analysis. Data of real time PCR indicating the fluorescence value of each sample in the PCR cycle was analyzed by Fit Point Method of "Light-Cycler Software Ver. 3.5 (Roche)," and a standard curve was prepared with a cycle number of a standard sample at the fluorescence value 4.8276 as the vertical axis against a log value of concentration as the horizontal axis, and was used to calculate a sample concentration from the cycle number of the sample;

FIG. 10 shows expression levels of cloned genes. The expression level (M) was calculated from the sample concentration 10×(CO—CX) of each of the obtained genes by using a molecular weight of each PCR product, and was shown in graph form. Expression level (M)=10 (CO—CX)/PCR product MW;

FIG. 11 shows the isolation of promoter and terminator genes;

FIG. 12 shows inverse PCR products. Genomic DNA which was completely digested with a variety of restriction enzymes lacking a recognition sequence on each gene sequence and then self-ligated, was used as a template to perform inverse PCR using primers corresponding to each gene sequence, and the resulting PCR products were electrophoresed;

FIG. 13 shows the structure of the inverse PCR product. Bands obtained by inverse PCR were excised and incorporated into T-vectors. For determining the lengths of the obtained promoters and terminators, the positions of the enzymes used in the digestion of the respective samples were examined;

FIG. 14 shows the comparison of nucleotide sequences of actin promoters (SEQ ID NOS: 125-127). The homology between 500-bp actin promoter (KpnI) and actin promoter (EcoRI) was examined. Actin promoter (KpnI) AB200876;

FIG. 15 shows the construction of a transformation vector. A transfer plasmid was designed to have sacII as the only one site that could be used therein. A set of the promoter and terminator of each gene, a bleomycin resistance gene, and the 18S rRNA gene was cloned into pUC 18, which was in turn used as the transfer plasmid;

FIG. 16 shows the influence of a culture period on transformation efficiency. Cells of Labyrinthulomycota (CB15-5) (50 mM sucrose suspension) and linearized plasmids were added to a cuvette and subjected to electroporation under conditions of 500 V, 13Ω, 50 µF. The cells were seeded onto a medium containing 100 µg/ml Zeocin;

FIG. 17 shows the Zeocin resistance of the transformant. An 1-µl aliquot of the precultured microorganism cells was spotted onto GPY plate media having Zeocin concentration ranging from 0 to 6000 mg/ml and incubated at 28° C. for 48 hours in the shade;

FIG. 18 shows the detection of the bleomycin resistance protein gene. Genome of each of the obtained transformants was used as a template to perform PCR using bleomycin resistance gene-specific primers;

FIG. 19 shows the detection of the transgene at the 18S rRNA gene locus. For confirming that homologous recombination occurred at the 18S rRNA gene locus, primers corresponding to the downstream region of the 18S rRNA gene existing in only the genomic DNA and primers specific to the introduced bleomycin resistance gene were used to perform PCR; and FIG. 20 shows the construction of an expression vector. The ef1 promoter (300 bp), a rat elongase 2 gene, and the ef1 terminator (300 bp) were introduced into the SacI site of prGPZT, which was designated as prGPZT-EPELOT (7999 bp). As a negative control, the ef1 promoter and the ef1 terminator were introduced into the SacI site of prGPZT in the same way, which was designated as prGPZT-EPT (7210 bp).

BEST MODE FOR CARRYING OUT THE INVENTION

Hereinafter, the embodiments of the present invention will be described.

The vector used in the method for introducing a gene into labyrinthulomycota according to the present invention is a recombinant vector comprising a transgene and a nucleotide sequence which is homologous to a part of chromosomal DNA of Labyrinthulomycota and is capable of homologous recombination with the chromosomal DNA. An example of such a recombinant vector is a recombinant vector comprising at least (1) a nucleotide sequence which is homologous to a part of chromosomal DNA of Labyrinthulomycota and is capable of homologous recombination with the chromosomal DNA, (2) a selection marker gene having a promoter sequence located upstream and a terminator sequence located downstream, and (3) a transgene having a promoter sequence located upstream and a terminator sequence located downstream.

The nucleotide sequence used in the present invention which is homologous to a part of chromosomal DNA of Labyrinthulomycota and is capable of homologous recombination with the chromosomal DNA allows homologous recombination between the chromosomal DNA of Labyrinthulomycota and the nucleotide sequence, when introduced into a cell of Labyrinthulomycota. By this recombination, a transgene contained in the vector is incorporated into the chromosomal DNA of Labyrinthulomycota. Specific examples of such a nucleotide sequence which is homologous to a part of chromosomal DNA of Labyrinthulomycota can include an 18S rRNA gene sequence of Labyrinthulomycota. Specific examples thereof include a nucleotide sequence of 18S rRNA of *Schizochytrium* sp CB15-5 described in SEQ ID NO: 1. The 18S rRNA gene sequence can be obtained by a PCR method or the like using genomic DNA of *Schizochytrium* sp CB15-5 and suitable primers.

A gene exhibiting an appropriate phenotype by which a transformant having the vector used in the present invention can be selected can be used as the selection marker gene having a promoter sequence located upstream and a terminator sequence located downstream used in the present invention. For example, a drug resistance gene can be used as the selection marker gene. Specific examples of the drug resistance gene can include, but not limited to, a Zeocin (bleomycin) resistance gene. A promoter sequence and a terminator sequence are ligated upstream and downstream of the selection marker gene, respectively. Preferably, the promoter sequence and the terminator sequence used in the present invention are sequences that function in Labyrinthulomycota used as a host. It is preferred to use a promoter sequence and a terminator sequence derived from Labyrinthulomycota. Specific examples of the promoter and the terminator can include a promoter sequence and a terminator sequence of any of actin gene, elongation factor 1α(ef1α) gene, and glyceraldehyde 3-phosphate dehydrogenase (gapdh) gene.

The promoter sequences and the terminator sequences described above can be obtained by PCR using primer sequences designed on the basis of the information of nucleotide sequences described in SEQ ID NOs: 2 to 10 of Sequence Listing in the present specification, and genomic DNA of a cell of Labyrinthulomycota (e.g., *Schizochytrium* sp CB 15-5).

The vector used in the present invention has a transgene having a promoter sequence located upstream and a terminator sequence located downstream. By inserting a transgene into a cloning site (namely, a restriction enzyme site for inserting a transgene), a recombinant vector for the use in the method for introducing a gene according to the present invention can be constructed. In this context, the promoter sequence and the terminator sequence used are not particularly limited as long as they permit the expression of the gene of interest. A promoter sequence and a terminator sequence of any of actin gene, elongation factor 1α (ef1α) gene, and glyceraldehyde 3-phosphate dehydrogenase (gapdh) gene as described above may be used. Alternatively, a promoter sequence and a terminator sequence of the gene itself of interest that is used may be used.

For example, a pUC18 or prGPZT plasmid can be used as a backbone of the vector used in the present invention. These plasmids usually carry a replication origin (such as *E. coli* ori) and an antibiotic resistance gene (such as ampicillin resistance gene).

In the present invention, it is preferred to use a linearized vector. When a vector to be introduced is linearized by cleavage at a desired recombination site, homologous recombination occurs at the site. If a recombination site is not limited, a circular vector may be used for the transformation. Thus, the circular vector can be utilized in some applications.

The vector used in the present invention can be used by inserting a transgene into the cloning site. The type of the transgene is not particularly limited and can be selected according to purposes such as the application of a transformant to be produced. For example, a fatty acid synthase gene can be used as the transgene.

When a recombinant vector having a transgene is introduced into a cell of Labyrinthulomycota, a homologous recombination takes place between the nucleotide sequence contained in the recombinant vector which is homologous to a part of chromosomal DNA of Labyrinthulomycota and is capable of homologous recombination with the chromosomal DNA, and said chromosomal DNA. Thus, the transgene is introduced into a cell of Labyrinthulomycota. The transformation of the cell of Labyrinthulomycota could be accomplished for the first time by using the method for introducing a transgene according to the present invention.

The type of the cell of Labyrinthulomycota to which the gene transfer vector is introduced is not particularly limited. For example, a cell of the genus *Schizochytrium* or *Thraustochytrium* can be used. Specific examples of the cell of the genus *Schizochytrium* can include cells of *Schizochytrium aggregatum* ATCC 28209, *Schizochytrium limacinum* NIBH SR21, and *Schizochytrium* sp CB15-5 used in Example of the present specification. Specific examples of the cell of the genus *Thraustochytrium* can include cells of *Thraustochytrium aureum* ATCC 34304, *Thraustochytrium striatum* ATCC 24473, and an LFF1 strain of the genus *Thraus-*

*tochytrium* (Deposition No. FERM BP-08568 (transferred from FERM P-19159)) (JP Patent Publication (Kokai) No. 2005-102680A (2005)).

The LFF1 strain of the genus *Thraustochytrium* (JP Patent Publication (Kokai) No. 2005-102680A (2005)) can also be selected according to, for example, a screening method as described below. At first, the microorganisms are harvested by filtrating collected sea water through a 0.4-μm sterilized filter. This filter is attached onto an agar medium composed of 90% natural sea water, glucose, yeast extracts, and peptone, followed by culture at 20 to 30° C. Colonies formed on this filter of the agar plate medium are cultured on an agar medium of the same composition as above, and the obtained microorganism cells are collected with a spatula. Fatty acids are methyl-esterified directly from the cells according to a routine method, and the composition thereof is analyzed by gas chromatography to select a strain that produces docosahexaenoic acid. Furthermore, a strain that accumulates in the cell 10% or more by weight, preferably 20% or more by weight, of fats and oils relative to dried cell weight, and/or contains in fats and oils 10% or less of by weight of docosapentaenoic acid and 30% or more by weight of docosahexaenoic acid relative to the total amount of fatty acids can be selected.

The *Schizochytrium* sp CB15-5 has properties almost equal to those of the LFF 1 strain of the genus *Thraustochytrium*, and can be handled in a similar way.

The transformation of Labyrinthulomycota with the method for introducing a transgene according to the present invention can be performed by electroporation, a gene gun, the drug treatment of the cell membrane, calcium phosphate transfection, or DEAE-dextran-mediated transfection, or the like. Preferably, the transformation can be performed by electroporation.

From a transformation efficiency standpoint, it is preferred that the recombinant vector of the present invention comprising the transgene should be introduced into a cell of Labyrinthulomycota collected from a culture medium that has reached stationary phase. For example, a strain that reaches stationary phase in approximately 2 days is used in Example of the present specification. In this case, it is preferred that the recombinant vector of the present invention comprising the transgene should be introduced into a cell of Labyrinthulomycota cultured for 3 to 4 days.

A transformant can be selected by using the expression of the selection marker gene contained in the vector as an index. For example, when a drug resistance gene is used as the selection marker, only the transformant having the selection marker can be selected and obtained by culturing transformants in a medium containing the corresponding drug.

Any of those known in the art can be used as the medium for the culture of the transformant. Examples of a carbon source used in the medium can include: carbohydrate such as glucose, fructose, saccharose, and starch: fats and oils such as oleic acid and soybean oil; and glycerol and sodium acetate. These carbon sources can be used at a concentration of, for example, 20 to 300 g per litter of the medium. According to a particularly preferable aspect, the transformant can be cultured in two media having different carbon source concentrations, for example, in a medium having a carbon source concentration from 4% to 7% inclusive and subsequently in a medium having a carbon source concentration from 13% to 20% inclusive. Culture under such conditions allows increase in the amount of fats and oils produced, in some cases.

Moreover, organic nitrogen such as yeast extracts, corn steep liquor, polypeptone, sodium glutamate, and urea, or inorganic nitrogen such as ammonium acetate, ammonium sulfate, ammonium chloride, sodium nitrate, and ammonium nitrate can be used as a nitrogen source. Potassium phosphate and the like can be combined appropriately and used as an inorganic salt.

When the promotion of production of docosahexaenoic acid is intended, a precursor of docosahexaenoic acid can be added to the medium. Examples of the precursor can include, but not limited to, hydrocarbons such as tetradecane, hexadecane, and octadecane, fatty acids such as tetradecanoic acid, hexadecanoic acid, octadecanoic acid, and oleic acid or salts thereof (e.g., sodium salts or potassium salts), and fatty acid esters or fats and oils containing fatty acids as a component (e.g., olive oil, soybean oil, cottonseed oil, and coconut oil).

It is preferred that the prepared medium should be used after pH is adjusted to within the range of 4.0 to 9.5 by adding an appropriate acid or base, and subsequent sterilization with an autoclave is done.

A culture temperature for the microorganism is generally 10 to 45° C., preferably 20 to 37° C. Preferably, the culture temperature is controlled to a culture temperature capable of producing of a desired fats and oils composition. pH during the culture is generally 3.5 to 9.5, preferably 4.5 to 9.5. Particularly preferable pH differs depending on purposes.

A culture period can be, for example, 3 to 7 days, and the microorganism can be cultured by aerobic stirring culture, shake culture, or static culture.

In this way, microorganism cells that have accumulated high concentrations of desired lipids or fatty acids in the cultured product can be obtained. The culture medium and the microorganism cells can be separated from the cultured product by a routine method known by those skilled in the art. For example, the separation can be performed by a centrifugation, filtration, or the like, and the centrifugation is particularly preferable.

The microorganism cells separated from the cultured product can be disrupted using, for example, sonication or Dynomill, and then subjected to solvent extraction with chloroform, hexane, butanol, or the like to obtain the desired lipids and fatty acids.

Hereinafter, the present invention will be described more fully with reference to Example. However, the present invention is not intended to be limited to Example.

EXAMPLE

Figure 1:
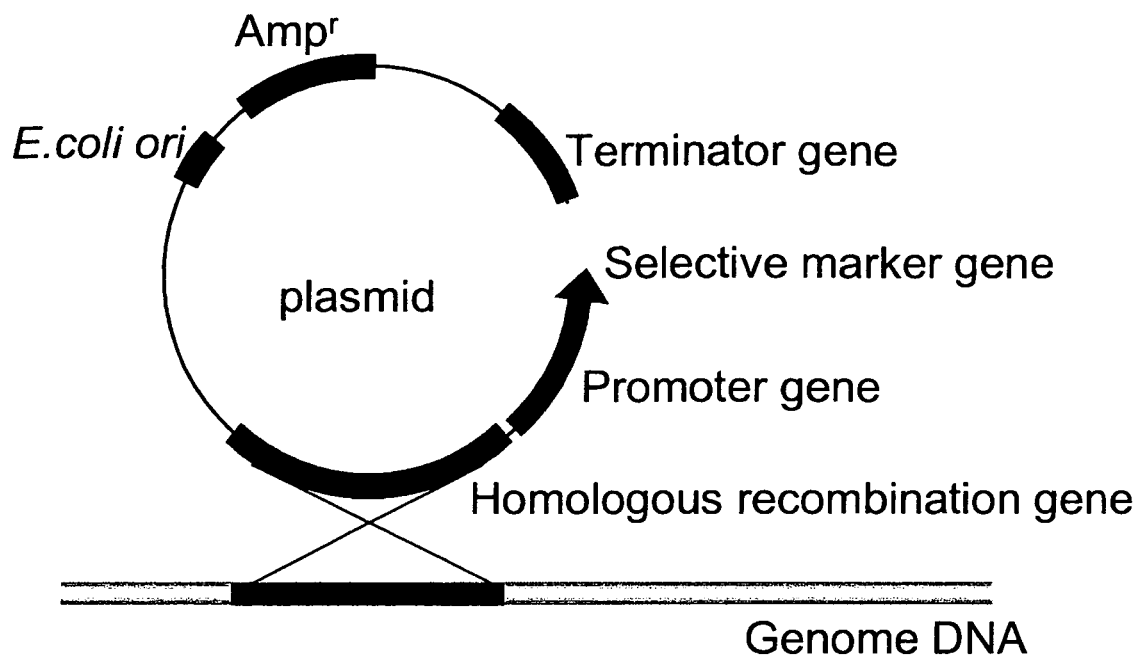
FIG. 1 shows a schematic diagram of homologous recombination with a plasmid having a gene homologous to genome.

In this Example, *Schizochytrium* sp. CB15-5 having high proliferation and lipid accumulation properties was used as a model host. Gene transfer by homologous recombination was performed for stably maintaining a transgene. A transfer plasmid having a promoter working with reliability and a selection marker gene was first prepared to investigate a gene transfer method (FIG. 1).

(A) Materials and Method (1) Strain Used

CB 15-5 strain of the genus Schizochytrium (2) Culture of Microorganism Cells

GPY medium (pH 7.4)

3.0% D-Glucose 1.5% Polypeptone 0.5% Yeast Extract 50.0% Sea water

GPYS medium (pH 7.4)

3.0% D-Glucose 0.6% Polypeptone 0.2% Yeast Extract 50.0% Sea water 50 mM sucrose Shaking incubator: Bio-Shaker BR-300 CF (TAITEC)

Temperature: 28° C.

Shaking speed: 170 min-1

Preculture time: 1 day

Main culture time: 1 to 4 days

Culture temperature: 28° C.

(3) Test for Zeocin Sensitivity of CB15-5 Strain

The precultured microorganism cells were diluted 1000-fold, and 100 μL thereof was seeded onto GYP plate media having Zeocin concentration ranging from 0 to 50 μg/ml, and incubated at 28° C. for 72 hours in the shade. The number and size of the resulting colonies were measured.

(4) Genomic DNA Extraction from Labyrinthulomycota

Following main culture for 1 day, 5 ml of the microorganism cells was placed into a 15-ml Falcon tube and harvested by centrifugation. The cells were washed with cold PBS and then added with 5 ml of TNE buffer (10 mM Tris-HCl (pH 7.5)+0.1 M NaCl+0.1 mM EDTA), followed by suspension by vortex. Next, the resulting suspension was added with 50 μl of 10% SDS (already filter-sterilized) and 25 μl of 20 mg/ml Proteinase K and mildly stirred by inversion by hand. This solution was placed into a constant temperature bath at 60° C. and left for 2 hours. After the addition of an equal quantity of phenol (supplemented with 8-hydroxyquinoline and equilibrated with 1 M Tris-HCl to pH 8.0), the resulting mixture was mildly stirred by inversion for 20 minutes and then centrifuged at 3000 rpm for 15 minutes. The supernatant was placed into a new Falcon tube using a truncated chip and added with an equal quantity of phenol:chroloform:isoamyl alcohol (25:24:1). The resulting mixture was mildly stirred by inversion for 20 minutes and then centrifuged at 3000 rpm for 15 minutes. The supernatant was placed in small quantities into 1.5-ml microtubes, each of which was added with an equal quantity of cold isopropanol. The resulting mixtures were mildly stirred by inversion and then centrifuged at 15000 rpm for 15 minutes. The supernatant was discarded, and the pellet was added with 500 μl of 70% cold ethanol and centrifuged at 15000 rpm for 5 minutes. The supernatant was discarded, and the pellet of DNA was dried in speed vac for 5 minutes. 200 μl of TE buffer (10 mM Tris-HCl (pH 7.5)+1 mM EDTA) was added to dissolve the DNA, 2.5 μl of RNase (1 mg/ml) solution was then added and reaction was performed at 37° C. for 1 hour. The solutions in all of the tubes were put together into one tube. An equal quantity of phenol:chroloform:isoamyl alcohol (25:24:1) was then added to the tube, and the mixture was mildly stirred by inversion for 5 minutes and then centrifuged at 15000 rpm for 5 minutes. This procedure was repeated twice. The supernatant was transferred to a 1.5-ml microtube, to which 40 μl (1/10 volume) of 3 M sodium acetate and an equal quantity (1 ml) of cold ethanol were then added. The resulting mixture was mildly stirred by inversion and then centrifuged at 15000 rpm for 10 minutes. The supernatant was discarded, and the pellet was supplemented with 700 μl of 70% cold ethanol and centrifuged at 15000 rpm for 5 minutes. The supernatant was discarded, and the pellet of DNA was dried in speed vac for 5 minutes. 200 μl of TE buffer was added to dissolve the DNA and the mixture was stored at −20° C.

(5) Isolation of 18S rRNA Gene by PCR Method

PCR conditions primers 18S1 and 18S12 0.5 μM each genomic DNA 500 ng

10×Ex taq buffer 5 μl dNTP 0.2 mM

Ex taq (5 units/μl) 0.25 μl sterile water q.s.

Total 50.0 μl

Thermal Cycler

95° C. for 5 minutes, followed by 35 cycles (95° C. for 30 seconds, 55° C. for 30 seconds, and 72° C. for 1 minute)

(6) Purification of PCR Product

The PCR product was purified using a PCR purification kit "Marligen Rapid PCR Purification System (Marligen)."

(7) Cloning

Ligation

Vector 5 ng

Insert DNA 5 ng to 50 ng

2× Rapid ligation buffer 5.0 μl

T4 DNA Ligase (3 units/μl) 1.0 μl sterile water q.s.

Total 10.0 μl

↓

At 16° C. overnight

Transformation

After ligation, 10 μl of the DNA solution was added with 100 μl of competent cells, then cooled on ice for 5 minutes, and incubated (heat shock) at 37° C. for 3 minutes. The resulting solution was immediately put back on ice and left for 5 minutes. This microorganism cell suspension was seeded and cultured at 37° C. for 12 hours on an LB medium (containing 50 μg/ml ampicillin) over which 40 μl of IPTG (100 mM) and 40 μl of X-gal (20 mg/ml) were spread in advance.

(8) Plasmid Extraction

A plasmid was extracted according to the protocol of a plasmid extraction kit "Marligen Rapid Plasmid System (Marligen)."

(9) Protocol of Sequence Reaction

Sequence reaction was performed according to the protocols of "DYEnamic ET Terminator Cycle Sequencing Kit (Amersham Biosciences)" and "AutoSeq G-50 (Amersham Biosciences)." Sequence analysis was performed with "ABI PRISM® 310 Genetic Analyzer (Biosystem)" according to the operating guide.

Oligonucleotide Primers Used in Amplification and Sequencing

Primer Sequence (5'-3')

| 18S-1 | CCAACCTGGTTGATCCTGCCAGTA | (SEQ ID NO: 11) |
|---|---|---|
| 18S-2 | CATTCAAGTTTCTGCCCTATC | (SEQ ID NO: 12) |
| 18S-3 | CAGGCTCCCTCTCCGGAATC | (SEQ ID NO: 13) |
| 18S-4 | GCAGCCGCGGTAATTCCAGC | (SEQ ID NO: 14) |
| 18S-5 | ACTACGAGCTTTTTAACTGG | (SEQ ID NO: 15) |
| 18S-6 | GTCAGAGGTGAAATTCTTGG | (SEQ ID NO: 16) |
| 18S-7 | TCCTTGGTAAATGCTTTCGC | (SEQ ID NO: 17) |
| 18S-8 | GGATTGACAGATTGAGAGCT | (SEQ ID NO: 18) |
| 18S-9 | AACTAAGAACGGCCATGCACC | (SEQ ID NO: 19) |
| 18S-10 | AGGTCTGTGATGCCCTTAGA | (SEQ ID NO: 20) |
| 18S-11 | CGTTTACTAGGAATTCCTCG | (SEQ ID NO: 21) |
| 18S-12 | CCTTGTTACGACTTCACCTTCCTCT | (SEQ ID NO: 22) |

(10) Phylogenetic Analysis

A phylogenetic tree was prepared using a neighbor-joining (NJ) method (Saitou and Nei, 1987) and a maximum-likelihood (ML) method (Felsenstein, 1981). The NJ analysis was conducted using PAUP version 4.0d64 (Swofford, 1998). The distance was estimated by an ML method using Felsenstein's (1984) (F84) model.

(11) Inverse PCR of 18S rRNA Gene

An enzyme that was not seen in the gene sequence was selected, and the genome was completely digested with the enzyme. Next, Ligase was added to the sample to allow reaction to prepare self ligation genome. The self ligation genome was used as a template to perform PCR using reverse primers specific to the gene.

Selected restriction enzyme: NheI

PCR conditions primers 18SF3 and 18SR3 0.5 µM each self ligation genomic DNA 100 ng 10×La PCR buffer 5 µl dNTP 0.4 mM $MgCl_2$ 2.5 mM La taq (5 units/µl) 0.5 µl sterile water q.s.

Total 50.0 µl

Thermal Cycler

94° C. for 2 minutes, followed by 25 cycles (94° C. for 20 seconds, 68° C. for minutes, and 72° C. for 10 minutes)

Oligonucleotide Primers Used in Amplification and Sequencing

Primer Sequence (5'-3')

| 18SF | TACACTGATGGGTTCATCGG | (SEQ ID NO: 23) |
|---|---|---|
| 18SR | CCCGTTATAGTCACCGTAGT | (SEQ ID NO: 24) |

(12) Gel Extraction

The PCR product was purified using a gel extraction kit "Marligen Rapid Gel Extraction System (Marligen)."

(13) Total RNA Extraction from Labyrinthulomycota

After main culture for 1 day, the microorganism cells (1 to 5 g) were harvested, then added with an appropriate amount of liquid nitrogen and 5 ml of Trizol (GIBCO), and pulverized into powder with quartz sand. To the powder, 5 ml of Trizol kept at 60° C. was added, and the mixture was stirred for 30 seconds by vortex and incubated at 60° C. for 15 minutes. Following centrifugation (14000 rpm, 15 min., 4° C.), 1-ml aliquots of the supernatant were dispensed into 1.5-ml microtubes. To each of the tubes, 200 µl of chloroform was added, and the mixture was incubated at room temperature for 5 minutes and then vigorously stirred by vortex until the solution became an emulsion. Following centrifugation (14000 rpm, 15 min., 4° C.), the upper layer of 2 separated layers was collected into another microtube, to which 500 µl of isopropanol was then added. The microtube was left undisturbed at room temperature for 10 minutes and centrifuged (14000 rpm, 10 min., 4° C.). The supernatant was discarded, and the remaining pellet was added with 300 µl of 4 M ice-cold LiCl and dissolved by pipetting, followed by centrifugation (6500 rpm, 10 min., RT). The supernatant was discarded, and the pellet was added with 200 µl of 0.5% SDS-TE buffer and 200 µl of chloroform and stirred by vortex, followed by centrifugation (6500 rpm, 5 min., RT). The upper aqueous layer was collected into another microtube, to which a ¹⁄₁₀ amount of 3 M sodium acetate and a 2.5-fold amount of ethanol were then added. The mixture was left undisturbed for 5 minutes and centrifuged (14000 rpm, 10 min., 4° C.). The supernatant was discarded, and the precipitated RNA was rinsed with 75% ethanol and dried in air. The resulting RNA was dissolved in DEPC-treated water and used as a total RNA sample.

(14) cDNA synthesis cDNA synthesis was performed according to the protocol of "3' RACE System for Rapid Amplification of cDNA Ends (Invitrogen)."

(15) Isolation of Each Gene of Actin, Elongation Factor 1α, and gapdh by PCR Method PCR Conditions primers for actin (a2 and a6), for ef1α (ef2 and ef5), and for gapdh (g1 and g4) 0.5 µM each cDNA 50 ng 10×La PCR buffer 5 µl dNTP 0.4 mM $MgCl_2$ 2.5 mM La taq (5 units/µl) 0.5 µl sterile water q.s.

Total 50.0 µl

Thermal Cycler

94° C. for 2 minutes, followed by 30 cycles (94° C. for 20 seconds, 64° C. for 5 minutes, and 72° C. for 10 minutes)

Oligonucleotide Primers Used in Amplification and Sequencing

Primer Sequence (5'-3')

| a2 | GCTCCTCGCGCTGTGTTCCC | (SEQ ID NO: 25) |
|---|---|---|
| a6 | GAAGCACTTGCGGTGGACAAT | (SEQ ID NO: 26) |

-continued

| | | |
|---|---|---|
| ef2 | ACCACCACTGGTCACCTGAT | (SEQ ID NO: 27) |
| ef5 | ACGTTGAAGCCCACGTTGTC | (SEQ ID NO: 28) |
| gap1 | GGTATCAACGGCTTTGGCCGCA | (SEQ ID NO: 29) |
| gap4 | ACCTTGCCCACAGCCTTGGC | (SEQ ID NO: 30) |

(16) 3' RASE, Each Gene of Actin, Elongation Factor 1α, and gapdh

3' RASE PCR was performed according to the protocol of "3' RACE System for Rapid Amplification of cDNA Ends (Invitrogen)."

GSP1-primers: actin (a1), ef1α (ef2), and gapdh (gap2)

GSP2-primers: actin (AF), ef1α (EF), and gapdh (GF)

Oligonucleotide Primers Used in Amplification and Sequencing

Primer Sequence (5'-3')

| | | |
|---|---|---|
| a1 | GACAACGGTTCCGGTATGTGC | (SEQ ID NO: 31) |
| AF | GGTTATCATGGTCGGCATGG | (SEQ ID NO: 32) |
| ef2 | ACCACCACTGGTCACCTGAT | (SEQ ID NO: 33) |
| EF | CTCAAGGCCGAGCGTGAGCG | (SEQ ID NO: 34) |
| gap2 | AACGGCTTTGGCCGCATCGGTCG | (SEQ ID NO: 35) |
| GF | GCCTCCTGCACCACTAACTG | (SEQ ID NO: 36) |

(17) 5' RASE, Each Gene of Actin, Elongation Factor 1α, and gapdh

5' RACE PCR was performed according to the protocol of "5' RACE System, Version 2.0 (Invitrogen)."

GSP1-primers: actin (a8), ef1α (ef7), and gapdh (gap4)

GSP2-primers: actin (AR), ef1α (e9), and gapdh (GR)

GSP3-primers: actin (a11), ef1α (ER), and gapdh (g8)

Oligonucleotide Primers Used in Amplification and Sequencing

Primer Sequence (5'-3')

| | | |
|---|---|---|
| a8 | AGCGAGGCGCATCTCCTCGT | (SEQ ID NO: 37) |
| AR | ACGCGGAGCTCGTTGTAGAA | (SEQ ID NO: 38) |
| a11 | GGTCACGATACCGTGCTCAA | (SEQ ID NO: 39) |
| ef7 | GTACTCAGTGAAGGACTCAACG | (SEQ ID NO: 40) |
| e9 | CGTAGCCAGCGCGGATCTCA | (SEQ ID NO: 41) |
| ER | GGCAACATCGGCCTGGGAGG | (SEQ ID NO: 42) |
| gap4 | ACCTTGCCCACAGCCTTGGC | (SEQ ID NO: 43) |
| GR | CCAGCACGCCAGTCCTTTCC | (SEQ ID NO: 44) |
| g8 | CCATCCTTGATCTCAATAGT | (SEQ ID NO: 45) |

(18) Confirmation of Expression of Each Gene of Actin, ef1α, and gapdh by Real Time PCR Method (i) Preparation of Standard Sample for Standard Curve The fragment amplified by a PCR method using primers specific to each gene was gel-extracted, and its concentration was measured with an absorbance reader to prepare 1 μg/ml standard sample. Dilution series of $1\times10^{-3}$ to $10^6$ μg/ml were prepared for each of the samples and used in experiments.

PCR Conditions primers: actin (a7 and a8), ef1α (e8 and e9), and gapdh (g7 and g8) 0.5 μM each cDNA 100 ng 10×Ex taq buffer 5 μl dNTP 0.2 mM Ex taq (5 units/μl) 0.25 μl sterile water q.s.

Total 50.0 μl

Thermal Cycler

94° C. for 2 minutes, followed by 30 cycles (94° C. for 30 seconds, 57° C. for 30 seconds, and 72° C. for 30 seconds)

(ii) Preparation of cDNA Sample cDNA (0.2 μg/ml) was synthesized from 4.5 μg of the total RNA with SuperScript II, and the sample was designated as CO. In consideration of the contamination of the genome, a sample was prepared by the same procedure except that sterile water was used instead of SuperScript II, and this sample was designated as CX. Each of the samples was diluted 10-fold and used in experiments.

(iii) Real Time PCR

The standard samples and the cDNA samples were subjected to real time PCR according to the protocol of "Light-Cycler-FastStart DNA Master SYBR Green I (Roche)."

PCR Conditions primers: actin (a7 and a8), ef1α (e8 and e9), and gapdh (g7 and g8) 0.5 μM each CO and CX standard samples 2 μl each $MgCl_2$ Stock Sol. 1.6 μl LD-DNA Master Sybr Green 2 μl sterile water q.s.

Total 20.0 μl

CO=cDNA (0.02 μg/ml)

$S10^{-3}$=standard ($1\times10^{-3}$ μg/ml)

$S10^{-4}$=standard ($1\times10^{-4}$ μg/ml)

$S10^{-5}$=standard ($1\times10^{-5}$ μg/ml)

$S10^{-6}$=standard ($1\times10^{-6}$ μg/ml)

Thermal Cycler

95° C. for 10 minutes (denaturation)

↓

95° C. for 10 seconds (PCR)

65° C. (actin), 60° C. (ef1), 63° C. (gapdh) for 5 seconds

72° C. for 10 seconds

87° C. (actin), 84° C. (ef1), 88° C. (gapdh) for 1 second (33 cycles)

↓

95° C. for 0 second (melting)

70° C. (actin), 65° C. (ef1), 68° C. (gapdh) for 15 seconds

95° C. for 0 second

Oligonucleotide Primers Used in Amplification

Primer Sequence (5'-3')

| | | |
|---|---|---|
| a7 | GGCCGTGACCTCACTGACTA<br>(real time PCR of actin) | (SEQ ID NO: 46) |
| a8 | AGCGAGGCGCATCTCCTCGT<br>(real time PCR of actin) | (SEQ ID NO: 47) |
| e8 | TTGGCTTCAACGTCAAGAAC<br>(real time PCR of ef1α) | (SEQ ID NO: 48) |
| e9 | CGTAGCCAGCGCGGATCTCA<br>(real time PCR of ef1α) | (SEQ ID NO: 49) |
| g7 | GACGCCTCGTGTTCCGCACG<br>(real time PCR of gapdh) | (SEQ ID NO: 50) |
| g8 | CCATCCTTGATCTCAATAGT<br>(real time PCR of gapdh) | (SEQ ID NO: 51) |

(19) Acquisition of Promoter and Terminator of Each Gene of Actin, ef1α, and gapdh by inverse PCR Method An enzyme that was not seen in the gene sequence was selected, and the genome was completely digested with the enzyme. Next, Ligase was added to the sample to allow reaction to prepare self ligation genome. The self ligation genome was used as a template to perform PCR using reverse primers specific to the gene.

Selected enzymes: actin (KpnI, NheI, and EcoRI), ef1α (HindIII, NheI, and EcoRI), gapdh (KpnI, HindIII, and NheI)

PCR Conditions primers: actin (a9 and AR), ef1α (e10 and ER), and gapdh (g9 and g8) 0.5 μM each An enzyme used was La Taq, and PCR was performed under the same conditions as in the protocol for the 18S rRNA gene.

Oligonucleotide Primers Used in Amplification and Sequencing

Primer Sequence (5'-3')

| | | |
|---|---|---|
| a9 | ATCTCCAAGCAGGAGTACGA<br>(Inverse PCR of actin) | (SEQ ID NO: 52) |
| AR | ACGCGGAGCTCGTTGTAGAA<br>(Inverse PCR of actin) | (SEQ ID NO: 53) |
| e10 | GGTGTCATCAAGGAGGTTGA<br>(Inverse PCR of ef1α) | (SEQ ID NO: 54) |
| ER | GGCAACATCGGCCTGGGAGG<br>(Inverse PCR of ef1α) | (SEQ ID NO: 55) |
| g9 | CTCATCAGCTGGTACGATAA<br>(Inverse PCR of gapdh) | (SEQ ID NO: 56) |
| g8 | CCATCCTTGATCTCAATAGT<br>(Inverse PCR of gapdh) | (SEQ ID NO: 57) |
| a12 | TGAACTTCGTCGTCAGCCAT<br>(sequencing of actin) | (SEQ ID NO: 58) |
| a13 | TCCACCGCAAGTGCTTCTAA<br>(sequencing of actin) | (SEQ ID NO: 59) |
| ae14 | TGTGCGTCTAGTCCAACCTT<br>(sequencing of actin) | (SEQ ID NO: 60) |
| ak14 | TTGGAAGACGCTCCTAGTAG<br>(sequencing of actin) | (SEQ ID NO: 61) |
| ak15 | GACTTCAACTATGTCCAGGC<br>(sequencing of actin) | (SEQ ID NO: 62) |
| ak16 | GTAGTCAGAGGTACTGAGTT<br>(sequencing of actin) | (SEQ ID NO: 63) |
| ak17-2 | CATGTGGTTATGTAGAACGCA<br>(sequencing of actin) | (SEQ ID NO: 64) |
| ak18 | AGTATCTCGTGAAAGCGGGA<br>(sequencing of actin) | (SEQ ID NO: 65) |
| e12 | TGCTCCTTCGTCTTGCCCAT<br>(sequencing of ef1α) | (SEQ ID NO: 66) |
| e13 | TATGAAGCTAGGATGTGCGT<br>(sequencing of ef1α) | (SEQ ID NO: 67) |
| e14 | CACCTACCTTGGCTCCTCGT<br>(sequencing of ef1α) | (SEQ ID NO: 68) |
| e15 | CGATATCGCAACTGTGTCGA<br>(sequencing of ef1α) | (SEQ ID NO: 69) |
| en16 | GAAAACGTTGGAGAGCCTGA<br>(sequencing of ef1α) | (SEQ ID NO: 70) |
| e17 | ACAGTGACGGTATCTCTGCT<br>(sequencing of ef1α) | (SEQ ID NO: 71) |
| en18 | ACCGTAACGGCCATAAGAAG<br>(sequencing of ef1α) | (SEQ ID NO: 72) |
| g12 | ATAGGTGCGTCGGCAGACAT<br>(sequencing of gapdh) | (SEQ ID NO: 73) |
| g13 | TAAGCACTGAAGAAGCGAGT<br>(sequencing of gapdh) | (SEQ ID NO: 74) |
| g14 | CGTACCAGTCGGAACCTCTG<br>(sequencing of gapdh) | (SEQ ID NO: 75) |
| g15 | CTTAGGGCTCATCGTCAACA<br>(sequencing of gapdh) | (SEQ ID NO: 76) |
| gh16 | ACAGCACGCCTTACTTACCT<br>(sequencing of gapdh) | (SEQ ID NO: 77) |
| g17 | CCTTCAATCCTAAACACCATGC<br>(sequencing of gapdh) | (SEQ ID NO: 78) |
| gh18 | TGAGGAGAACTGCAAGCACC<br>(sequencing of gapdh) | (SEQ ID NO: 79) |

(20) Construction of Transfer Plasmid (i) Preparation of Insert

Each fragment was amplified by PCR, then gel-extracted, and its concentration was measured. A terminator of each gene was digested with SalI and SphI and purified with a PCR purification kit. The 18S rRNA gene was subcloned once into a pUC18 plasmid, and the purified plasmid was digested with KpnI and gel-extracted.

PCR Conditions for Promoter, Terminator, and 18S rRNA Gene

Primers:

actin promoter (pAF and zAR)

ef1α promoter (pEF and zER)

gapdh promoter (pGF and zGR)

actin terminator (salAF and sphAR)

ef1α terminator (salEF and sphER)

gapdh terminator (salGF and sphGR), and 18S rRNA gene (kpn 18rF and kpn 18rR) 50 pmol each genomic DNA 100 ng buffer#1 5 µl dNTP 0.2 mM MgCl$_2$ 1 mM KOD DNA polymerase 2.5 U sterile water q.s.

Total 50.0 µl

PCR conditions for bleomycin resistance protein gene primers actin (aZF and pZR)

ef1α (eZF and pZR), and gapdh (gZF and pZR) 50 pmol each pPhaT1 20 ng buffer#1 5 µl dNTP 0.2 mM MgCl$_2$ 1 mM KOD DNA polymerase 2.5 U sterile water q.s.

Total 50.0 µl

Thermal Cycler for Promoter and 18S rRNA gene 25 cycles (98° C. for 15 seconds, 63° C. (promoter) or 65° C. (18S rRNA) for 2 seconds, and 74° C. for 30 seconds)

Thermal Cycler for Terminator and Bleomycin Resistance Protein Gene 25 cycles (98° C. for 15 seconds and 68° C. for 30 seconds)

Oligonucleotide Primers Used in Amplification and Sequencing

Primer Sequence (5'-3')

| | | |
|---|---|---|
| pAF | TCGAGCTCGGTACCCCTTCATACTCTCGCATTTCC | (SEQ ID NO: 80) |
| zAR | TTGGCCATTTTGCTAGTTGGGTGCTTGTTCTT | (SEQ ID NO: 81) |
| pEF | TCGAGCTCGGTACCCTCATGCTCCTTTCCCGCCAA | (SEQ ID NO: 82) |
| zER | TTGGCCATTTTGTTTGGTGCTAGTAGCTTCGA | (SEQ ID NO: 83) |
| pGF | TCGAGCTCGGTACCCTTGATCTTGTGAGGGCTCCA | (SEQ ID NO: 84) |
| zGR | TTGGCCATTTTGCTTGGTGTTTATGTGTGCGC | (SEQ ID NO: 85) |
| aZF | CTAGCAAAATGGCCAAGTTGACCAGTGCCGTT | (SEQ ID NO: 86) |
| eZF | CAAACAAAATGGCCAAGTTGACCAGTGCCGTT | (SEQ ID NO: 87) |
| gZF | CAAGCAAAATGGCCAAGTTGACCAGTGCCGTT | (SEQ ID NO: 88) |
| pZR | CTCTAGAGGATCCCCTCAGTCCTGCTCCTCGGCCA | (SEQ ID NO: 89) |
| salAF | AGAGTCGACATTGGAGTGATGGAATGCCC | (SEQ ID NO: 90) |
| sphAR | CTTGCATGCTGTTGAAAGAGCTGAGGCCA | (SEQ ID NO: 91) |
| salEF | AGAGTCGACGTGGTTTGACCTCTTATACT | (SEQ ID NO: 92) |
| sphER | CTTGCATGCGTTTCCCAACTCACGTTGTG | (SEQ ID NO: 93) |
| salGF | AGAGTCGACATGTACCCAATACCACACCG | (SEQ ID NO: 94) |
| sphGR | CTTGCATGCCTTGAAGCACTAGAAGAGCA | (SEQ ID NO: 95) |
| kpn18rF | CGGGGTACCCCAGTAGTCATATGCTCGTC | (SEQ ID NO: 96) |
| kpn18rR | CGGGGTACCCCTTGTTACGACTTCACCTT | (SEQ ID NO: 97) |

(ii) Workflow (a) The pUC18 was digested with SmaI, then gel-extracted, and its concentration was measured. Each gene promoter and the bleomycin resistance protein gene were introduced into the SmaI site of the pUC18 using Fusion Enzyme according to the protocol of "BD In-Fusion™ Dry-Down PCR Cloning Kit (BD Biosciences)." Next, the absence of mutation in the bleomycin resistance protein gene was confirmed by sequencing.

(b) The plasmids (pAPZ (4568 bp), pEPZ (4547 bp), and pGPZ (4418 bp)) having each gene promoter and the bleomycin resistance protein gene constructed in the step (a) were digested with SalI and SphI and then gel-extracted. The terminators corresponding to the promoters were respectively introduced into the plasmids using Ligase.

(c) The plasmids (pAPZT (5562 bp), pEPZT (5545 bp), and pGPZT (5396 bp)) having each gene promoter, the bleomycin resistance protein gene, and the terminator constructed in the step (b) were digested with KpnI and then gel-extracted. The 18S rRNA gene was introduced into the plasmids using Ligase to prepare three transfer plasmids designated as prAPZT (5562 bp) <actin promoter>, prEPZT (5545 bp) <ef1α promoter>, and prGPZT (5396 bp) <gapdh promoter> (FIG. 15).

(21) Gene Transfer by Electroporation Method (i) Preparation of Plasmid

Plasmids were extracted in large quantities according to the protocol of a high-speed plasmid large scale (midi) purification system "PureYield™ Plasmid Midiprep System (Promega)", and their concentrations was measured by absorptiometer. The linear plasmid samples were digested with SacII. The samples (10 µg) were concentrated with Ethachinmate (NIPPON GENE) and dissolved in 10 µl of sterile water.

(ii) Preparation of Cell (5 µm or Less)

The main culture medium was put through a filter (5 µm (MILLIPORE)) and centrifuged (12000 g, 5 min., 4° C.). The supernatant was discarded, and the pellet was added with BSS buffer (10 mM KCl, 10 mM NaCl, and 3 mM $CaCl_2$) and centrifuged (12000 g, 5 min., 4° C.). The supernatant was discarded. Next, the pellet was added with 50 mM sucrose and centrifuged (12000 g, 5 min., 4° C.), and the supernatant was discarded. This procedure was performed twice. The cells were counted using a hemocytometer. In the last stage, the cells were suspended at $4\times10^7$ cells/80 µl in 50 mM sucrose.

(iii) Preparation of Cell

The main culture medium was placed into a 1.5-ml microtube and centrifuged (12000 g, 5 min., 4° C.). The supernatant was discarded, and the pellet was added with BSS buffer and centrifuged (12000 g, 5 min., 4° C.). The supernatant was discarded. Next, the pellet was added with 50 mM sucrose and centrifuged (12000 g, 5 min., 4° C.), and the supernatant was discarded. This procedure was performed twice. In the last stage, 50 mM sucrose was added to the cells to adjust the total amount thereof to 100 µl, and the cells were suspended by vortex.

(iv) Transformation

An 80-µl aliquot of the prepared cells was mixed with 10 µl of the plasmids. The resulting mixture was placed in a cooled cuvette (2 mm gap (BM Equipment)) and incubated on ice for 5 minutes. Next, the cuvette was loaded in an electroporation apparatus (ECM600 (BTX)) and pulsed once under each condition of 200 V, 500 V, 1500 V, and 2500 V (50 µF, 13Ω). Then, 1 ml of GPYS liquid medium was added thereto, and the mixture was transferred to an Eppendorf tube and incubated in water bath at 28° C. for 1 hour. After centrifugation (12000 g, 5 min., RT), the supernatant was discarded to adjust the total amount thereof to 100 µl, followed by vortex. The resulting product was seeded onto a GPYS medium containing 100 µg/ml Zeocin and cultured at 28° C. for 2 days.

(22) Test for Zeocin Sensitivity of Transformant

The precultured microorganism cells were diluted to 20 cells/µl, and 1 µl thereof was spotted onto GPY plate media having Zeocin concentration ranging from 0 to 6000 µg/ml and incubated in the shade at 28° C. for 60 hours.

(23) Confirmation of Transgene by PCR Method

PCR Conditions primers 0.5 µM each genomic DNA 500 ng

10×Ex taq buffer 5 µl dNTP 0.2 mM

Ex taq (5 units/µl) 0.25 µl sterile water q.s.

Total 50.0 µl

Thermal Cycler

94° C. for 2 minutes, followed by 30 cycles (94° C. for 30 seconds, 68° C. for 30 seconds, and 72° C. for 30 seconds)

Oligonucleotide Primers Used in Amplification

Primer Sequence (5'-3')

```
ZEOF    TACCGGTTCAACTGGTCACGGC    (SEQ ID NO: 98)
ZEOR    TCAGTCCTGCTCCTCTTCCA     (SEQ ID NO: 99)
```

(24) Confirmation of Homologous Recombination by PCR Method

PCR Conditions primers 18srDT and ZEOR 0.5 µM each genomic DNA 500 ng

10×La PCR buffer 5 µl dNTP 0.4 mM $MgCl_2$ 2.5 mM

La taq (5 units/µl) 0.5 µl sterile water q.s.

Total 50.0 µl

Thermal Cycler

94° C. for 2 minutes, followed by 30 cycles (94° C. for 20 seconds, 64° C. for 5 minutes, and 72° C. for 10 minutes)

Oligonucleotide Primers Used in Amplification

Primer Sequence (5'-3')

```
18srDT   CGCAGGTTCACCTACGGAAA    (SEQ ID NO: 100)
ZEOR     TCAGTCCTGCTCCTCTTCCA    (SEQ ID NO: 101)
```

(25) Preparation of Expression Plasmid (i) Preparation of Insert

Each fragment was amplified by PCR, then gel-extracted, and its concentration was measured.

PCR Conditions for Rat Elongase 2 Gene primers epELOF and etELOR 50 pmol each pYES2 20 ng buffer#1 5 µl dNTP 0.2 mM $MgCl_2$ 1 mM KOD DNA polymerase 2.5 U sterile water q.s.

Total 50.0 µl

Thermal Cycler for Rat Elongase 2 Gene 25 cycles (98° C. for 15 seconds and 68° C. for 30 seconds)

PCR Conditions for Promoter and Terminator primers ef1α promoter <elongase> (psac I EPF and eloEPR)

ef1α promoter <no elongase> (psac I EPF and etEPR)

ef1α terminator <elongase> (eloETF and psac I ETR), and ef1α terminator <no elongase> (epETF and psac I ETR) 0.5 µM each genomic DNA 500 ng 10×La PCR buffer 5 µl dNTP 0.4 mM $MgCl_2$ 2.5 mM La taq (5 units/µl) 0.5 µl sterile water q.s.

Total 50.0 µl

Thermal Cycler for Promoter and Terminator

94° C. for 2 minutes, followed by 25 cycles (94° C. for 30 seconds, 60° C. for 30 seconds, and 72° C. for 30 seconds)

Oligonucleotide Primers Used in Amplification and Sequencing

Primer Sequence (5'-3')

| psac I EPF | ATGATTACGAATTCGAATGACT GGCTTCAAGTTTG | (SEQ ID NO: 102) |
| --- | --- | --- |
| eloEPR | GACATGTTCATTTTGTTTGGTG CTAGTAGCTT | (SEQ ID NO: 103) |
| epELOF | CAAACAAAATGAACATGTCAGT GTTGACTTTA | (SEQ ID NO: 104) |
| etELOR | CAAACCACCTACTCGGCCTTCG TCGCTTTCTT | (SEQ ID NO: 105) |
| eloETF | CCGAGTAGGTGGTTTGACCTCT TATACTTGATCGA | (SEQ ID NO: 106) |
| psac I ETR | GATTGACAGATTGAGCTCTCAA ACATACAAAAGAATT | (SEQ ID NO: 107) |
| etEPR | ACCACTTACATTTTGTTTGGTG CTAGTAGCTT | (SEQ ID NO: 108) |
| epETF | ACAAAATGTAAGTGGTTTGACC TCTTATACTTGAT | (SEQ ID NO: 109) |

(ii) Workflow

The prGPZT (5396 bp) comprising the gapdh promoter, bleomycin resistance protein gene, terminator, 18S rRNA gene introduced therein was digested with SacI, then gel-extracted, and its concentration was measured. The ef1 promoter <elongase>, the rat elongase 2 gene, the ef1 terminator <elongase> were introduced into the SacI site of the prGPZT using Fusion Enzyme according to the protocol of "BD In-Fusion™ Dry-Down PCR Cloning Kit (BD Biosciences)," and the resulting plasmid was designated as prGPZT-EPELOT (7999 bp). The absence of mutation in the rat elongase 2 gene was confirmed by sequencing. As a negative control, the ef1 promoter <no elongase> and the ef1 terminator <no elongase> were introduced into the SacI site of the prGPZT in the same way, and the resulting plasmid was designated as prGPZT-EPT (7210 bp) (FIG. 20).

(B) Results (1) Test for Drug Sensitivity of CB 15-5 Strain

Figure 2:
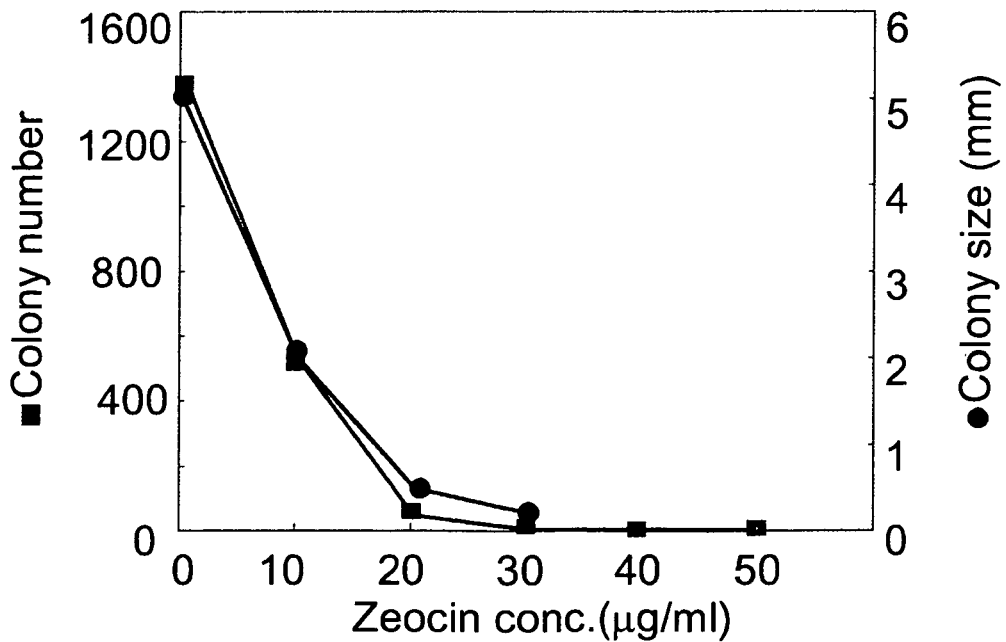
FIG. 2 shows the Zeocin sensitivity of *Schizochytrium* sp. CB15-5.

For determining a selection marker, drug sensitivity to Zeocin, a substance breaking DNA structure, was examined. As a result, a tendency of concentration-dependent decrease in the number and size of the colonies was observed in the medium containing 10 to 30 µg/ml Zeocin (FIG. 2). Therefore, a gene imparting resistance to bleomycin, a Zeocin analog, was used as a selection marker.

(2) Isolation of 18S rRNA Gene by PCR Method

The 18S rRNA gene considered to exist in many copies on the chromosome was used as a homologous recombination gene. The 18S rRNA gene was isolated by PCR on the basis of homology to microorganisms belonging to the same category, and the upstream and downstream regions thereof were further isolated by inverse PCR (SEQ ID NO: 1). For comparing it with 18S rRNA genes of other microorganisms of Labyrinthulomycota, a molecular phylogenetic tree was prepared. As a result, it was found that the 18S rRNA gene has high homology to those of *Schizochytrium limacinum* that is a high docosahexaenoic acid-producing microorganism and a KH105 strain of the genus *Schizochytrium* that is a carotenoid-producing microorganism (FIG. 3).

(3) Isolation of Each Gene of Actin, Elongation Factor 1α (ef1α), and Glyceraldehyde-3-Phosphate Dehydrogenase (gapdh) by PCR Method Those from each gene of actin, ef1α, and gapdh expected to provide constitutive expression were used as promoter and terminator genes controlling the expression of the bleomycin resistance gene. Therefore, a partial fragment of each gene of actin, ef1α, and gapdh lacking sequence information in Labyrinthulomycota was obtained from cDNA of the CB 15-5 strain by a PCR method on the basis of homology to organisms of other species, and the full length thereof was obtained by 5' RACE and 3' RACE methods. The nucleotide sequence of the actin gene is shown in SEQ ID NO: 8 (coding region: nucleotide Nos. 1504 to 2634); the nucleotide sequence of the ef1α gene is shown in SEQ ID NO: 9 (coding region: nucleotide Nos. 1487 to 2791); and the nucleotide sequence of the gapdh gene is shown in SEQ ID NO: 10 (coding region: nucleotide Nos. 1358 to 2377). Amino acid sequences encoded by these nucleotide sequences were examined for their homology to those of related microorganisms. As a result, high homology was obtained, and the gene of interest was judged to be obtained because a region conserved in each of the proteins existed in the sequence of the CB15-5 (FIGS. 4 to 6).

(4) Confirmation of Expression of Each Gene of Actin, ef1α, and gapdh by Real Time PCR Method Primers specific to each gene and cDNA of the CB15-5 strain were used to perform real time PCR using SYBR Green. Fluorescence value data of each gene obtained was analyzed by Fit Point Method of "Light-Cycler Software Ver. 3.5 (Roche)," and a standard curve was prepared with the standard to calculate a sample concentration (FIGS. 7 to 9). The sample concentration 10×(C0—CX) obtained therefrom was calculated in molarity using a molecular weight of each PCR product. As a result, an expression level was shown to be highest in actin, followed by ef1α, and gapdh (FIG. 10). The expression levels of actin and ef1α were shown to be larger than at least that of gapdh, suggesting that the actin and ef1α genes can be used as promoters. Because the expression of gapdh, though its absolute level was unknown, was confirmed, a promoter was also obtained therefrom.

(5) Acquisition of Promoter and Terminator of Each Gene of Actin, ef1α, and gapdh by Inverse PCR Method In a method for the acquisition, the genomic DNA which was completely digested with a restriction enzyme with no recognition sequence on each gene sequence and then self-ligated was used as a template to perform inverse PCR using primers corresponding to each gene sequence, and the obtained fragments were sequenced (FIG. 11). Three restriction enzymes absent in each gene were selected for each of the genes (KpnI, NheI, and EcoRI for actin, HindIII, NheI, and EcoRI for ef1α, KpnI, HindIII, and NheI for gapdh). The genomic DNA which was completely digested with each of the restriction enzymes and then self-ligated was used as a template to perform inverse PCR using primers corresponding to the gene sequence. As a result, bands of 2 to 9 Kb were obtained (FIG. 12).

The bands (KpnI <actin> 4 Kb, EcoRI <actin> 2 Kb, HindIII <ef1α> 5 Kb, NheI <ef1α> 5 Kb, HindIII <gapdh> 6 Kb, NheI <gapdh> 3 Kb) of samples of each gene digested with two different enzymes, were excised and inserted into T-vectors. For determining the lengths of the obtained promoters and terminators, the respective restriction maps of the samples were prepared (FIG. 13). Then, sequence information of the respective promoter and terminator regions of 0.5 to 1.5 Kb was obtained by sequence analysis. The promoter sequences of the actin, ef1α, and gapdh genes are shown in SEQ ID NOs: 2 to 4, while the terminator sequences of the actin, ef1α, and gapdh genes are shown in SEQ ID NOs: 5 to 7.

As a result of comparison of the sequences of the samples of each gene, the promoter and terminator regions were homologous in all of the ef1α and gapdh samples. In the actin samples, only the promoter regions of approximately 120 bp from the initiation codon were homologous (FIG. 14), and the promoters subsequent after 120 bp and the terminators were nonhomologous. Therefore, the sequence of the KpnI <actin> 4 Kb sample from which the 1.5-Kb promoter and the 1-Kb terminator could be obtained was used for actin.

(6) Introduction of Plasmid by Electroporation

The transfer plasmid having the ef1α promoter (FIG. 15) was converted to a linear plasmid with sacII, and a main culture medium (3 days) of the strain was prepared. The linear plasmid was introduced into the cells of Labyrinthulomycota (50 mM sucrose suspension ($3 \times 10^7$ cells/80 µl)) with a size of 5 µm or less by electroporation under each condition of 200 V, 500 V, 1500 V, and 2500 V (50 µF, 13Ω). The cells were seeded onto a medium containing 100 µg/ml Zeocin. As a result, colonies exhibiting Zeocin resistance were obtained from the electroporation at 200 V and 500 V. Moreover, the largest number of colonies was obtained from the electroporation at 500 V, whereas no colony was obtained from the electroporation at 1500 V and 2500 V (Table 1). Therefore, electroporation was performed at 500 V in subsequent experiments.

TABLE 1

| Voltage | Number of transformant Transformant/µgDNA(plasmid) |
|---|---|
| 200 V | 1.0 |
| 500 V | 2.0 |
| 1500 V | — |
| 2500 V | — |

Next, a main culture medium (3 days) of the strain was prepared, and the linearized transfer plasmid having the ef1α promoter was introduced into the cells of Labyrinthulomycota (50 mM sucrose suspension) with a size of 5 µm or less and a normal size by electroporation under the condition of 500 V, 50 µF, 13Ω. The cells were seeded onto a medium containing 100 µg/ml Zeocin. As a result of the introduction using the cell having the unfixed size, colonies exhibiting Zeocin resistance were also obtained, and therefore, subsequent experiments were performed with the size unfixed (Table 2).

TABLE 2

| Cell size | Number of transformant Transformant/µgDNA(plasmid) |
|---|---|
| <5 µm cell | 1.2 |
| Normal cell | 2.5 |

Next, a main culture medium (4 days) of the strain was prepared, and the linearized transfer plasmid having each gene promoter was introduced into the cells of Labyrinthulomycota (50 mM sucrose suspension) with a normal size by electroporation under the condition of 500 V, 50 µF, 13Ω. The cells were seeded onto a medium containing 100 µg/ml Zeocin. As a result of the introduction of all of three plasmids under the determined condition, Zeocin resistance strains were obtained for all of the samples comprising the plasmid introduced (Table 3).

TABLE 3

| Plasmid | Number of transformant Transformant/µgDNA(plasmid) |
|---|---|
| Control | — |
| actin promoter | 0.5-7 |
| ef1α promoter | 1.2-50 |
| gapdh promoter | 0.5-3 |

Next, transformation efficiency depending on the number of culture days of the cells to be transformed was compared. As a result, the cells on the 3 to 4 days were shown to be suitable for transformation (FIG. 16).

Next, a main culture medium (3 days) of the strain was prepared, the linearized and circular transfer plasmids having each gene promoter were introduced into the cells of Labyrinthulomycota (50 mM sucrose suspension) with a normal size by electroporation under the condition of 500 V, 50° F., 13Ω. The cells were seeded onto a medium containing 100 µg/ml Zeocin. As a result of the introduction of the circular plasmid, colonies exhibiting Zeocin resistance were obtained as in the linear plasmid (Table 4).

TABLE 4

| Plasmid | Number of transformant Transformant/µgDNA(plasmid) |
|---|---|
| Linear | 0.3-50 |
| Circular | 0.5-50 |

Next, culture media (1 day to 4 days) of a KH105 strain were used to introduce the plasmids in the same way as in the CB15-5 strain. However, resistance strains were not obtained.

(7) Test for Zeocin Sensitivity of Transformant

The obtained transformants were examined for their sensitivity to Zeocin. As a result, the wild type completely became nonviable in 20 µg/ml Zeocin, whereas the transformants having each gene promoter were viable in up to 4000 µg/ml (actin), 6000 µg/ml (ef1α), and 2000 µg/ml (gapdh) Zeocin (FIG. 17).

(8) Confirmation of Transgene by PCR Method

For confirming the introduction of the bleomycin resistance gene, the genomic DNA of the obtained transformant was used as a template to perform PCR using bleomycin resistance gene-specific primers. As a result, the gene transfer was shown to be successful because bands with the same size as that obtained in the control plasmid were obtained (FIG. 18).

(9) Confirmation of Homologous Recombination by PCR Method

For confirming that homologous recombination occurred at the 18S rRNA gene locus, primers corresponding to the downstream region of the 18S rRNA gene existing in only the genomic DNA and primers specific to the bleomycin resistance gene were used to perform PCR. As a result, the gene transfer to the chromosomal DNA by homologous recombination was shown to occur because an expected 3600-bp band was obtained in the transformant (FIG. 19).

INDUSTRIAL APPLICABILITY

The transformation of Labyrinthulomycota with an introduced foreign gene was achieved for the first time by using the method for introducing a gene into labyrinthulomycota according to the present invention. The use of the method for introducing a gene into labyrinthulomycota according to the present invention allows the improvement of production efficiency of lipid or carotenoid in Labyrinthulomycota.

The invention claimed is:

1. A method for introducing a transgene into chromosomal DNA of a cell of Labyrinthulomycota by homologous recombination comprising,
   (a) introducing into a cell of Labyrinthulomycota a recombinant vector comprising at least:
      (1) a polynucleotide, wherein the polynucleotide has the polynucleotide sequence set forth as SEQ ID NO: 1, the polynucleotide is homologous to a part of chromosomal DNA in the cell of Labyrinthulomycota, and the polynucleotide undergoes homologous recombination with the part of the chromosomal DNA,
      (2) a selection marker gene having a promoter sequence located upstream and a terminator sequence located downstream of the selection marker gene, and
      (3) a transgene having a promoter sequence located upstream and a terminator sequence located downstream of the transgene,
   (b) selecting a cell of Labyrinthulomycota expressing the selection marker gene.

2. The method according to claim 1, wherein the recombinant vector is a linearized plasmid.

3. The method according to claim 1, wherein the recombinant vector is introduced into the cell of Labyrinthulomycota by using electroporation, a gene gun, or a drug treatment of the cell membrane.

4. The method according to claim 1, wherein the recombinant vector comprising the transgene is introduced into the cell of Labyrinthulomycota collected from a culture medium that has reached stationary phase.

5. The method according to claim 1, wherein the cell of Labyrinthulomycota is a cell of *Schizochytrium* sp.

* * * * *

SEQUENCE LISTING

<160> NUMBER OF SEQ ID NOS: 127

<210> SEQ ID NO 1
<211> LENGTH: 1787
<212> TYPE: DNA
<213> ORGANISM: Schizochytrium

<400> SEQUENCE: 1

```
aaacatagca attctggttg atcctgccag tagtcatatg ctcgtctcaa agattaagcc      60
atgcatgtgt aagtataagc gattgtactg tgagactgcg aacggctcat tatatcagta     120
ataatttctt cggtagtttc ttttatatgg atacctgcag taattctgga ataatacat     180 gctgtaagag ccctgtctgg ggctgcactt attagattga agccgatttt attggtgaat     240
catgataatt gagcagattg acttttttag tcgatgaatc gtttgagttt ctgccccatc     300
agttgtcgac ggtagtgtat tggactacgg tgactataac gggtgacgga gagttagggc     360
tcgactccgg agagggagcc tgagagacgg ctaccatatc caaggatagc agcaggcgcg     420
taaattaccc actgtggact ccacgaggta gtgacgagaa atatcgatgc gaagcgtgta     480
tgcgctttgc tatcggaatg agagcaatgt aaaaccctca tcgaggatca actggagggc     540
aagtctggtg ccagcagccg cggtaattcc agctccagaa gcatatgcta aagttgttgc     600
agttaaaaag ctcgtagttg aatttctggc atgggcgacc ggtgctttcc ctgaatgggg     660
attgattgtc tgtgttgcct tggccatctt tctcatgcta ttttggtatg agatctttca     720
ctgtaatcaa agcagagtgt tccaagcagg tcgtatgacc ggtatgttta ttatgggatg     780
ataagatagg acttgggtgc tattttgttg gtttgcacgc ctgagtaatg gttaatagga     840
acagttgggg gtattcgtat ttaggagcta gaggtgaaat tcttggattt ccgaaagacg     900
aactagagcg aaggcattta ccaagcatgt tttcattaat caagaacgaa agtctgggga     960
tcgaagatga ttagatacca tcgtagtcta gaccgtaaac gatgccgact tgcgattgtt    1020
gggtgcttta tacatgggcc tcagcagcag cacatgagaa atcaaagtct ttgggttccg    1080
gggggagtat ggtcgcaagg ctgaaactta aaggaattga cggaagggca ccaccaggag    1140
tggagcctgc ggcttaattt gactcaacac gggaaaactt accaggtcca gacataggta    1200
ggattgacag attgagagct ctttcatgat tctatgggtg gtggtgcatg gccgttctta    1260
gttggtggag tgatttgtct ggttaattcc gttaacgaac gagacctcgg cctactaaat    1320
agtgcgtggt atggcaacat agtgcgtttt tacttcttag agggacatgt ccggtttacg    1380
ggcaggaagt tcgaggcaat aacaggtctg tgatgccctt agatgttctg ggccgcacgc    1440
gcgctacact gatgggttca tcgggtttta attctgtttt tatggaattg agtgcttggt    1500
cggaaggcct ggctaatcct tggaacgctc atcgtgctgg ggctagattt ttgcaattat    1560
taatctccaa cgaggaattc ctagtaaacg caagtcatca gcttgcattg aatacgtccc    1620
```

```
tgcccttgt acacaccgcc cgtcgcacct accgattgaa cggtccgatg aaaccatggg    1680
atgtttctgt ttggattcat ttttggacag aggcagaact cgggtgaatc ttattgttta    1740
gaggaaggtg aagtcgtaac aaggtttccg taggtgaacc tgcggaa                   1787

<210> SEQ ID NO 2
<211> LENGTH: 1503
<212> TYPE: DNA
<213> ORGANISM: Schizochytrium

<400> SEQUENCE: 2
cttcatactc tcgcatttcc taatttattt gagcacgagc caacacaagc tccctcgtaa      60
gagaaggtag taggtacttt agcagtgagc atctgggtag aggtatctgc cttctaatat     120
cacctacctc aaggtccgtg ccacgcgcga gggaactctg aagaagacta gaagtgcact     180
actactccac gagggaatcc cgctttcacg agatactcaa cttggactat caacgacata     240
cattctcagc cagtaggcac ccagcactct gtagtagctg tacctaatgg aagactagat     300
gctctgacac tcaacttacc tacttctgtt tctgcggtgt ggaatatcgc agttattaac     360
taaaaacagg ataaaaatga gaatactatg taagtttaat ttattattag tagcaatcat     420
atctcatata tggaatcttt ttctaaagat aaagcaaaaa caaacattat tttggaaata     480
aaaagagttg ttaatcaaag cgtaagacgt cctatacagc tgcctgtatg atgggacatt     540
aggtataaat tggtcctaag aaggttcacc caagtcattg gccattcaag ttgagtaaag     600
ctaagtgatt caagttgttt tgaccttgag ttttttaccg caagttaaaa gatctcaact     660
cagtacctct gactacctcg tgagagtggc cattggcttt tgatatttac ttgtgtaaga     720
agagttcctc ccgacggcag gtgggcagta gtacctacca ataggagaag cgctgcgtgc     780
tattcctgaa gtacacacca cgtaggtgag tgagttttat tattcttttt attttaaaca     840
tagtgtgtat gaagcttact atagttagtt aattttagaa ataccatacc ataatatatc     900
atctttatat agtcgggata caacagaaaa gggcaatgaa atcgactttt gggcgggcga     960
gtgaaggcga gagtccgcag ctgctctggc cttcgggtcg tgtccgcact cacattggta    1020
gtctgtagac atgatttgga ccttctgtag gcagagagta cctactagga gcgtcttcca    1080
ataatcgcct cgatttcccc aacctggatg atgctggtgg ctcaacttga actaaaacct    1140
gaggatgaag gagccactcg attccacgca cacccttcag gtggtcattt gcaggttagc    1200
gatagaggta tctctcacaa acactgtaaa tagttttgtg agtaaataca cacacgagca    1260
ctcctataaa gggtgtgtaa gctaaggaaa atcccctcgc aacacactga gtatcaaaag    1320
aggaacctac gactaagaag gttatcataa atggatgtaa tcagaggagg taacactgta    1380
aatttatgga gacagtggag ggtctttggg cacgaagatc tgcaagcgcg ccatcagcag    1440
atccgcaacc ttcgagctca agaagcaact caacagtaga agaacaagca cccaactagc    1500
aaa                                                                  1503

<210> SEQ ID NO 3
<211> LENGTH: 1486
<212> TYPE: DNA
<213> ORGANISM: Schizochytrium

<400> SEQUENCE: 3
tcatgctcct ttcccgccaa aaagaaagaa gaggaaagca ccccgaagaa aagaaagaaa      60
tcacccaaac accctcctcc ttcctcgtcc acagacagct cagaataatg aaagctatct     120
```

-continued

| | |
|---|---:|
| ttccatcgct cttgacctaa ctctctttct gctcctgtaa attcatccaa caaatgttta | 180 |
| gtctcagaaa cccttctgcc tcatactact acttactacc ttccttactt gaaagcaggc | 240 |
| aggctcacgg ccagcttggc agataggata gttctcatat ctattgctga tcgttcccgt | 300 |
| ttctttctca aagcaaagtc ttttctcttc aattcctttt ctttttcttt tcttttcagg | 360 |
| ctctccaacg ttttcaggag tagtacattt tctacttagt aattagaaag cttagtactt | 420 |
| tttgcttttc tggattctga agacttggaa atagaaagaa attaaaaatc ttttttcttct | 480 |
| ttctttcagc ctttgctgga ctccctcgca cgcctccttc ttcccagcc atccatcagc | 540 |
| ggcactccac ccgcgcttca acgctcgctc gagtgcgtgc ttatttgcct tcaacgcggc | 600 |
| gcggcggtta atatagtccc agcactcctt aaggggggca tcgcagggat tacctttta | 660 |
| aaacctgtca cagaattaca tcttccctcg catcaaagtg ttcccggccg cgtctcacat | 720 |
| ctaagttta taacctacac cccttgtggg gtaggggcga attctatgta cacagcacct | 780 |
| cagaacttgc gcgcgttccg tgacaaatga ggggtgtggc ggcgcattcg ccgcatcgc | 840 |
| cacattcaga tatctaacat acccccctt cgcgatgagt ggcaggcgag gcgattcggc | 900 |
| tcgcgagagg cgaggtgccc acagcagacc agtaacgagg agccaaggta ggtgaccacc | 960 |
| gacgactacg accacgacca cgaccacagc cacggcggct gcagccacgg gacgcctcgc | 1020 |
| atggcagcgc atcagcacca gcaacgacag ctgcgaggag cgcagggccg atctggacgc | 1080 |
| gccggagccg cacgaccaat gccgacgcaa cgctgattct tctggattcc ctctttacat | 1140 |
| gcatatatgt gtagaggtgc ggatgaaatg ccctgcgaat aaatgactgg cttcaagttt | 1200 |
| gcctgccgta tgctcgaaag tgcgtgtgca gacacaggca cgaccgagag gacaacagtc | 1260 |
| tgtgcttacc tcaccagcac attcttgcaa cgccatacga agcacgcgaa atcttgtggc | 1320 |
| tcagagagga aggcattcgt ggtacgggaa cgtggggaac gctatcaatt tagaattgaa | 1380 |
| aatgagtgaa ccagacaact aactgtgact tgaactgttg ctccacgcat caaaaccaaa | 1440 |
| cctttaacag aagtagacca gttcgaagct actagcacca aacaaa | 1486 |

<210> SEQ ID NO 4
<211> LENGTH: 1357
<212> TYPE: DNA
<213> ORGANISM: Schizochytrium

<400> SEQUENCE: 4

| | |
|---|---:|
| ttgatcttgt gagggctcca ctggaatttt ccgacacaag aaagtgccag tggacaaagg | 60 |
| gggaagtggg cctcgaaata gcggtatggt tatgtgaggg atacggggcg gagttccggc | 120 |
| gttccctcag gccttcctct ctgcgcctca ggcaagtttc taagaaaagt gcttttggat | 180 |
| aataatcttg tatggaaatg tgaagcgcaa gtgcgcagaa cctagaaaat ctaaaacaaa | 240 |
| agaaaaaaga gatcgtcacc cgagcagcag aatcaattca ctccaaggta agtaaggcgt | 300 |
| gctgtgcggg agcgccccg gccagtcagt gttggagctt gggatgagtt gcatctgcgc | 360 |
| gaagggttgg cccatccatc tcaagtcctt tcctggcggt ttcgcccgcg tcaccagccg | 420 |
| cctggtgctc ctgatggatg gggactctgg atggtcgaaa gaggatgtgt tgtatctatc | 480 |
| tgtctgataa ggtaaaaggg gacggcttct gtactttcct tcttcgctcg ctcccgatcg | 540 |
| tgtcttctag gatgcgcgct tttgatgtgc tgaagattcc gagcaccgtg tgctatgccg | 600 |
| tctccgtctt gcctgtgttg gcggctagct agcgctgagg gttgtggacg gccttgggaa | 660 |
| ttaggaaaag aaagatactc gtgacgttga aacgtcctgt tcttttttctt ttctaagtat | 720 |
| tttctattcc aagtctttac tttctgttcc tttcatttca cttcaagtac atcgtcacct | 780 |

-continued

```
ctatcgatct agtgtgagcc gaattgagcc tcctgtcaat gtagcaggag gaactacaga      840
ggttccgact ggtacggaac aaacgaatcg gcgaaacgga gagtaggcat gaagttgttg      900
ttgtccaaga tcaaaaagat agaaacgaat atctttcttg ttctgctacc tacattgaaa      960
cggacatgaa aggcgacaat tctagatgaa gacactgcca aaagggaaga agcgctcggc     1020
caccgcagca agaaaggcaa gagagagaag ataaagtaaa ttttcgagag aacaaaagaa     1080
atgaatgcag gaaggaagga aggaaggagg ggaggtagtg aaagaacgcg tgacaagatt     1140
tgtaatgaag aacatggcat gaaagaacga acagggggga ctgacgattt gagggactga     1200
tgtgcgcaat tgaatctttt tcatttgcat tgcggctgcg gcgcaaacg aaacaaaaat      1260 aattattcgg cattcacttt gcttgcgttg ttggacaaca taaccataac agaaacaaaa     1320
gcaaggaaac ctagcgcaca cataaacacc aagcaaa                              1357
```

<210> SEQ ID NO 5
<211> LENGTH: 994
<212> TYPE: DNA
<213> ORGANISM: Schizochytrium

<400> SEQUENCE: 5

```
attggagtga tggaatgccc tctccgtgtg gtgtatccga ttgacaaatc ttaaactcct       60
ccaagtagta ggcttcagtg cttccttgga attgagacat gaaatcatgc aacatcccac      120
cgacaggatt tatgtagtat cgcatcctct cttgttttac actctttgcc cataaattca      180
tgaacacttt cttctctttt ctctcaaaaa actagcttaa tttcatttaa gtcatgaaga      240
ctaccaatga caatcttgtc aacaaccaaa caacagctta gtttcatct aacttaagag       300 actaccatga caatctttc acttagacaa acattatagt gaatgcattg catcataata      360
tatttattag gctttgactt caactatgtc caggcttttg ggcaccaagg accacagtta      420
caaaagcaga agatagttat gttgctatga atcaaatgaa aatgaacaaa aaagatttca      480
ggctgatatg tttcgatttg attttttgct caaatgcaat taaaagaaga cagacctcaa      540
ggtcaaatgt gattattaga atcttggaac gaatccgcac atatccagtt accaaattgt      600
tctcgcgcca ttgtgtaaat tcgctttatg atgtagcaat cacgtcccaa cccctaatct      660
tgtaaagaga agcagctata gctcagtggc agagcgtccg cctgacacgc ggaaggtcac      720
gagttcgatc ctcgttagct gtataattgt attttttgcct ctattttga tcaataatct      780 atggtggaca tgtggttatg tagaacggca gccgtgatcc tttcaacaaa atgtgccagc      840
agctatagct cagtggcaga gcgtccgcct gacatgcgga aggtcacgag ttcgatcctc      900
gttagctgta aattactttt ttggtttaat tttgaccaac gttagttcgt ttgttttttgc      960 tgttgtaggg cagttggcct cagctctttc aaca                                  994
```

<210> SEQ ID NO 6
<211> LENGTH: 995
<212> TYPE: DNA
<213> ORGANISM: Schizochytrium

<400> SEQUENCE: 6

```
gtggtttgac ctcttatact tgatcgaaat actacctaca cttaaccttt tttgcgattt       60
tatcgtgatt actttgcttt tttcttgctt ttgttttccat tcttcctaag ttgcgtggcc      120
tcattgtatt gaatacccgc aggctggtgt tatcttgctt atcatatttt tacttgaatg      180
ttcgtgggtt ctgccatatt ctctggaggt ttttttgttat gaagctagga tgtgcgtttc      240
```

```
ttgtcttgat agtgttgtct tgaaatagtt aatcttttaa ttcttttgta tgtttgagag   300
attgattcag catgggtatt caggatagtg tacttgatgg tacaatcgtt gttaatggtt   360
cgtcgtctgt tttttttaatc taaagatttg acatgtcgga aaaggtcaca acagatggag   420
```
```
tccccccgatt ttgtagtggt tgttggagat tttggcattt ttagatgatt cttttctgt   480 gttctgctgc gctgttgcat atacttgctt atgtccaaga ttggtgcttg taagataccc   540
gggttgattg agataggcct agatgtttat ttatggtatt gggtattggg tattgtgaac   600
tacgaaatca ttgatgtttg agactttaaa aatatactaa cgtttctact gtaaaacatg   660
atggttatag gtgtttaaga aaataggttt attggatgct aagctatgga taaaagttgt   720
ttaagaggaa agtattcgat atcgcaactg tgtcgatcaa cgatgggcaa agaatctatt   780
cgctaaatca aaaacctatc ctgtctgtcg ttggcgtgcg accaagaagc acgggttcgg   840
cagcaggcac tgtttggagc tcgagaagag ctttgtaaac gctgaggtgc ctcccatcgt   900
gggagccgtc agagagattt ctgctgcttc actttcgttg aaaagtggag tgaaccatct   960
gttcgacgcc cggaccacaa cgtgagttgg gaaac                               995

<210> SEQ ID NO 7
<211> LENGTH: 978
<212> TYPE: DNA
<213> ORGANISM: Schizochytrium

<400> SEQUENCE: 7
atgtacccaa taccacaccg gtagcttctc gcggcggctg acaagaaaga ttgttttttac    60 acatttcgag gcattgatga cccttatcga cctatcgtct cagatcataa aatgcacgag   120
catgaagtac gcgtgttgtg acttgcttgc gtcccacctt ctagatggct tcttctcttt   180
caagtgatta aaacaccaca gtagatgagg actcttagta agcactgaag aagcgagtaa   240
atagccctca tcccgtttcc ctcttttcta acacactttg tttggaattc taaaatatct   300
tttatcatct ctttttcattc acaaaactag tatttctgca ttagaaatca ttatcctatc   360
tggcactttc actctgacaa gaacttgccg tacatggcgg atcctggcaa tcattttact   420
tgtacagacc caagactttg tgagtcagta aatagtaaag aaatgcagaa taatcattag   480
ataattgcaa aaccctgatc ttcaaaatgt tatatcacaa gtacctacca agacatttgt   540
atcttctttt tgtcttatgc attttattt cccttagcgc aattaaaaat attaaataac   600
tgacgactct tttcttaagg attcgcggtt tgctagttgc actattgaaa agagcacggt   660
attaatttca tagttttact ttgttggcaa tctcagcaaa catgggtttt aattttaaaa   720
ttaaataata cttgtgttag actcaaaaga tacctataca acccttaggg ctcatcgtca   780
acatttgcaa attaaaacga ttcagctcct ttggtacggt catgtctgtt tctgatgcac   840
tgaaaaacct tggacgaacg acacatctta ttttcattag gacatctaaa aaacgttgta   900
aagagtatac aataagcata aaaaggaga agagaaaaaa gaaagacata catggttctg   960
ctcttctagt gcttcaag                                                 978

<210> SEQ ID NO 8
<211> LENGTH: 3628
<212> TYPE: DNA
<213> ORGANISM: Schizochytrium

<400> SEQUENCE: 8
cttcatactc tcgcatttcc taatttattt gagcacgagc caacacaagc tccctcgtaa    60
gagaaggtag taggtacttt agcagtgagc atctgggtag aggtatctgc cttctaatat   120
```

-continued

```
cacctacctc aaggtccgtg ccacgcgcga gggaactctg aagaagacta gaagtgcact    180
actactccac gagggaatcc cgctttcacg agatactcaa cttggactat caacgacata    240
cattctcagc cagtaggcac ccagcactct gtagtagctg tacctaatgg aagactagat    300
gctctgacac tcaacttacc tacttctgtt tctgcggtgt ggaatatcgc agttattaac    360
taaaaacagg ataaaaatga gaatactatg taagtttaat ttattattag tagcaatcat    420
atctcatata tggaatcttt tctaaagat aaagcaaaaa caaacattat tttggaaata     480
aaagagttg ttaatcaaag cgtaagacgt cctatacagc tgcctgtatg atgggacatt     540
aggtataaat tggtcctaag aaggttcacc caagtcattg gccattcaag ttgagtaaag    600
ctaagtgatt caagttgttt tgaccttgag ttttttaccg caagttaaaa gatctcaact    660
cagtacctct gactacctcg tgagagtggc cattggcttt tgatatttac ttgtgtaaga    720
agagttcctc ccgacggcag gtgggcagta gtacctacca ataggagaag cgctgcgtgc    780
tattcctgaa gtacacacca cgtaggtgag tgagttttat tattcttttt attttaaaca    840
tagtgtgtat gaagcttact atagttagtt aattttagaa ataccatacc ataatatatc    900
atctttatat agtcgggata caacagaaaa gggcaatgaa aatcgacttt gggcgggcga    960
gtgaaggcga gagtccgcag ctgctctggc cttcgggtcg tgtccgcact cacattggta   1020
gtctgtagac atgatttgga ccttctgtag gcagagagta cctactagga gcgtcttcca   1080
ataatcgcct cgatttcccc aacctggatg atgctggtgg ctcaacttga actaaaacct   1140
gaggatgaag gagccactcg attccacgca caccccttcag gtggtcattt gcaggttagc   1200
gatagaggta tctctcacaa acactgtaaa tagttttgtg agtaaataca cacgagca    1260
ctcctataaa gggtgtgtaa gctaaggaaa atccctcgc aacacactga gtatcaaaag    1320
aggaacctac gactaagaag gttatcataa atggatgtaa tcagaggagg taacactgta   1380
aatttatgga gacagtggag ggtctttggg cacgaagatc tgcaagcgcg ccatcagcag   1440
atccgcaacc ttcgagctca agaagcaact caacagtaga agaacaagca cccaactagc   1500
aaaatggctg acgacgaagt tcaagccctt gtcattgaca acggctccgg tatgtgcaag   1560
gccggtttcg ccggtgacga tgcaccccgc gccgtcttcc cctccattgt cggccgcccc   1620
aagcaccccg gtatcatggt cggcatggac cagaaggacg cctatgtcgg tgatgaggcc   1680
cagtccaagc gtggtgtcct caccctcaag tacccattg agcacggtat cgtgaccaac    1740
tgggacgaca tggagaagat ctggcaccac accttctaca cgagctccg cgttgccccc    1800
gaggagcacc ccgttctcct caccgaggcc cccctcaacc ccaaggccaa ccgtgagcgc   1860
atgacccaga tcatgttcga gaccttcaac gtgcccgcca tgtacgtcaa catccaggcc   1920
gttctctccc tctacgcctc tggtcgtacc accggtgccg tcctcgactc tggtgatggt   1980
gtcacccaca ccgtccccat ctacgagggt tacgctctcc cgcacgccgt tctccgtatc   2040
gatcttgccg ccgtgacct cactgactac atgatgaaga tcctcaccga gcgtggctac   2100
tccttcacca ccaccgccga gcgcgagatt gtccgtgaca tcaaggagaa gcttgcctac   2160
gtcgcccagg acttcgacga ggagatgcgc ctcgctgccg agtcctccgc cctcgagaag   2220
tcctacgagc ttccggacgg taacttcatc accatcggca acgagcgctt ccgtgccccg   2280
aggttcctct tccagccgtc cttcatcggc aaggaggccc agggtgtcca cgacaccatg   2340
ttccagacca tcatgaagtg tgacgtcgat atccgtaagg acctctacgc caacatcgtc   2400
atgtctggtg gctccaccat gtacgagggt ctcgccgctc gtctcgagaa ggagatgatc   2460
```

-continued

```
gcccttgccc cctccaccat gaagatcaag gtcgtcgccc ccctgagcg caagtactcc      2520 gtgtggatcg gtggctccat tcttgcctcc ctctccacct tccagcagat gtggatctcc      2580
aagcaggagt acgacgagtc tggaccctcg atcgtccacc gcaagtgctt ctaaattgga      2640
gtgatggaat gccctctccg tgtggtgtat ccgattgaca aatcttaaac tcctccaagt      2700
agtaggcttc agtgcttcct tggaattgag acatgaaatc atgcaacatc ccaccgacag      2760
gatttatgta gtatcgcatc ctctcttgtt ttacactctt tgcccataaa ttcatgaaca      2820
ctttcttctc ttttctctca aaaaactagc ttaatttcat ttaagtcatg aagactacca      2880
atgacaatct tgtcaacaac caaacaacag cttaagtttc atctaactta agagactacc      2940
atgacaatct tttcacttag acaaacatta tagtgaatgc attgcatcat aatatattta      3000
ttaggctttg acttcaacta tgtccaggct tttgggcacc aaggaccaca gttacaaaag      3060
cagaagatag ttatgttgct atgaatcaaa tgaaaatgaa caaaaaagat tcaggctga      3120 tatgtttcga tttgatttt tgctcaaatg caattaaaag aagacagacc tcaaggtcaa      3180
atgtgattat tagaatcttg gaacgaatcc gcacatatcc agttaccaaa ttgttctcgc      3240
gccattgtgt aaattcgctt tatgatgtag caatcacgtc ccaacccta atcttgtaaa      3300 gagaagcagc tatagctcag tggcagagcg tccgcctgac acgcggaagg tcacgagttc      3360
gatcctcgtt agctgtataa ttgtattttt gcctctattt ttgatcaata atctatggtg      3420
gacatgtggt tatgtagaac ggcagccgtg atccttcaa caaaatgtgc cagcagctat      3480
agctcagtgg cagagcgtcc gcctgacatg cggaaggtca cgagttcgat cctcgttagc      3540
tgtaaattac ttttttggtt taattttgac caacgttagt tcgtttgttt ttgctgttgt      3600
agggcagttg gcctcagctc tttcaaca                                        3628
```

<210> SEQ ID NO 9
<211> LENGTH: 3786
<212> TYPE: DNA
<213> ORGANISM: Schizochytrium

<400> SEQUENCE: 9

```
tcatgctcct ttcccgccaa aagaaagaa gaggaaagca cccgaagaa aagaaagaaa        60 tcacccaaac accctcctcc ttcctcgtcc acagacagct cagaataatg aaagctatct      120
ttccatcgct cttgacctaa ctctctttct gctcctgtaa attcatccaa caaatgttta      180
gtctcagaaa cccttctgcc tcatactact acttactacc ttccttactt gaaagcaggc      240
aggctcacgg ccagcttggc agataggata gttctcatat ctattgctga tcgttcccgt      300
ttctttctca aagcaaagtc ttttctcttc aattcctttt cttttttctt tcttttcagg      360
ctctccaacg ttttcaggag tagtacattt tctacttagt aattagaaag cttagtactt      420
tttgcttttc tggattctga agacttggaa atagaaagaa attaaaaatc ttttctctct      480
ttctttcagc ctttgctgga ctccctcgca cgcctcctcc ttccccagcc atccatcagc      540
ggcactccac ccgcgcttca acgctcgctc gagtgcgtgc ttatttgcct tcaacgcggc      600
gcggcggtta atatagtccc agcactcctt aagggggca tcgcagggat taccttttta      660
aaacctgtca cagaattaca tcttccctcg catcaaagtg ttcccggccg cgtctcacat      720
ctaagtttta taacctacac cccttgtggg gtaggggcga attctatgta cacagcacct      780
cagaacttgc gcgcgttccg tgacaaatga ggggtgtggc ggcgcattcg gccgcatcgc      840
cacattcaga tatctaacat acccccccctt cgcgatgagt ggcaggcgag gcgattcggc      900
tcgcgagagg cgaggtgccc acagcagacc agtaacgagg agccaaggta ggtgaccacc      960
```

-continued

```
gacgactacg accacgacca cgaccacagc cacggcggct gcagccacgg gacgcctcgc    1020
atggcagcgc atcagcacca gcaacgacag ctgcgaggag cgcagggccg atctggacgc    1080
gccggagccg cacgaccaat gccgacgcaa cgctgattct tctggattcc ctctttacat    1140
gcatatatgt gtagaggtgc ggatgaaatg ccctgcgaat aaatgactgg cttcaagttt    1200
gcctgccgta tgctcgaaag tgcgtgtgca gacacaggca cgaccgagag gacaacagtc    1260
tgtgcttacc tcaccagcac attcttgcaa cgccatacga agcacgcgaa atcttgtggc    1320
tcagagagga aggcattcgt ggtacgggaa cgtggggaac gctatcaatt tagaattgaa    1380
aatgagtgaa ccagacaact aactgtgact tgaactgttg ctccacgcat caaaaccaaa    1440
cctttaacag aagtagacca gttcgaagct actagcacca aacaaaatgg gcaagacgaa    1500
ggagcacgtc aaccttgtcg tcatcggcca cgtcgatgcc ggtaagtcca ccaccaccgg    1560
ccacttgatc tacaagtgcg gtggtatcga caagcgtacc atcgagaagt tcgagaagga    1620
ggccgccgag ctcggtaagg gttccttcaa gtacgcatgg gttcttgaca agctcaaggc    1680
cgagcgtgag cgtggtatca ccatcgatat cgctctctgg aagttcgagt cccccaagtt    1740
cgacttcacc gtcatcgatg ccccggtca ccgtgatttc atcaagaaca tgattaccgg    1800
tacctcccag gccgatgttg ccgttctcgt cattgactct tcccagggtg gtttcgaggc    1860
cggtatcgcc aaggatggcc agacccgtga gcacgctctc ctcgccttca ccctcggtat    1920
ccagcagatc atcgtcgccg tcaacaagat ggacgacaag accaccatgt actccgaggc    1980
ccgcttcaac gagatcgtca acgaggtttc cgcctacctc gccaaggtcg gcttcaagcc    2040
caagaagatc aagttcgtcc ccatctccgg ctgggctggt gacaacatga tcgagaagtc    2100
ctccaacatg ccctggtaca agggcccta ccttctcgag gccctcgaca catcaagcc    2160 ccccaagcgc cccatcgaca agcctctccg tcttcccctc caggatgtgt acaagatcgg    2220
tggtatcgga acgtccccg tcggccgtgt cgagaccggt gtcatcaagc ccggtatgac    2280
cgcctacttt gcccccaccg gtgtgcagac tgaggtcaag tccgtcgaga tgcaccacga    2340
gtccatcccc gaggccaccc ccggtgacaa cgttggcttc aacgtcaaga acgtttccgt    2400
caaggacatc aagcgcggta acgtctgtgg tgatgccaag aacgaccctc cccgtggcgc    2460
caactccttc ctcgcccagg ttatcgtcat gggccacccc ggtgagatcc gcgctggcta    2520
cgcaccagtc ctcgattgcc acaccgccca cattgcctgc aagttcgccg agatccagaa    2580
caagatggac cgtcgttccg gtaagatcct tgaggatgcc cccaagttca tcaagtccgg    2640
tgactccgcc atggtcaaga tgatccctc caagaagatg tgcgttgagt ccttcactga    2700
gtaccctccc ctcggccgct tcgccgtccg tgacatgcgt gtcaccgtcg ccgtcggtgt    2760
catcaaggag gttgagaagg gtgacaagta agtggtttga cctcttatac ttgatcgaaa    2820
tactacctac acttaacctt ttttgcgatt ttatcgtgat tactttgctt ttttcttgct    2880
tttgtttcca ttcttcctaa gttgcgtggc ctcattgtat tgaatacccg caggctggtg    2940
ttatcttgct tatcatattt ttacttgaat gttcgtgggt tctgccatat tctctggagg    3000
ttttttgtta tgaagctagg atgtgcgttt cttgtcttga tagtgttgtc ttgaaatagt    3060 taatcttta attcttttgt atgtttgaga gattgattca gcatgggtat tcaggatagt    3120
gtacttgatg gtacaatcgt tgttaatggt tcgtcgtctg ttttttttaat ctaaagattt    3180 gacatgtcgg aaaaggtcac aacagatgga gtccccgat tttgtagtgg ttgttggaga    3240
ttttggcatt tttagatgat tcttttttctg tgttctgctg cgctgttgca tatacttgct    3300
```

-continued

```
tatgtccaag attggtgctt gtaagatacc cgggttgatt gagataggcc tagatgttta      3360
tttatggtat tgggtattgg gtattgtgaa ctacgaaatc attgatgttt gagactttaa      3420
aaatatacta acgtttctac tgtaaaacat gatggttata ggtgtttaag aaaataggtt      3480
tattggatgc taagctatgg ataaaagttg tttaagagga agtattcga tatcgcaact       3540 gtgtcgatca acgatgggca agaatctat tcgctaaatc aaaaacctat cctgtctgtc       3600
gttggcgtgc gaccaagaag cacgggttcg gcagcaggca ctgtttggag ctcgagaaga      3660
gctttgtaaa cgctgaggtg cctcccatcg tgggagccgt cagagagatt tctgctgctt      3720
cactttcgtt gaaaagtgga gtgaaccatc tgttcgacgc ccggaccaca acgtgagttg      3780
ggaaac                                                                 3786
```

<210> SEQ ID NO 10
<211> LENGTH: 3355
<212> TYPE: DNA
<213> ORGANISM: Schizochytrium

<400> SEQUENCE: 10

```
ttgatcttgt gagggctcca ctggaatttt ccgacacaag aaagtgccag tggacaaagg        60
gggaagtggg cctcgaaata gcggtatggt tatgtgaggg atacggggcg gagttccggc       120
gttccctcag gccttcctct ctgcgcctca ggcaagtttc taagaaaagt gcttttggat       180
aataatcttg tatggaaatg tgaagcgcaa gtgcgcagaa cctagaaaat ctaaaacaaa       240
agaaaaaaga gatcgtcacc cgagcagcag aatcaattca ctccaaggta agtaaggcgt       300
gctgtgcggg agcgcccccg gccagtcagt gttggagctt gggatgagtt gcatctgcgc       360
gaagggttgg cccatccatc tcaagtcctt cctggcggt ttcgcccgcg tcaccagccg        420
cctggtgctc ctgatggatg gggactctgg atggtcgaaa gaggatgtgt tgtatctatc       480
tgtctgataa ggtaaaaggg gacggcttct gtactttcct tcttcgctcg ctcccgatcg       540
tgtcttctag gatgcgcgct tttgatgtgc tgaagattcc gagcaccgtg tgctatgccg       600
tctccgtctt gcctgtgttg gcggctagct agcgctgagg gttgtggacg gccttgggaa       660
ttaggaaaag aaagatactc gtgacgttga acgtcctgt tctttttctt ttctaagtat        720
tttctattcc aagtctttac tttctgttcc tttcatttca cttcaagtac atcgtcacct       780
ctatcgatct agtgtgagcc gaattgagcc tcctgtcaat gtagcaggag gaactacaga      840
ggttccgact ggtacggaac aaacgaatcg gcgaacgga gagtaggcat gaagttgttg       900
ttgtccaaga tcaaaaagat agaaacgaat atctttcttg ttctgctacc tacattgaaa      960
cggacatgaa aggcgacaat tctagatgaa gacactgcca aaagggaaga agcgctcggc     1020
caccgcagca agaaaggcaa gagagagaag ataagtaaa ttttcgagag aacaaaagaa      1080
atgaatgcag gaaggaagga aggaaggagg ggaggtagtg aaagaacgcg tgacaagatt    1140
tgtaatgaag aacatggcat gaaagaacga acagggggga ctgacgattt gagggactga    1200
tgtgcgcaat tgaatctttt tcatttgcat tgcggctgcg gcggcaaacg aaacaaaaat    1260
aattattcgg cattcacttt gcttgcgttg ttggacaaca taaccataac agaaacaaaa    1320
gcaaggaaac ctagcgcaca cataaacacc aagcaaaatg tctgccgacg cacctatcat    1380
gggaatcaac ggctttggcc gcattggacg cctcgtgttc cgcacggcgt tcagactgg    1440 caacgtcaag gttgtagcca tcaacgatct tcttgatctc gactacattg cctaccttct    1500
caagtacgac tccgttcacg gaccgttcaa gggcactatt gagatcaagg atggcaacct    1560
tgttgtaaac ggcgagaccg tcaaggtcta ctccgagcgc gacccgtcca acatcccctg   1620
```

-continued

```
gggtgagaac ggcgtggagt tcgtctgcga gtctaccggt atcttcacca cagccgagaa    1680
gtgccaggct caccttcgcg gtggcgccaa gcgtgtcatt atctctgctc ctcccaagga    1740
tgacacccct atgtttgtca tgggtgtcaa caacgaggac tacgatggcg aggacattac    1800
ctctaacgcc tcctgcacca ctaactgtct cgccccgctt gccaaggtca tcaacgataa    1860
ctttggcatt gtcgagggtc tcatgaccac cgtccacgcc atgactgcca accagcttac    1920
tgttgatggc ccctccaagg gtggaaagga ctggcgtgcc ggccgctctg ctggcgccaa    1980
cgtaatcccc tccagcactg gtgctgccaa ggctgtcggc aaggtcatcc ctgccctcaa    2040
cggcaagctc accggcatgg ccttccgtgt ccccacccct gatgtcagtg ttgttgatct    2100
tacctgcaag atcgagaagc ccaacagcta cgaggagatc aagaaggtcc tcaaggctgc    2160
ctccgagaac gagctcaagg gtatccttgg ttacactgag gacgccgtgg tgtccaacga    2220
cttcgtcggc aacaccaact ccagcatctt tgacgctgac gccggtatca tgcttaacga    2280
caccttcgtc aagctcatca gctggtacga taacgagcgc ggctactcca cccgcctcac    2340
tgacctcgcc tgctacatca agtctaccgg caagtaaatg tacccaatac acaccggta    2400 gcttctcgcg gcggctgaca agaaagattg tttttacaca tttcgaggca ttgatgaccc    2460
ttatcgacct atcgtctcag atcataaaat gcacgagcat gaagtacgcg tgttgtgact    2520
tgcttgcgtc ccaccttcta gatggctttc ttcttttcaa gtgattaaaa caccacagta    2580
gatgaggact cttagtaagc actgaagaag cgagtaaata gccctcatcc cgtttccctc    2640
ttttctaaca cactttgttt ggaattctaa aatatctttt atcatctctt ttcattcaca    2700
aaactagtat ttctgcatta gaaatcatta tcctatctgg cactttcact ctgacaagaa    2760
cttgccgtac atggcggatc ctggcaatca ttttacttgt acagaccaa gactttgtga    2820 gtcagtaaat agtaaagaaa tgcagaataa tcattagata attgcaaaac cctgatcttc    2880
aaaatgttat atcacaagta cctaccaaga catttgtatc ttcttttttgt cttatgcatt    2940 tttatttccc ttagcgcaat taaaaatatt aaataactga cgactctttt cttaaggatt    3000
cgcggtttgc tagttgcact attgaaaaga gcacggtatt aatttcatag tttttacttg    3060
ttggcaatct cagcaaacat gggttttaat tttaaaatta aataatactt gtgttagact    3120
caaaagatac ctatcaaacc cttagggctc atcgtcaaca tttgcaaatt aaaacgattc    3180
agctcctttg gtacggtcat gtctgttttct gatgcactga aaaaccttgg acgaacgaca    3240
catcttattt tcattaggac atctaaaaaa cgttgtaaag agtatacaat aagcataaaa    3300
aaggagaaga gaaaaagaa agacatacat ggttctgctc ttctagtgct tcaag          3355
```

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
ccaacctggt tgatcctgcc agta                                            24

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic -continued

DNA

<400> SEQUENCE: 12
cattcaagtt tctgccctat c                                            21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
caggctccct ctccggaatc                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gcagccgcgg taattccagc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
actacgagct ttttaactgg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
gtcagaggtg aaattcttgg                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tccttggtaa atgctttcgc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ggattgacag attgagagct                                              20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
aactaagaac ggccatgcac c                                            21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
aggtctgtga tgcccttaga                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
cgtttactag gaattcctcg                                              20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
ccttgttacg acttcacctt cctct                                        25

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
tacactgatg ggttcatcgg                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
cccgttatag tcaccgtagt                                                    20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
gctcctcgcg ctgtgttccc                                                    20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
gaagcacttg cggtggacaa t                                                  21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
accaccactg gtcacctgat                                                    20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
acgttgaagc ccacgttgtc                                                    20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
ggtatcaacg gctttggccg ca                                                 22

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
accttgccca cagccttggc                                           20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
gacaacggtt ccggtatgtg c                                         21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
ggttatcatg gtcggcatgg                                           20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
accaccactg gtcacctgat                                           20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
ctcaaggccg agcgtgagcg                                           20

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
aacggctttg gccgcatcgg tcg                                       23

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
gcctcctgca ccactaactg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
agcgaggcgc atctcctcgt                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38
acgcggagct cgttgtagaa                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39
ggtcacgata ccgtgctcaa                                               20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
gtactcagtg aaggactcaa cg                                            22

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41
cgtagccagc gcggatctca                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
ggcaacatcg gcctgggagg                                               20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
accttgccca cagccttggc                                              20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
ccagcacgcc agtcctttcc                                              20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
ccatccttga tctcaatagt                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
ggccgtgacc tcactgacta                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 47
agcgaggcgc atctcctcgt                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 48
ttggcttcaa cgtcaagaac                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 49
cgtagccagc gcggatctca                                                 20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 50
gacgcctcgt gttccgcacg                                                 20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 51
ccatccttga tctcaatagt                                                 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 52
atctccaagc aggagtacga                                                 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 53
acgcggagct cgttgtagaa                                                 20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 54
ggtgtcatca aggaggttga                                                 20

```
<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 55
ggcaacatcg gcctgggagg                                              20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 56
ctcatcagct ggtacgataa                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 57
ccatccttga tctcaatagt                                              20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 58
tgaacttcgt cgtcagccat                                              20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 59
tccaccgcaa gtgcttctaa                                              20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 60
tgtgcgtcta gtccaacctt                                              20

<210> SEQ ID NO 61
```

<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 61
ttggaagacg ctcctagtag                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 62
gacttcaact atgtccaggc                                                  20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 63
gtagtcagag gtactgagtt                                                  20

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 64
catgtggtta tgtagaacgg ca                                               22

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 65
agtatctcgt gaaagcggga                                                  20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 66
tgctccttcg tcttgcccat                                                  20

<210> SEQ ID NO 67
<211> LENGTH: 20

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 67
tatgaagcta ggatgtgcgt                                                 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 68
cacctacctt ggctcctcgt                                                 20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 69
cgatatcgca actgtgtcga                                                 20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 70
gaaaacgttg gagagcctga                                                 20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 71
acagtgacgg tatctctgct                                                 20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 72
accgtaacgg ccataagaag                                                 20

<210> SEQ ID NO 73
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      DNA

<400> SEQUENCE: 73
ataggtgcgt cggcagacat                                              20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 74
taagcactga agaagcgagt                                              20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 75
cgtaccagtc ggaacctctg                                              20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 76
cttagggctc atcgtcaaca                                              20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 77
acagcacgcc ttacttacct                                              20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 78
ccttcaatcc taaacaccat gc                                           22

<210> SEQ ID NO 79
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      DNA

<400> SEQUENCE: 79
tgaggagaac tgcaagcacc                                                   20

<210> SEQ ID NO 80
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 80
tcgagctcgg taccccttca tactctcgca tttcc                                  35

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 81
ttggccattt tgctagttgg gtgcttgttc tt                                     32

<210> SEQ ID NO 82
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 82
tcgagctcgg taccctcatg ctcctttccc gccaa                                  35

<210> SEQ ID NO 83
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 83
ttggccattt tgtttggtgc tagtagcttc ga                                     32

<210> SEQ ID NO 84
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 84
tcgagctcgg taccccttgat cttgtgaggg ctcca                                 35

<210> SEQ ID NO 85
<211> LENGTH: 32
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 85
ttggccattt tgcttggtgt ttatgtgtgc gc                                32

<210> SEQ ID NO 86
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 86
ctagcaaaat ggccaagttg accagtgccg tt                                32

<210> SEQ ID NO 87
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 87
caaacaaaat ggccaagttg accagtgccg tt                                32

<210> SEQ ID NO 88
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 88
caagcaaaat ggccaagttg accagtgccg tt                                32

<210> SEQ ID NO 89
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 89
ctctagagga tcccctcagt cctgctcctc ggcca                             35

<210> SEQ ID NO 90
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 90
agagtcgaca ttggagtgat ggaatgccc                                    29

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic

DNA

<400> SEQUENCE: 91
cttgcatgct gttgaaagag ctgaggcca                                29

<210> SEQ ID NO 92
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 92
agagtcgacg tggtttgacc tcttatact                                29

<210> SEQ ID NO 93
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 93
cttgcatgcg tttcccaact cacgttgtg                                29

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 94
agagtcgaca tgtacccaat accacaccg                                29

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 95
cttgcatgcc ttgaagcact agaagagca                                29

<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 96
cggggtaccc cagtagtcat atgctcgtc                                29

<210> SEQ ID NO 97
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

```
<400> SEQUENCE: 97
cggggtaccc cttgttacga cttcacctt                                         29

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 98
taccggttca actggtcacg gc                                                22

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 99
tcagtcctgc tcctcttcca                                                   20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 100
cgcaggttca cctacggaaa                                                   20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 101
tcagtcctgc tcctcttcca                                                   20

<210> SEQ ID NO 102
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 102
atgattacga attcgaatga ctggcttcaa gtttg                                  35

<210> SEQ ID NO 103
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA
```

-continued

<400> SEQUENCE: 103
gacatgttca ttttgtttgg tgctagtagc tt                                     32

<210> SEQ ID NO 104
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 104
caaacaaaat gaacatgtca gtgttgactt ta                                     32

<210> SEQ ID NO 105
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 105
caaaccacct actcggcctt cgtcgctttc tt                                     32

<210> SEQ ID NO 106
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 106
ccgagtaggt ggtttgacct cttatacttg atcga                                  35

<210> SEQ ID NO 107
<211> LENGTH: 37
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 107
gattgacaga ttgagctctc aaacatacaa aagaatt                                37

<210> SEQ ID NO 108
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 108
accacttaca ttttgtttgg tgctagtagc tt                                     32

<210> SEQ ID NO 109
<211> LENGTH: 35
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 109
acaaaatgta agtggtttga cctcttatac ttgat                                                      35

<210> SEQ ID NO 110
<211> LENGTH: 376
<212> TYPE: PRT
<213> ORGANISM: Schizochytrium sp.

<400> SEQUENCE: 110

| | | | | | | | | | | | | | | |
|---|---|---|---|---|---|---|---|---|---|---|---|---|---|---|
| Met | Ala | Asp | Asp | Glu | Val | Gln | Ala | Leu | Val | Ile | Asp | Asn | Gly | Ser | Gly |
| 1 | | | | 5 | | | | | 10 | | | | | 15 | |
| Met | Cys | Lys | Ala | Gly | Phe | Ala | Gly | Asp | Asp | Ala | Pro | Arg | Ala | Val | Phe |
| | | | 20 | | | | | 25 | | | | | 30 | | |
| Pro | Ser | Ile | Val | Gly | Arg | Pro | Lys | His | Pro | Gly | Ile | Met | Val | Gly | Met |
| | | | 35 | | | | | 40 | | | | | 45 | | |
| Asp | Gln | Lys | Asp | Ala | Tyr | Val | Gly | Asp | Glu | Ala | Gln | Ser | Lys | Arg | Gly |
| | | 50 | | | | | 55 | | | | | 60 | | | |
| Val | Leu | Thr | Leu | Lys | Tyr | Pro | Ile | Glu | His | Gly | Ile | Val | Thr | Asn | Trp |
| 65 | | | | | 70 | | | | | 75 | | | | | 80 |
| Asp | Asp | Met | Glu | Lys | Ile | Trp | His | His | Thr | Phe | Tyr | Asn | Glu | Leu | Arg |
| | | | | 85 | | | | | 90 | | | | | 95 | |
| Val | Ala | Pro | Glu | Glu | His | Pro | Val | Leu | Leu | Thr | Glu | Ala | Pro | Leu | Asn |
| | | | 100 | | | | | 105 | | | | | 110 | | |
| Pro | Lys | Ala | Asn | Arg | Glu | Arg | Met | Thr | Gln | Ile | Met | Phe | Glu | Thr | Phe |
| | | | 115 | | | | | 120 | | | | | 125 | | |
| Asn | Val | Pro | Ala | Met | Tyr | Val | Asn | Ile | Gln | Ala | Val | Leu | Ser | Leu | Tyr |
| | | 130 | | | | | 135 | | | | | 140 | | | |
| Ala | Ser | Gly | Arg | Thr | Thr | Gly | Ala | Val | Leu | Asp | Ser | Gly | Asp | Gly | Val |
| 145 | | | | | 150 | | | | | 155 | | | | | 160 |
| Thr | His | Thr | Val | Pro | Ile | Tyr | Glu | Gly | Tyr | Ala | Leu | Pro | His | Ala | Val |
| | | | | 165 | | | | | 170 | | | | | 175 | |
| Leu | Arg | Ile | Asp | Leu | Ala | Gly | Arg | Asp | Leu | Thr | Asp | Tyr | Met | Met | Lys |
| | | | 180 | | | | | 185 | | | | | 190 | | |
| Ile | Leu | Thr | Glu | Arg | Gly | Tyr | Ser | Phe | Thr | Thr | Thr | Ala | Glu | Arg | Glu |
| | | | 195 | | | | | 200 | | | | | 205 | | |
| Ile | Val | Arg | Asp | Ile | Lys | Glu | Lys | Leu | Ala | Tyr | Val | Ala | Gln | Asp | Phe |
| | | 210 | | | | | 215 | | | | | 220 | | | |
| Asp | Glu | Glu | Met | Arg | Leu | Ala | Ala | Glu | Ser | Ser | Ala | Leu | Glu | Lys | Ser |
| 225 | | | | | 230 | | | | | 235 | | | | | 240 |
| Tyr | Glu | Leu | Pro | Asp | Gly | Asn | Phe | Ile | Thr | Ile | Gly | Asn | Glu | Arg | Phe |
| | | | | 245 | | | | | 250 | | | | | 255 | |
| Arg | Ala | Pro | Arg | Phe | Leu | Phe | Gln | Pro | Ser | Phe | Ile | Gly | Lys | Glu | Ala |
| | | | 260 | | | | | 265 | | | | | 270 | | |
| Gln | Gly | Val | His | Asp | Thr | Met | Phe | Gln | Thr | Ile | Met | Lys | Cys | Asp | Val |
| | | | 275 | | | | | 280 | | | | | 285 | | |
| Asp | Ile | Arg | Lys | Asp | Leu | Tyr | Ala | Asn | Ile | Val | Met | Ser | Gly | Gly | Ser |
| | | 290 | | | | | 295 | | | | | 300 | | | |
| Thr | Met | Tyr | Glu | Gly | Leu | Ala | Ala | Arg | Leu | Glu | Lys | Glu | Met | Ile | Ala |
| 305 | | | | | 310 | | | | | 315 | | | | | 320 |
| Leu | Ala | Pro | Ser | Thr | Met | Lys | Ile | Lys | Val | Val | Ala | Pro | Pro | Glu | Arg |
| | | | | 325 | | | | | 330 | | | | | 335 | |
| Lys | Tyr | Ser | Val | Trp | Ile | Gly | Gly | Ser | Ile | Leu | Ala | Ser | Leu | Ser | Thr |
| | | | 340 | | | | | 345 | | | | | 350 | | |
| Phe | Gln | Gln | Met | Trp | Ile | Ser | Lys | Gln | Glu | Tyr | Asp | Glu | Ser | Gly | Pro |
| | | | 355 | | | | | 360 | | | | | 365 | | |

```
Ser Ile Val His Arg Lys Cys Phe
    370                 375
```

<210> SEQ ID NO 111
<211> LENGTH: 376
<212> TYPE: PRT
<213> ORGANISM: Phytophthora brassicae

<400> SEQUENCE: 111

```
Met Ala Asp Glu Asp Val Gln Ala Leu Val Val Asp Asn Gly Ser Gly
1               5                   10                  15

Met Cys Lys Ala Gly Phe Ala Gly Asp Asp Ala Pro Arg Ala Val Phe
                20                  25                  30

Pro Ser Ile Val Gly Arg Pro Lys His Leu Gly Ile Met Val Gly Met
            35                  40                  45

Asp Gln Lys Asp Ala Tyr Val Gly Asp Glu Ala Gln Ser Lys Arg Gly
        50                  55                  60

Val Leu Thr Leu Lys Tyr Pro Ile Glu His Gly Ile Val Thr Asn Trp
65                  70                  75                  80

Asp Asp Met Glu Lys Ile Trp His His Thr Phe Tyr Asn Glu Leu Arg
                85                  90                  95

Val Ala Pro Glu Glu His Pro Val Leu Leu Thr Glu Ala Pro Leu Asn
            100                 105                 110

Pro Lys Ala Asn Arg Glu Arg Met Thr Gln Ile Met Phe Glu Thr Phe
        115                 120                 125

Asn Val Pro Ala Met Tyr Val Asn Ile Gln Ala Val Leu Ser Leu Tyr
    130                 135                 140

Ala Ser Gly Arg Thr Thr Gly Cys Val Leu Asp Ser Gly Asp Gly Val
145                 150                 155                 160

Ser His Thr Val Pro Ile Tyr Glu Gly Tyr Ala Leu Pro His Ala Ile
                165                 170                 175

Val Arg Leu Asp Leu Ala Gly Arg Asp Leu Thr Asp Tyr Met Met Lys
            180                 185                 190

Ile Leu Thr Glu Arg Gly Tyr Ser Phe Thr Thr Ala Glu Arg Glu
        195                 200                 205

Ile Val Arg Asp Ile Lys Glu Lys Leu Thr Tyr Ile Ala Leu Asp Phe
    210                 215                 220

Asp Gln Glu Met Lys Thr Ala Ala Glu Ser Ser Gly Leu Glu Lys Ser
225                 230                 235                 240

Tyr Glu Leu Pro Asp Gly Asn Val Ile Val Ile Gly Asn Glu Arg Phe
                245                 250                 255

Arg Thr Pro Glu Val Leu Phe Gln Pro Ser Leu Ile Gly Lys Glu Ala
            260                 265                 270

Ser Gly Ile His Asp Cys Thr Phe Gln Thr Ile Met Lys Cys Asp Val
        275                 280                 285

Asp Ile Arg Lys Asp Leu Tyr Cys Asn Ile Val Leu Ser Gly Gly Thr
    290                 295                 300

Thr Met Tyr Pro Gly Val Gly Glu Arg Met Thr Lys Glu Leu Thr Ala
305                 310                 315                 320

Leu Ala Pro Ser Thr Met Lys Ile Lys Val Val Ala Pro Pro Glu Arg
                325                 330                 335

Lys Tyr Ser Val Trp Ile Gly Gly Ser Ile Leu Ser Ser Leu Ser Thr
            340                 345                 350

Phe Gln Gln Met Trp Ile Ser Lys Ala Glu Tyr Asp Glu Ser Gly Pro
```

```
                355                 360                 365
Ser Ile Val His Arg Lys Cys Phe
    370                 375

<210> SEQ ID NO 112
<211> LENGTH: 375
<212> TYPE: PRT
<213> ORGANISM: Fucus distichus

<400> SEQUENCE: 112

Met Ala Asp Glu Asp Val Gln Ala Leu Val Asp Asn Gly Ser Gly
1               5                   10                  15

Met Cys Lys Ala Gly Phe Gly Asp Asp Ala Pro Arg Ala Val Phe Pro
                20                  25                  30

Ser Ile Val Gly Arg Pro Lys His Pro Gly Ile Met Val Gly Met Asp
            35                  40                  45

Gln Lys Asp Ala Tyr Val Gly Asp Glu Ala Gln Ser Lys Arg Gly Val
50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Val Pro Leu Asn Pro
            100                 105                 110

Lys Ala Asn Lys Glu Arg Met Thr Gln Ile Met Phe Glu Thr Phe Asn
            115                 120                 125

Val Leu Ala Met Tyr Val Asn Ile Gln Ala Val Leu Ser Leu Tyr Ala
130                 135                 140

Ser Gly Ser Thr Thr Gly Cys Val Leu Asp Ser Gly Asp Gly Val Ser
145                 150                 155                 160

His Thr Val Pro Ile Tyr Glu Gly Tyr Ala Leu Pro His Ala Ile Asn
                165                 170                 175

Arg Leu Asp Leu Ala Gly Arg Asp Leu Thr Asp Asn Leu Met Lys Val
            180                 185                 190

Leu Thr Glu Arg Gly Tyr Ser Phe Thr Thr Thr Arg Glu Arg Glu Ile
            195                 200                 205

Val Arg Asp Ile Arg Glu Lys Leu Thr Tyr Val Ala Leu Asp Phe Asp
210                 215                 220

Gln Glu Met Lys Thr Ala Gly Glu Ser Ser Gln Leu Glu Lys Ser Tyr
225                 230                 235                 240

Glu Leu Pro Asp Gly Asn Val Ile Val Ile Gly Asn Glu Arg Phe Arg
                245                 250                 255

Cys Pro Glu Val Leu Phe Gln Pro Ser Phe Ile Gly Met Glu Ser Ser
            260                 265                 270

Gly Ile His Asp Cys Thr Phe Lys Thr Ile Met Lys Cys Asp Val Asp
            275                 280                 285

Ile Arg Lys Asp Leu Tyr Gly Asn Ile Val Leu Ser Gly Gly Thr Thr
290                 295                 300

Met Phe Pro Gly Ile Gly Glu Arg Met Thr Lys Glu Leu Thr Ala Leu
305                 310                 315                 320

Ala Pro Ser Thr Met Lys Ile Lys Val Val Ala Pro Pro Glu Arg Lys
                325                 330                 335

Tyr Ser Val Trp Ile Gly Gly Ser Ile Leu Ala Ser Leu Ser Thr Phe
            340                 345                 350
```

Gln Gln Met Trp Ile Ser Lys Ala Glu Tyr Asp Glu Ser Gly Pro Ser
        355                 360                 365

Ile Val His Arg Lys Cys Phe
    370                 375

<210> SEQ ID NO 113
<211> LENGTH: 375
<212> TYPE: PRT
<213> ORGANISM: Saccharomyces cerevisiae

<400> SEQUENCE: 113

Met Asp Ser Glu Val Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Ile Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Arg Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Met Asn Pro
            100                 105                 110

Lys Ser Asn Arg Glu Lys Met Thr Gln Ile Met Phe Glu Thr Phe Asn
        115                 120                 125

Val Pro Ala Phe Tyr Val Ser Ile Gln Ala Val Leu Ser Leu Tyr Ser
    130                 135                 140

Ser Gly Arg Thr Thr Gly Ile Val Leu Asp Ser Gly Asp Gly Val Thr
145                 150                 155                 160

His Val Val Pro Ile Tyr Ala Gly Phe Ser Leu Pro His Ala Ile Leu
                165                 170                 175

Arg Ile Asp Leu Ala Gly Arg Asp Leu Thr Asp Tyr Leu Met Lys Ile
            180                 185                 190

Leu Ser Glu Arg Gly Tyr Ser Phe Ser Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Met Gln Thr Ala Ala Gln Ser Ser Ser Ile Glu Lys Ser Tyr
225                 230                 235                 240

Glu Leu Pro Asp Gly Gln Val Ile Thr Ile Gly Asn Glu Arg Phe Arg
                245                 250                 255

Ala Pro Glu Ala Leu Phe His Pro Ser Val Leu Gly Leu Glu Ser Ala
            260                 265                 270

Gly Ile Asp Gln Thr Thr Tyr Asn Ser Ile Met Lys Cys Asp Val Asp
        275                 280                 285

Val Arg Lys Glu Leu Tyr Gly Asn Ile Val Met Ser Gly Gly Thr Thr
    290                 295                 300

Met Phe Pro Gly Ile Ala Glu Arg Met Gln Lys Glu Ile Thr Ala Leu
305                 310                 315                 320

Ala Pro Ser Ser Met Lys Val Lys Ile Ile Ala Pro Pro Glu Arg Lys
                325                 330                 335

Tyr Ser Val Trp Ile Gly Gly Ser Ile Leu Ala Ser Leu Thr Thr Phe
            340                 345                 350

```
Gln Gln Met Trp Ile Ser Lys Gln Glu Tyr Asp Glu Ser Gly Pro Ser
        355                 360                 365

Ile Val His His Lys Cys Phe
    370                 375

<210> SEQ ID NO 114
<211> LENGTH: 376
<212> TYPE: PRT
<213> ORGANISM: Artificial Sequence
<220> FEATURE:
<223> OTHER INFORMATION: Consensus sequence derived from various
      organisms
<220> FEATURE:
<221> NAME/KEY: misc_feature
<222> LOCATION: (4)..(4)
<223> OTHER INFORMATION: Xaa can be Asp, Glu, or Ser
<220> FEATURE:
<221> NAME/KEY: misc_feature
<222> LOCATION: (5)..(5)
<223> OTHER INFORMATION: Xaa can be Asn, Asp, Gln, or Glu
<220> FEATURE:
<221> NAME/KEY: misc_feature
<222> LOCATION: (11)..(11)
<223> OTHER INFORMATION: Xaa can be Ile or Val
<220> FEATURE:
<221> NAME/KEY: misc_feature
<222> LOCATION: (42)..(42)
<223> OTHER INFORMATION: Xaa can be Pro, Leu, or Gln
<220> FEATURE:
<221> NAME/KEY: misc_feature
<222> LOCATION: (65)..(65)
<223> OTHER INFORMATION: Xaa can be Ile or Val
<220> FEATURE:
<221> NAME/KEY: misc_feature
<222> LOCATION: (111)..(111)
<223> OTHER INFORMATION: Xaa can be Leu or Met
<220> FEATURE:
<221> NAME/KEY: misc_feature
<222> LOCATION: (152)..(152)
<223> OTHER INFORMATION: Xaa can be Ala, Cys, or Ile
<220> FEATURE:
<221> NAME/KEY: misc_feature
<222> LOCATION: (170)..(170)
<223> OTHER INFORMATION: Xaa can be Phe or Tyr
<220> FEATURE:
<221> NAME/KEY: misc_feature
<222> LOCATION: (176)..(176)
<223> OTHER INFORMATION: Xaa can be Ile or Val
<220> FEATURE:
<221> NAME/KEY: misc_feature
<222> LOCATION: (190)..(190)
<223> OTHER INFORMATION: Xaa can be Leu or Met
<220> FEATURE:
<221> NAME/KEY: misc_feature
<222> LOCATION: (193)..(193)
<223> OTHER INFORMATION: Xaa can be Ile or Val
<220> FEATURE:
<221> NAME/KEY: misc_feature
<222> LOCATION: (218)..(218)
<223> OTHER INFORMATION: Xaa can be Ala, Thr, or Cys
<220> FEATURE:
<221> NAME/KEY: misc_feature
<222> LOCATION: (220)..(220)
<223> OTHER INFORMATION: Xaa can be Ile or Val
<220> FEATURE:
<221> NAME/KEY: misc_feature
<222> LOCATION: (225)..(226)
<223> OTHER INFORMATION: Xaa can be Asn, Asp, Gln, or Glu
<220> FEATURE:
<221> NAME/KEY: misc_feature
<222> LOCATION: (229)..(229)
<223> OTHER INFORMATION: Xaa can be Arg, Lys, or Gln
<220> FEATURE:
<221> NAME/KEY: misc_feature
<222> LOCATION: (233)..(233)
<223> OTHER INFORMATION: Xaa can be Asn, Asp, Gln, or Glu
```

```
<220> FEATURE:
<221> NAME/KEY: misc_feature
<222> LOCATION: (236)..(236)
<223> OTHER INFORMATION: Xaa can be Ala, Gly, Gln, or Ser
<220> FEATURE:
<221> NAME/KEY: misc_feature
<222> LOCATION: (247)..(247)
<223> OTHER INFORMATION: Xaa can be Asn, Asp, Gln, or Glu
<220> FEATURE:
<221> NAME/KEY: misc_feature
<222> LOCATION: (261)..(261)
<223> OTHER INFORMATION: Xaa can be Phe, Val, or Ala
<220> FEATURE:
<221> NAME/KEY: misc_feature
<222> LOCATION: (267)..(267)
<223> OTHER INFORMATION: Xaa can be Phe, Leu, or Val
<220> FEATURE:
<221> NAME/KEY: misc_feature
<222> LOCATION: (270)..(270)
<223> OTHER INFORMATION: Xaa can be Lys, Met, or Leu
<220> FEATURE:
<221> NAME/KEY: misc_feature
<222> LOCATION: (273)..(273)
<223> OTHER INFORMATION: Xaa can be Gln, Ser, or Ala
<220> FEATURE:
<221> NAME/KEY: misc_feature
<222> LOCATION: (275)..(275)
<223> OTHER INFORMATION: Xaa can be Ile or Val
<220> FEATURE:
<221> NAME/KEY: misc_feature
<222> LOCATION: (277)..(277)
<223> OTHER INFORMATION: Xaa can be Ile or Val
<220> FEATURE:
<221> NAME/KEY: misc_feature
<222> LOCATION: (280)..(280)
<223> OTHER INFORMATION: Xaa can be Phe or Tyr
<220> FEATURE:
<221> NAME/KEY: misc_feature
<222> LOCATION: (281)..(281)
<223> OTHER INFORMATION: Xaa can be Gln, Lys, or Asn
<220> FEATURE:
<221> NAME/KEY: misc_feature
<222> LOCATION: (290)..(290)
<223> OTHER INFORMATION: Xaa can be Ile or Val
<220> FEATURE:
<221> NAME/KEY: misc_feature
<222> LOCATION: (293)..(293)
<223> OTHER INFORMATION: Xaa can be Asn, Asp, Gln, or Glu
<220> FEATURE:
<221> NAME/KEY: misc_feature
<222> LOCATION: (300)..(300)
<223> OTHER INFORMATION: Xaa can be Leu or Met
<220> FEATURE:
<221> NAME/KEY: misc_feature
<222> LOCATION: (307)..(307)
<223> OTHER INFORMATION: Xaa can be Phe or Tyr
<220> FEATURE:
<221> NAME/KEY: misc_feature
<222> LOCATION: (314)..(314)
<223> OTHER INFORMATION: Xaa can be Leu or Met
<220> FEATURE:
<221> NAME/KEY: misc_feature
<222> LOCATION: (315)..(315)
<223> OTHER INFORMATION: Xaa can be Glu, Thr, or Gln
<220> FEATURE:
<221> NAME/KEY: misc_feature
<222> LOCATION: (318)..(318)
<223> OTHER INFORMATION: Xaa can be Met, Leu, or Ile
<220> FEATURE:
<221> NAME/KEY: misc_feature
<222> LOCATION: (328)..(328)
<223> OTHER INFORMATION: Xaa can be Ile or Val
<220> FEATURE:
<221> NAME/KEY: misc_feature
<222> LOCATION: (330)..(331)
<223> OTHER INFORMATION: Xaa can be Ile or Val

<400> SEQUENCE: 114
```

Met Ala Asp Xaa Xaa Val Gln Ala Leu Val Xaa Asp Asn Gly Ser Gly
1               5                   10                  15

Met Cys Lys Ala Gly Phe Ala Gly Asp Asp Ala Pro Arg Ala Val Phe
            20                  25                  30

Pro Ser Ile Val Gly Arg Pro Lys His Xaa Gly Ile Met Val Gly Met
        35                  40                  45

Asp Gln Lys Asp Ala Tyr Val Gly Asp Glu Ala Gln Ser Lys Arg Gly
    50                  55                  60

Xaa Leu Thr Leu Lys Tyr Pro Ile Glu His Gly Ile Val Thr Asn Trp
65              70                  75                  80

Asp Asp Met Glu Lys Ile Trp His His Thr Phe Tyr Asn Glu Leu Arg
            85                  90                  95

Val Ala Pro Glu Glu His Pro Val Leu Leu Thr Glu Ala Pro Xaa Asn
        100                 105                 110

Pro Lys Ala Asn Arg Glu Arg Met Thr Gln Ile Met Phe Glu Thr Phe
    115                 120                 125

Asn Val Pro Ala Met Tyr Val Asn Ile Gln Ala Val Leu Ser Leu Tyr
    130                 135                 140

Ala Ser Gly Arg Thr Thr Gly Xaa Val Leu Asp Ser Gly Asp Gly Val
145             150                 155                 160

Thr His Thr Val Pro Ile Tyr Glu Gly Xaa Ala Leu Pro His Ala Xaa
            165                 170                 175

Leu Arg Ile Asp Leu Ala Gly Arg Asp Leu Thr Asp Tyr Xaa Met Lys
            180                 185                 190

Xaa Leu Thr Glu Arg Gly Tyr Ser Phe Thr Thr Ala Glu Arg Glu
            195                 200                 205

Ile Val Arg Asp Ile Lys Glu Lys Leu Xaa Tyr Xaa Ala Leu Asp Phe
        210                 215                 220

Xaa Xaa Glu Met Xaa Thr Ala Ala Xaa Ser Ser Xaa Leu Glu Lys Ser
225             230                 235                 240

Tyr Glu Leu Pro Asp Gly Xaa Val Ile Thr Ile Gly Asn Glu Arg Phe
            245                 250                 255

Arg Ala Pro Glu Xaa Leu Phe Gln Pro Ser Xaa Ile Gly Xaa Glu Ser
            260                 265                 270

Xaa Gly Xaa His Xaa Thr Thr Xaa Xaa Thr Ile Met Lys Cys Asp Val
            275                 280                 285

Asp Xaa Arg Lys Xaa Leu Tyr Gly Asn Ile Val Xaa Ser Gly Gly Thr
    290                 295                 300

Thr Met Xaa Pro Gly Ile Ala Glu Arg Xaa Xaa Lys Glu Xaa Thr Ala
305             310                 315                 320

Leu Ala Pro Ser Thr Met Lys Xaa Lys Xaa Xaa Ala Pro Pro Glu Arg
            325                 330                 335

Lys Tyr Ser Val Trp Ile Gly Gly Ser Ile Leu Ala Ser Leu Ser Thr
            340                 345                 350

Phe Gln Gln Met Trp Ile Ser Lys Gln Glu Tyr Asp Glu Ser Gly Pro
            355                 360                 365

Ser Ile Val His Arg Lys Cys Phe
            370                 375

<210> SEQ ID NO 115
<211> LENGTH: 434
<212> TYPE: PRT
<213> ORGANISM: Schizochytrium sp.

<400> SEQUENCE: 115

-continued

```
Met Gly Lys Thr Lys Glu His Val Asn Leu Val Ile Gly His Val
 1               5                  10                  15

Asp Ala Gly Lys Ser Thr Thr Thr Gly His Leu Ile Tyr Lys Cys Gly
            20                  25                  30

Gly Ile Asp Lys Arg Thr Ile Glu Lys Phe Glu Lys Glu Ala Ala Glu
                35                  40                  45

Leu Gly Lys Gly Ser Phe Lys Tyr Ala Trp Val Leu Asp Lys Leu Lys
     50                  55                  60

Ala Glu Arg Glu Arg Gly Ile Thr Ile Asp Ile Ala Leu Trp Lys Phe
 65                  70                  75                  80

Glu Ser Pro Lys Phe Asp Phe Thr Val Ile Asp Ala Pro Gly His Arg
                 85                  90                  95

Asp Phe Ile Lys Asn Met Ile Thr Gly Thr Ser Gln Ala Asp Val Ala
                100                 105                 110

Val Leu Val Ile Asp Ser Ser Gln Gly Gly Phe Glu Ala Gly Ile Ala
             115                 120                 125

Lys Asp Gly Gln Thr Arg Glu His Ala Leu Leu Ala Phe Thr Leu Gly
130                 135                 140

Ile Gln Gln Ile Ile Val Ala Val Asn Lys Met Asp Asp Lys Thr Thr
145                 150                 155                 160

Met Tyr Ser Glu Ala Arg Phe Asn Glu Ile Val Asn Glu Val Ser Ala
                165                 170                 175

Tyr Leu Ala Lys Val Gly Phe Lys Pro Lys Lys Ile Lys Phe Val Pro
            180                 185                 190

Ile Ser Gly Trp Ala Gly Asp Asn Met Ile Glu Lys Ser Ser Asn Met
        195                 200                 205

Pro Trp Tyr Lys Gly Pro Tyr Leu Leu Glu Ala Leu Asp Asn Ile Lys
    210                 215                 220

Pro Pro Lys Arg Pro Ile Asp Lys Pro Leu Arg Leu Pro Leu Gln Asp
225                 230                 235                 240

Val Tyr Lys Ile Gly Gly Ile Gly Thr Val Pro Val Gly Arg Val Glu
                245                 250                 255

Thr Gly Val Ile Lys Pro Gly Met Thr Ala Tyr Phe Ala Pro Thr Gly
            260                 265                 270

Val Gln Thr Glu Val Lys Ser Val Glu Met His His Glu Ser Ile Pro
        275                 280                 285

Glu Ala Thr Pro Gly Asp Asn Val Gly Phe Asn Val Lys Asn Val Ser
    290                 295                 300

Val Lys Asp Ile Lys Arg Gly Asn Val Cys Gly Asp Ala Lys Asn Asp
305                 310                 315                 320

Pro Pro Arg Gly Ala Asn Ser Phe Leu Ala Gln Val Ile Val Met Gly
                325                 330                 335

His Pro Gly Glu Ile Arg Ala Gly Tyr Ala Pro Val Leu Asp Cys His
            340                 345                 350

Thr Ala His Ile Ala Cys Lys Phe Ala Glu Ile Gln Asn Lys Met Asp
        355                 360                 365

Arg Arg Ser Gly Lys Ile Leu Glu Asp Ala Pro Lys Phe Ile Lys Ser
    370                 375                 380

Gly Asp Ser Ala Met Val Lys Met Ile Pro Ser Lys Lys Met Cys Val
385                 390                 395                 400

Glu Ser Phe Thr Glu Tyr Pro Pro Leu Gly Arg Phe Ala Val Arg Asp
                405                 410                 415
```

Met Arg Val Thr Val Ala Val Gly Val Ile Lys Glu Val Glu Lys Gly
                420                 425                 430

Asp Lys

<210> SEQ ID NO 116
<211> LENGTH: 458
<212> TYPE: PRT
<213> ORGANISM: Saccharomyces cerevisiae

<400> SEQUENCE: 116

Met Gly Lys Glu Lys Ser His Ile Asn Val Val Ile Gly His Val
1               5                   10                  15

Asp Ser Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Ala Glu
                35                  40                  45

Leu Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ala Leu Trp Lys Phe
65              70                  75                  80

Glu Thr Pro Lys Tyr Gln Val Thr Val Ile Asp Ala Pro Gly His Arg
                85                  90                  95

Asp Phe Ile Lys Asn Met Ile Thr Gly Thr Ser Gln Ala Asp Cys Ala
                100                 105                 110

Ile Leu Ile Ile Ala Gly Gly Val Gly Glu Phe Glu Ala Gly Ile Ser
        115                 120                 125

Lys Asp Gly Gln Thr Arg Glu His Ala Leu Leu Ala Phe Thr Leu Gly
    130                 135                 140

Val Arg Gln Leu Ile Val Ala Val Asn Lys Met Asp Ser Val Lys Trp
145                 150                 155                 160

Asp Glu Ser Arg Phe Gln Glu Ile Val Lys Glu Thr Ser Asn Phe Ile
                165                 170                 175

Lys Lys Val Gly Tyr Asn Pro Lys Thr Val Pro Phe Val Pro Ile Ser
                180                 185                 190

Gly Trp Asn Gly Asp Asn Met Ile Glu Ala Thr Thr Asn Ala Pro Trp
        195                 200                 205

Tyr Lys Gly Trp Glu Lys Glu Thr Lys Ala Gly Val Val Lys Gly Lys
    210                 215                 220

Thr Leu Leu Glu Ala Ile Asp Ala Ile Glu Gln Pro Ser Arg Pro Thr
225                 230                 235                 240

Asp Lys Pro Leu Arg Leu Pro Leu Gln Asp Val Tyr Lys Ile Gly Gly
                245                 250                 255

Ile Gly Thr Val Pro Val Gly Arg Val Glu Thr Gly Val Ile Lys Pro
                260                 265                 270

Gly Met Val Val Thr Phe Ala Pro Ala Gly Val Thr Thr Glu Val Lys
        275                 280                 285

Ser Val Glu Met His His Glu Gln Leu Glu Gln Gly Val Pro Gly Asp
    290                 295                 300

Asn Val Gly Phe Asn Val Lys Asn Val Ser Val Lys Glu Ile Arg Arg
305                 310                 315                 320

Gly Asn Val Cys Gly Asp Ala Lys Asn Asp Pro Pro Lys Gly Cys Ala
                325                 330                 335

Ser Phe Asn Ala Thr Val Ile Val Leu Asn His Pro Gly Gln Ile Ser
                340                 345                 350

```
Ala Gly Tyr Ser Pro Val Leu Asp Cys His Thr Ala His Ile Ala Cys
        355                 360                 365

Arg Phe Asp Glu Leu Leu Glu Lys Asn Asp Arg Arg Ser Gly Lys Lys
    370                 375                 380

Leu Glu Asp His Pro Lys Phe Leu Lys Ser Gly Asp Ala Ala Leu Val
385                 390                 395                 400

Lys Phe Val Pro Ser Lys Pro Met Cys Val Glu Ala Phe Ser Glu Tyr
                405                 410                 415

Pro Pro Leu Gly Arg Phe Ala Val Arg Asp Met Arg Gln Thr Val Ala
            420                 425                 430

Val Gly Val Ile Lys Ser Val Asp Lys Thr Glu Lys Ala Ala Lys Val
        435                 440                 445

Thr Lys Ala Ala Gln Lys Ala Ala Lys Lys
        450                 455

<210> SEQ ID NO 117
<211> LENGTH: 432
<212> TYPE: PRT
<213> ORGANISM: Phytophthora infestans

<400> SEQUENCE: 117

Val Ile Gly His Val Asp Ala Gly Lys Ser Thr Thr Gly His Leu
1               5                   10                  15

Ile Tyr Lys Cys Gly Gly Ile Asp Lys Arg Thr Ile Glu Lys Phe Glu
            20                  25                  30

Lys Glu Ala Ala Glu Leu Gly Lys Thr Ser Phe Lys Tyr Ala Trp Val
        35                  40                  45

Leu Asp Asn Leu Lys Ala Glu Arg Glu Arg Gly Ile Thr Ile Asp Ile
    50                  55                  60

Ala Leu Trp Lys Phe Glu Ser Pro Lys Tyr Phe Phe Thr Val Ile Asp
65                  70                  75                  80

Ala Pro Gly His Arg Asp Phe Ile Lys Asn Met Ile Thr Gly Thr Ser
                85                  90                  95

Gln Ala Asp Cys Ala Ile Leu Val Val Ala Ser Gly Val Gly Glu Phe
            100                 105                 110

Glu Ala Gly Ile Ser Lys Glu Gly Gln Thr Arg Glu His Ala Leu Leu
        115                 120                 125

Ala Phe Thr Leu Gly Val Lys Gln Met Val Val Ala Ile Asn Lys Met
    130                 135                 140

Asp Asp Ser Ser Val Met Tyr Gly Gln Ala Arg Tyr Glu Glu Ile Lys
145                 150                 155                 160

Ser Glu Val Thr Thr Tyr Leu Lys Lys Val Gly Tyr Lys Pro Ala Lys
                165                 170                 175

Ile Pro Phe Val Pro Ile Ser Gly Trp Glu Gly Asp Asn Met Ile Asp
            180                 185                 190

Arg Ser Thr Asn Met Pro Trp Tyr Lys Gly Pro Phe Leu Leu Glu Ala
        195                 200                 205

Leu Asp Asn Leu Asn Ala Pro Lys Arg Pro Ser Asp Lys Pro Leu Arg
    210                 215                 220

Leu Pro Leu Gln Asp Val Tyr Lys Ile Gly Gly Ile Gly Thr Val Pro
225                 230                 235                 240

Val Gly Arg Val Glu Thr Gly Val Ile Lys Pro Gly Met Val Ala Thr
                245                 250                 255

Phe Gly Pro Val Gly Leu Ser Thr Glu Val Lys Ser Val Glu Met His
            260                 265                 270
```

His Glu Ser Leu Pro Glu Ala Val Pro Gly Asp Asn Val Gly Phe Asn
            275                 280                 285

Val Lys Asn Val Ser Val Lys Glu Leu Arg Arg Gly Phe Val Ala Ser
        290                 295                 300

Asp Ser Lys Asn Asp Pro Ala Lys Ala Thr Gln Asp Phe Thr Ala Gln
305                 310                 315                 320

Val Ile Val Leu Asn His Pro Gly Gln Ile Gly Asn Gly Tyr Ser Pro
                325                 330                 335

Val Leu Asp Cys His Thr Ala His Val Ala Cys Lys Phe Lys Glu Ile
            340                 345                 350

Thr Glu Lys Met Asp Arg Arg Ser Gly Lys Val Leu Glu Thr Ala Pro
        355                 360                 365

Lys Phe Val Lys Ser Gly Asp Ala Cys Met Val Ile Leu Glu Pro Ser
    370                 375                 380

Lys Pro Met Thr Val Glu Ser Phe Gln Glu Tyr Pro Pro Leu Gly Arg
385                 390                 395                 400

Phe Ala Val Arg Asp Met Arg Gln Thr Val Ala Val Gly Val Ile Lys
                405                 410                 415

Ser Val Asn Lys Lys Glu Ala Ser Gly Lys Gly Ala Lys Lys Lys
            420                 425                 430

<210> SEQ ID NO 118
<211> LENGTH: 434
<212> TYPE: PRT
<213> ORGANISM: Blastocystis hominis

<400> SEQUENCE: 118

Met Gly Lys Glu Lys Pro His Ile Asn Leu Val Val Ile Gly His Val
1               5                   10                  15

Val Ala Gly Lys Ser Thr Thr Thr Gly His Leu Ile Tyr Ala Cys Gly
            20                  25                  30

Gly Ile Asp Lys Arg Thr Ile Glu Arg Phe Glu Glu Gly Gly Gln Arg
        35                  40                  45

Ile Gly Lys Gly Ser Phe Lys Tyr Ala Trp Val Leu Ala Lys Met Lys
    50                  55                  60

Ala Glu Arg Glu Arg Gly Ile Thr Ile Asp Ile Ser Leu Trp Lys Phe
65                  70                  75                  80

Glu Thr Arg Lys Asp Phe Phe Thr Ile Ile Asp Ala Pro Gly His Arg
                85                  90                  95

Asp Phe Ile Lys Asn Met Ile Thr Gly Thr Ser Gln Ala Asp Val Ala
            100                 105                 110

Ile Leu Val Ile Ala Ser Gly Ala Gly Glu Phe Glu Ala Gly Tyr Ser
        115                 120                 125

Lys Asn Gly Gln Thr Arg Glu His Ala Leu Leu Ala Asn Thr Leu Gly
    130                 135                 140

Val Lys Gln Met Ile Val Cys Cys Asn Lys Met Asp Asp Lys Ser Val
145                 150                 155                 160

Asn Tyr Ser Glu Ala Arg Tyr Lys Glu Ile Lys Asn Glu Met Thr Ser
                165                 170                 175

Phe Leu Thr Lys Val Gly Tyr Ala Lys Val Glu Glu Arg Ile Pro Phe
            180                 185                 190

Ile Pro Ile Ser Gly Phe Asn Gly Asp Asn Met Ile Glu His Ser Ala
        195                 200                 205

Asn Met Pro Trp Tyr Lys Gly Pro Thr Leu Leu Glu Ala Leu Asp Asn

-continued

```
                210                 215                 220
Val His Pro Pro Lys Arg Pro Val Asp Lys Pro Leu Arg Leu Pro Leu
225                 230                 235                 240

Gln Asp Val Tyr Lys Ile Gly Gly Ile Gly Thr Val Pro Val Gly Arg
                245                 250                 255

Val Glu Thr Gly Val Leu Lys Pro Gly Met Thr Val Thr Phe Ala Pro
            260                 265                 270

Val Asn Val Ser Thr Glu Val Lys Ser Val Glu Met His His Glu Ser
            275                 280                 285

Ile Pro Gln Ala Leu Pro Gly Asp Asn Val Gly Phe Asn Val Asn Asn
290                 295                 300

Val Ser Val Glu Asp Ile His Arg Gly Asn Val Cys Gly Asp Ala Lys
305                 310                 315                 320

Asn Asp Pro Pro Cys Lys Thr Glu Ser Asp Ala Gln Val Ile Val Met
                325                 330                 335

Asn His Pro Ser Gly Ile Arg Pro Gly Tyr Cys Pro Val Val Asp Cys
            340                 345                 350

His Thr Ala His Ile Ala Cys Lys Phe Glu Lys Ile Met Ser Glu Met
            355                 360                 365

Asp Lys Arg Thr Gly Lys Val Leu Arg Glu Asn Pro Asp Ile Val Lys
            370                 375                 380

Asn Gly Lys Ser Met Met Ala Gln Leu Val Pro Ser Lys Pro Met Cys
385                 390                 395                 400

Val Glu Thr Phe Ser Asp Tyr Pro Pro Leu Gly Arg Phe Ala Val Arg
                405                 410                 415

Asp Met Arg Gln Thr Val Ala Val Gly Ile Ile Lys Ser Thr Val Arg
            420                 425                 430

Ala Lys
```

```
<210> SEQ ID NO 119
<211> LENGTH: 462
<212> TYPE: PRT
<213> ORGANISM: Artificial Sequence
<220> FEATURE:
<223> OTHER INFORMATION: Consensus sequence derived from various
      organisms
<220> FEATURE:
<221> NAME/KEY: misc_feature
<222> LOCATION: (6)..(6)
<223> OTHER INFORMATION: Xaa can be Glu, Ser, or Pro
<220> FEATURE:
<221> NAME/KEY: misc_feature
<222> LOCATION: (63)..(63)
<223> OTHER INFORMATION: Xaa can be Leu or Met
<220> FEATURE:
<221> NAME/KEY: misc_feature
<222> LOCATION: (85)..(85)
<223> OTHER INFORMATION: Xaa can be Phe, Tyr, or Asp
<220> FEATURE:
<221> NAME/KEY: misc_feature
<222> LOCATION: (89)..(89)
<223> OTHER INFORMATION: Xaa can be Ile or Val
<220> FEATURE:
<221> NAME/KEY: misc_feature
<222> LOCATION: (113)..(113)
<223> OTHER INFORMATION: Xaa can be Ile or Val
<220> FEATURE:
<221> NAME/KEY: misc_feature
<222> LOCATION: (115)..(116)
<223> OTHER INFORMATION: Xaa can be Ile or Val
<220> FEATURE:
<221> NAME/KEY: misc_feature
<222> LOCATION: (120)..(120)
<223> OTHER INFORMATION: Xaa can be Gln, Val, or Ala
```

```
<220> FEATURE:
<221> NAME/KEY: misc_feature
<222> LOCATION: (130)..(130)
<223> OTHER INFORMATION: Xaa can be Asn, Asp, Gln, or Glu
<220> FEATURE:
<221> NAME/KEY: misc_feature
<222> LOCATION: (145)..(145)
<223> OTHER INFORMATION: Xaa can be Ile or Val
<220> FEATURE:
<221> NAME/KEY: misc_feature
<222> LOCATION: (149)..(149)
<223> OTHER INFORMATION: Xaa can be Ile or Val
<220> FEATURE:
<221> NAME/KEY: misc_feature
<222> LOCATION: (152)..(152)
<223> OTHER INFORMATION: Xaa can be Val, Ile, or Cys
<220> FEATURE:
<221> NAME/KEY: misc_feature
<222> LOCATION: (161)..(161)
<223> OTHER INFORMATION: Xaa can be Met, Lys, or Asn
<220> FEATURE:
<221> NAME/KEY: misc_feature
<222> LOCATION: (164)..(164)
<223> OTHER INFORMATION: Xaa can be Asn, Asp, Gln, or Glu
<220> FEATURE:
<221> NAME/KEY: misc_feature
<222> LOCATION: (167)..(167)
<223> OTHER INFORMATION: Xaa can be Phe or Tyr
<220> FEATURE:
<221> NAME/KEY: misc_feature
<222> LOCATION: (168)..(168)
<223> OTHER INFORMATION: Xaa can be Asn, Gln, Glu, or Lys
<220> FEATURE:
<221> NAME/KEY: misc_feature
<222> LOCATION: (174)..(174)
<223> OTHER INFORMATION: Xaa can be Val, Thr, or Met
<220> FEATURE:
<221> NAME/KEY: misc_feature
<222> LOCATION: (176)..(176)
<223> OTHER INFORMATION: Xaa can be Ala, Asn, Thr, or Ser
<220> FEATURE:
<221> NAME/KEY: misc_feature
<222> LOCATION: (177)..(177)
<223> OTHER INFORMATION: Xaa can be Phe or Tyr
<220> FEATURE:
<221> NAME/KEY: misc_feature
<222> LOCATION: (179)..(179)
<223> OTHER INFORMATION: Xaa can be Ala, Lys, or Thr
<220> FEATURE:
<221> NAME/KEY: misc_feature
<222> LOCATION: (183)..(183)
<223> OTHER INFORMATION: Xaa can be Phe or Tyr
<220> FEATURE:
<221> NAME/KEY: misc_feature
<222> LOCATION: (184)..(184)
<223> OTHER INFORMATION: Xaa can be Lys, Asn, or Ala
<220> FEATURE:
<221> NAME/KEY: misc_feature
<222> LOCATION: (186)..(186)
<223> OTHER INFORMATION: Xaa, if present, is V
<220> FEATURE:
<221> NAME/KEY: misc_feature
<222> LOCATION: (187)..(187)
<223> OTHER INFORMATION: Xaa, if present, is Glu
<220> FEATURE:
<221> NAME/KEY: misc_feature
<222> LOCATION: (188)..(188)
<223> OTHER INFORMATION: Xaa can be Lys, Ala, or Glu
<220> FEATURE:
<221> NAME/KEY: misc_feature
<222> LOCATION: (189)..(189)
<223> OTHER INFORMATION: Xaa can be Lys, Thr, or Arg
<220> FEATURE:
<221> NAME/KEY: misc_feature
<222> LOCATION: (190)..(190)
<223> OTHER INFORMATION: Xaa can be Ile or Val
<220> FEATURE:
<221> NAME/KEY: misc_feature
<222> LOCATION: (193)..(193)
```

-continued

```
<223> OTHER INFORMATION: Xaa can be Ile or Val
<220> FEATURE:
<221> NAME/KEY: misc_feature
<222> LOCATION: (205)..(205)
<223> OTHER INFORMATION: Xaa can be Asn, Asp, Gln, or Glu
<220> FEATURE:
<221> NAME/KEY: misc_feature
<222> LOCATION: (206)..(206)
<223> OTHER INFORMATION: Xaa can be Lys, Ala, Arg, or His
<220> FEATURE:
<221> NAME/KEY: misc_feature
<222> LOCATION: (208)..(208)
<223> OTHER INFORMATION: Xaa can be Ser, Thr, or Ala
<220> FEATURE:
<221> NAME/KEY: misc_feature
<222> LOCATION: (216)..(216)
<223> OTHER INFORMATION: Xaa, if present, is Trp
<220> FEATURE:
<221> NAME/KEY: misc_feature
<222> LOCATION: (217)..(217)
<223> OTHER INFORMATION: Xaa, if present, is Glu
<220> FEATURE:
<221> NAME/KEY: misc_feature
<222> LOCATION: (218)..(218)
<223> OTHER INFORMATION: Xaa, if present, is Lys
<220> FEATURE:
<221> NAME/KEY: misc_feature
<222> LOCATION: (219)..(219)
<223> OTHER INFORMATION: Xaa, if present, is Glu
<220> FEATURE:
<221> NAME/KEY: misc_feature
<222> LOCATION: (220)..(220)
<223> OTHER INFORMATION: Xaa, if present, is Thr
<220> FEATURE:
<221> NAME/KEY: misc_feature
<222> LOCATION: (221)..(221)
<223> OTHER INFORMATION: Xaa, if present, is Lys
<220> FEATURE:
<221> NAME/KEY: misc_feature
<222> LOCATION: (222)..(222)
<223> OTHER INFORMATION: Xaa, if present, is Ala
<220> FEATURE:
<221> NAME/KEY: misc_feature
<222> LOCATION: (223)..(223)
<223> OTHER INFORMATION: Xaa, if present, is Gly
<220> FEATURE:
<221> NAME/KEY: misc_feature
<222> LOCATION: (224)..(224)
<223> OTHER INFORMATION: Xaa, if present, is Val
<220> FEATURE:
<221> NAME/KEY: misc_feature
<222> LOCATION: (225)..(225)
<223> OTHER INFORMATION: Xaa, if present, is Val
<220> FEATURE:
<221> NAME/KEY: misc_feature
<222> LOCATION: (226)..(226)
<223> OTHER INFORMATION: Xaa, if present, is Lys
<220> FEATURE:
<221> NAME/KEY: misc_feature
<222> LOCATION: (227)..(227)
<223> OTHER INFORMATION: Xaa, if present, is Gly
<220> FEATURE:
<221> NAME/KEY: misc_feature
<222> LOCATION: (237)..(237)
<223> OTHER INFORMATION: Xaa can be Ile, Leu, or Val
<220> FEATURE:
<221> NAME/KEY: misc_feature
<222> LOCATION: (238)..(238)
<223> OTHER INFORMATION: Xaa can be Lys, Glu, Asn, or His
<220> FEATURE:
<221> NAME/KEY: misc_feature
<222> LOCATION: (244)..(244)
<223> OTHER INFORMATION: Xaa can be Ile, Thr, Ser, or Val
<220> FEATURE:
<221> NAME/KEY: misc_feature
<222> LOCATION: (303)..(303)
<223> OTHER INFORMATION: Xaa can be Asn, Asp, Gln, or Glu
<220> FEATURE:
<221> NAME/KEY: misc_feature
```

```
<222> LOCATION: (305)..(305)
<223> OTHER INFORMATION: Xaa can be Thr, Val, or Leu
<220> FEATURE:
<221> NAME/KEY: misc_feature
<222> LOCATION: (321)..(321)
<223> OTHER INFORMATION: Xaa can be Asn, Asp, Gln, or Glu
<220> FEATURE:
<221> NAME/KEY: misc_feature
<222> LOCATION: (323)..(323)
<223> OTHER INFORMATION: Xaa can be Lys, Arg, or His
<220> FEATURE:
<221> NAME/KEY: misc_feature
<222> LOCATION: (337)..(337)
<223> OTHER INFORMATION: Xaa can be Arg, Lys, or Cys
<220> FEATURE:
<221> NAME/KEY: misc_feature
<222> LOCATION: (338)..(338)
<223> OTHER INFORMATION: Xaa can be Gly, Ala, or Lys
<220> FEATURE:
<221> NAME/KEY: misc_feature
<222> LOCATION: (340)..(340)
<223> OTHER INFORMATION: Xaa can be Asn, Ala, Gln, or Glu
<220> FEATURE:
<221> NAME/KEY: misc_feature
<222> LOCATION: (343)..(343)
<223> OTHER INFORMATION: Xaa can be Leu, Asn, Thr, or Asp
<220> FEATURE:
<221> NAME/KEY: misc_feature
<222> LOCATION: (349)..(349)
<223> OTHER INFORMATION: Xaa can be Leu or Met
<220> FEATURE:
<221> NAME/KEY: misc_feature
<222> LOCATION: (354)..(354)
<223> OTHER INFORMATION: Xaa can be Glu, Gln, or Gly
<220> FEATURE:
<221> NAME/KEY: misc_feature
<222> LOCATION: (357)..(357)
<223> OTHER INFORMATION: Xaa can be Ala, Asn, or Pro
<220> FEATURE:
<221> NAME/KEY: misc_feature
<222> LOCATION: (360)..(360)
<223> OTHER INFORMATION: Xaa can be Ala, Ser, or Cys
<220> FEATURE:
<221> NAME/KEY: misc_feature
<222> LOCATION: (370)..(370)
<223> OTHER INFORMATION: Xaa can be Ile or Val
<220> FEATURE:
<221> NAME/KEY: misc_feature
<222> LOCATION: (375)..(375)
<223> OTHER INFORMATION: Xaa can be Ala, Asp, Lys, or Glu
<220> FEATURE:
<221> NAME/KEY: misc_feature
<222> LOCATION: (378)..(378)
<223> OTHER INFORMATION: Xaa can be Gln, Leu, Thr, or Met
<220> FEATURE:
<221> NAME/KEY: misc_feature
<222> LOCATION: (379)..(379)
<223> OTHER INFORMATION: Xaa can be Asn, Glu, or Ser
<220> FEATURE:
<221> NAME/KEY: misc_feature
<222> LOCATION: (391)..(391)
<223> OTHER INFORMATION: Xaa can be Asp, Thr, or Glu
<220> FEATURE:
<221> NAME/KEY: misc_feature
<222> LOCATION: (392)..(392)
<223> OTHER INFORMATION: Xaa can be Ala, His, or Asn
<220> FEATURE:
<221> NAME/KEY: misc_feature
<222> LOCATION: (402)..(402)
<223> OTHER INFORMATION: Xaa can be Ala, Cys, or Met
<220> FEATURE:
<221> NAME/KEY: misc_feature
<222> LOCATION: (403)..(403)
<223> OTHER INFORMATION: Xaa can be Leu or Met
<220> FEATURE:
<221> NAME/KEY: misc_feature
<222> LOCATION: (405)..(405)
<223> OTHER INFORMATION: Xaa can be Lys, Ile, or Gln
<220> FEATURE:
```

```
<221> NAME/KEY: misc_feature
<222> LOCATION: (416)..(416)
<223> OTHER INFORMATION: Xaa can be Ser, Ala, or Thr
<220> FEATURE:
<221> NAME/KEY: misc_feature
<222> LOCATION: (419)..(419)
<223> OTHER INFORMATION: Xaa can be Asn, Asp, Gln, or Glu
<220> FEATURE:
<221> NAME/KEY: misc_feature
<222> LOCATION: (439)..(439)
<223> OTHER INFORMATION: Xaa can be Ile or Val
<220> FEATURE:
<221> NAME/KEY: misc_feature
<222> LOCATION: (444)..(444)
<223> OTHER INFORMATION: Xaa can be Glu, Asp, Asn, or Val
<220> FEATURE:
<221> NAME/KEY: misc_feature
<222> LOCATION: (446)..(446)
<223> OTHER INFORMATION: Xaa can be Gly, Thr, Lys, or Ala
<220> FEATURE:
<221> NAME/KEY: misc_feature
<222> LOCATION: (447)..(447)
<223> OTHER INFORMATION: Xaa can be Asp, Glu, or Lys
<220> FEATURE:
<221> NAME/KEY: misc_feature
<222> LOCATION: (448)..(448)
<223> OTHER INFORMATION: Xaa, if present, can be Lys or Ala
<220> FEATURE:
<221> NAME/KEY: misc_feature
<222> LOCATION: (449)..(449)
<223> OTHER INFORMATION: Xaa, if present, can be Ala or Ser
<220> FEATURE:
<221> NAME/KEY: misc_feature
<222> LOCATION: (450)..(450)
<223> OTHER INFORMATION: Xaa, if present, can be Ala or Gly
<220> FEATURE:
<221> NAME/KEY: misc_feature
<222> LOCATION: (451)..(451)
<223> OTHER INFORMATION: Xaa, if present, is Lys
<220> FEATURE:
<221> NAME/KEY: misc_feature
<222> LOCATION: (452)..(452)
<223> OTHER INFORMATION: Xaa, if present, can be Val or Gly
<220> FEATURE:
<221> NAME/KEY: misc_feature
<222> LOCATION: (453)..(453)
<223> OTHER INFORMATION: Xaa, if present, can be Thr or Gly
<220> FEATURE:
<221> NAME/KEY: misc_feature
<222> LOCATION: (454)..(456)
<223> OTHER INFORMATION: Xaa, if present, can be Lys or Ala
<220> FEATURE:
<221> NAME/KEY: misc_feature
<222> LOCATION: (457)..(457)
<223> OTHER INFORMATION: Xaa, if present, can be Gln or Lys
<220> FEATURE:
<221> NAME/KEY: misc_feature
<222> LOCATION: (458)..(458)
<223> OTHER INFORMATION: Xaa, if present, is Lys
<220> FEATURE:
<221> NAME/KEY: misc_feature
<222> LOCATION: (459)..(459)
<223> OTHER INFORMATION: Xaa, if present, is Ala
<220> FEATURE:
<221> NAME/KEY: misc_feature
<222> LOCATION: (460)..(460)
<223> OTHER INFORMATION: Xaa, if present, is Ala
<220> FEATURE:
<221> NAME/KEY: misc_feature
<222> LOCATION: (461)..(461)
<223> OTHER INFORMATION: Xaa, if present, is Lys
<220> FEATURE:
<221> NAME/KEY: misc_feature
<222> LOCATION: (462)..(462)
<223> OTHER INFORMATION: Xaa, if present, is Lys

<400> SEQUENCE: 119

Met Gly Lys Gly Lys Xaa His Ile Asn Leu Val Val Ile Gly His Val
```

```
1               5                   10                  15
Asp Ala Gly Lys Ser Thr Thr Gly His Leu Ile Tyr Lys Cys Gly
                20                  25                  30

Gly Ile Asp Lys Arg Thr Ile Glu Lys Phe Glu Lys Glu Ala Ala Glu
            35                  40                  45

Leu Gly Lys Gly Ser Phe Lys Tyr Ala Trp Val Leu Asp Lys Xaa Lys
            50                  55                  60

Ala Glu Arg Glu Arg Gly Ile Thr Ile Asp Ile Ala Leu Trp Lys Phe
65                      70                  75                  80

Glu Thr Pro Lys Xaa Phe Phe Thr Xaa Ile Asp Ala Pro Gly His Arg
                85                  90                  95

Asp Phe Ile Lys Asn Met Ile Thr Gly Thr Ser Gln Ala Asp Val Ala
                100                 105                 110

Xaa Leu Xaa Xaa Ala Ser Gly Xaa Gly Glu Phe Glu Ala Gly Ile Ser
            115                 120                 125

Lys Xaa Gly Gln Thr Arg Glu His Ala Leu Leu Ala Phe Thr Leu Gly
        130                 135                 140

Xaa Lys Gln Met Xaa Val Ala Xaa Asn Lys Met Asp Asp Lys Ser Val
145                 150                 155                 160

Xaa Tyr Ser Xaa Ala Arg Xaa Xaa Glu Ile Lys Asn Glu Xaa Thr Xaa
                165                 170                 175

Xaa Leu Xaa Lys Val Gly Xaa Xaa Pro Xaa Xaa Xaa Xaa Xaa Pro Phe
            180                 185                 190

Xaa Pro Ile Ser Gly Trp Asn Gly Asp Asn Met Ile Xaa Xaa Ser Xaa
        195                 200                 205

Asn Met Pro Trp Tyr Lys Gly Xaa Xaa Xaa Xaa Xaa Xaa Xaa Xaa
            210                 215                 220

Xaa Xaa Xaa Pro Thr Leu Leu Glu Ala Leu Asp Asn Xaa Xaa Pro Pro
225                 230                 235                 240

Lys Arg Pro Xaa Asp Lys Pro Leu Arg Leu Pro Leu Gln Asp Val Tyr
            245                 250                 255

Lys Ile Gly Gly Ile Gly Thr Val Pro Val Gly Arg Val Glu Thr Gly
            260                 265                 270

Val Ile Lys Pro Gly Met Thr Val Thr Phe Ala Pro Val Gly Val Ser
        275                 280                 285

Thr Glu Val Lys Ser Val Glu Met His His Glu Ser Ile Pro Xaa Ala
        290                 295                 300

Xaa Pro Gly Asp Asn Val Gly Phe Asn Val Lys Asn Val Ser Val Lys
305                 310                 315                 320

Xaa Ile Xaa Arg Gly Asn Val Cys Gly Asp Ala Lys Asn Asp Pro Pro
            325                 330                 335

Xaa Xaa Thr Xaa Ser Phe Xaa Ala Gln Val Ile Val Xaa Asn His Pro
            340                 345                 350

Gly Xaa Ile Arg Xaa Gly Tyr Xaa Pro Val Ile Asp Cys His Thr Ala
        355                 360                 365

His Xaa Ala Cys Lys Phe Xaa Glu Ile Xaa Xaa Lys Met Asp Arg Arg
    370                 375                 380

Ser Gly Lys Val Leu Glu Xaa Xaa Pro Lys Phe Val Lys Ser Gly Asp
385                 390                 395                 400

Ser Xaa Xaa Val Xaa Leu Val Pro Ser Lys Pro Met Cys Val Glu Xaa
            405                 410                 415

Phe Ser Xaa Tyr Pro Pro Leu Gly Arg Phe Ala Val Arg Asp Met Arg
        420                 425                 430
```

```
Gln Thr Val Ala Val Gly Xaa Ile Lys Ser Val Xaa Lys Xaa Xaa Xaa
                435                 440                 445

Xaa Xaa Xaa Xaa Xaa Xaa Xaa Xaa Xaa Xaa Xaa Xaa
        450                 455                 460

<210> SEQ ID NO 120
<211> LENGTH: 339
<212> TYPE: PRT
<213> ORGANISM: Schizochytrium sp.

<400> SEQUENCE: 120

Met Ser Ala Asp Ala Pro Ile Met Gly Ile Asn Gly Phe Gly Arg Ile
1               5                   10                  15

Gly Arg Leu Val Phe Arg Thr Ala Phe Glu Thr Gly Asn Val Lys Val
            20                  25                  30

Val Ala Ile Asn Asp Leu Leu Asp Leu Asp Tyr Ile Ala Tyr Leu Leu
        35                  40                  45

Lys Tyr Asp Ser Val His Gly Pro Phe Lys Gly Thr Ile Glu Ile Lys
    50                  55                  60

Asp Gly Asn Leu Val Val Asn Gly Glu Thr Val Lys Val Tyr Ser Glu
65                  70                  75                  80

Arg Asp Pro Ser Asn Ile Pro Trp Gly Glu Asn Gly Val Glu Phe Val
                85                  90                  95

Cys Glu Ser Thr Gly Ile Phe Thr Thr Ala Glu Lys Cys Gln Ala His
            100                 105                 110

Leu Arg Gly Gly Ala Lys Arg Val Ile Ile Ser Ala Pro Pro Lys Asp
        115                 120                 125

Asp Thr Pro Met Phe Val Met Gly Val Asn Asn Glu Asp Tyr Asp Gly
    130                 135                 140

Glu Asp Ile Thr Ser Asn Ala Ser Cys Thr Thr Asn Cys Leu Ala Pro
145                 150                 155                 160

Leu Ala Lys Val Ile Asn Asp Asn Phe Gly Ile Val Glu Gly Leu Met
                165                 170                 175

Thr Thr Val His Ala Met Thr Ala Asn Gln Leu Thr Val Asp Gly Pro
            180                 185                 190

Ser Lys Gly Gly Lys Asp Trp Arg Ala Gly Arg Ser Ala Gly Ala Asn
        195                 200                 205

Val Ile Pro Ser Ser Thr Gly Ala Ala Lys Ala Val Gly Lys Val Ile
    210                 215                 220

Pro Ala Leu Asn Gly Lys Leu Thr Gly Met Ala Phe Arg Val Pro Thr
225                 230                 235                 240

Pro Asp Val Ser Val Val Asp Leu Thr Cys Lys Ile Glu Lys Pro Asn
                245                 250                 255

Ser Tyr Glu Glu Ile Lys Lys Val Leu Lys Ala Ala Ser Glu Asn Glu
            260                 265                 270

Leu Lys Gly Ile Leu Gly Tyr Thr Glu Asp Ala Val Val Ser Asn Asp
        275                 280                 285

Phe Val Gly Asn Thr Asn Ser Ser Ile Phe Asp Ala Asp Ala Gly Ile
    290                 295                 300

Met Leu Asn Asp Thr Phe Val Lys Leu Ile Ser Trp Tyr Asp Asn Glu
305                 310                 315                 320

Arg Gly Tyr Ser Thr Arg Leu Thr Asp Leu Ala Cys Tyr Ile Lys Ser
                325                 330                 335

Thr Gly Lys
```

<210> SEQ ID NO 121
<211> LENGTH: 334
<212> TYPE: PRT
<213> ORGANISM: Phaeodactylum tricornutum

<400> SEQUENCE: 121

Met Pro Val Ser Leu Gly Ile Asn Gly Phe Gly Arg Ile Gly Arg Leu
1               5                   10                  15

Val Met Arg Ala Ala Leu Glu His Pro Asp Ala Thr Val Val Ala Val
            20                  25                  30

Asn Asp Pro Phe Leu Thr Pro Glu Tyr Ala Ala Tyr Gln Phe Lys Tyr
        35                  40                  45

Asp Ser Val His Gly Thr Tyr Ser Glu Asp Val Ser Phe Glu Glu Gly
    50                  55                  60

Tyr Leu Val Val Gly Asp Lys Lys Ile Arg Phe Phe Ser Glu Arg Asn
65                  70                  75                  80

Pro Glu Glu Ile Gly Trp Gly Ser Val Gly Ala Glu Ile Val Cys Glu
                85                  90                  95

Ser Thr Gly Val Phe Thr Thr Ile Asp Lys Ala Gln Ala His Ile Asn
            100                 105                 110

Gly Gly Ala Glu Lys Val Val Ile Ser Ala Pro Ser Ala Asp Ala Pro
        115                 120                 125

Met Tyr Val Met Gly Val Asn His Thr Thr Tyr Ser Gly Ala Thr Val
    130                 135                 140

Phe Ser Asn Ala Ser Cys Thr Thr Asn Cys Leu Ala Pro Leu Ala Lys
145                 150                 155                 160

Val Leu His Glu Glu Phe Gly Ile Val Glu Gly Leu Met Thr Thr Ile
                165                 170                 175

His Ala Gly Thr Ala Thr Gln Leu Val Val Asp Gly Pro Ala Lys Arg
            180                 185                 190

Gly Lys Asp Trp Arg Ala Gly Arg Ser Ser Leu Ala Asn Leu Ile Pro
        195                 200                 205

Ala Ser Thr Gly Ala Ala Lys Ala Val Gly Lys Val Ile Pro Glu Leu
    210                 215                 220

Asn Gly Lys Leu Thr Gly Met Ala Val Arg Val Pro Thr Ala Asp Val
225                 230                 235                 240

Ser Met Val Asp Leu Thr Ile Arg Thr Glu Lys Ala Val Ser Ala Ala
                245                 250                 255

Glu Leu Lys Ala Ala Leu Lys Lys Ala Ser Glu Gly Pro Met Lys Gly
            260                 265                 270

Ile Leu Gly Tyr Thr Glu Asp Ala Val Val Ser Gln Asp Phe Val His
        275                 280                 285

Asp Pro Arg Ser Ser Ile Val Asp Ala Ser Ala Gly Ile Ala Leu Asn
    290                 295                 300

Asp Asn Phe His Lys Val Ile Ala Trp Tyr Asp Asn Glu Trp Gly Tyr
305                 310                 315                 320

Ser Asn Arg Leu Val Asp Leu Ala Ile Tyr Thr Ser Gly Lys
                325                 330

<210> SEQ ID NO 122
<211> LENGTH: 318
<212> TYPE: PRT
<213> ORGANISM: Phytophthora palmivora

<400> SEQUENCE: 122

```
Ser Lys Val Gly Ile Asn Gly Phe Gly Arg Ile Gly Arg Leu Val Leu
1               5                   10                  15

Arg Ala Ala Lys Asn Pro Glu Ile Asn Val Val Ala Val Asn Gly
            20                  25                  30

Pro Phe Ile Ala Thr Lys Tyr Met Glu Tyr Met Leu Lys Tyr Asp Thr
            35                  40                  45

Val His Gly Arg Phe Gly Gly Glu Leu Ser His Asp Glu Gln Asn Ile
50                  55                  60

Tyr Val Asp Gly Lys Ala Ile Arg Val Phe Asn Glu Met Asn Pro Ala
65                  70                  75                  80

Asn Ile Lys Trp Gly Glu Glu Gln Val Gln Tyr Val Val Glu Ser Thr
                85                  90                  95

Gly Ala Phe Thr Thr Thr Glu Lys Ala Ser Ala His Leu Lys Asn Gly
            100                 105                 110

Val Glu Lys Val Val Ile Ser Ala Pro Ser Ser Asp Ala Pro Met Phe
            115                 120                 125

Val Met Gly Val Asn His Glu Leu Tyr Glu Lys Asn Met His Val Val
130                 135                 140

Ser Asn Ala Ser Cys Thr Thr Asn Cys Leu Ala Pro Leu Ala Lys Val
145                 150                 155                 160

Val Asn Asp Lys Phe Gly Ile Lys Glu Gly Leu Met Thr Thr Val His
                165                 170                 175

Ala Val Thr Ala Thr Gln Lys Thr Val Asp Gly Pro Ser Lys Lys Asp
            180                 185                 190

Trp Arg Gly Gly Arg Gly Ala Cys Phe Asn Ile Ile Pro Ser Ser Thr
            195                 200                 205

Gly Ala Ala Lys Ala Val Gly Lys Val Ile Pro Ser Leu Asn Gly Lys
210                 215                 220

Leu Thr Gly Met Ser Phe Arg Val Pro Thr Ala Asp Val Ser Val Val
225                 230                 235                 240

Asp Leu Thr Ala Arg Leu Val Asn Pro Ala Ser Tyr Glu Glu Ile Lys
                245                 250                 255

Ala Ala Ile Lys Ser Ala Ser Glu Asn Glu Met Lys Gly Ile Leu Gly
            260                 265                 270

Tyr Thr Glu Glu Ala Val Val Ser Ser Asp Phe Ile Gly Asp Ser His
            275                 280                 285

Ser Ser Ile Phe Asp Ala Glu Ala Gly Ile Ala Leu Thr Asp Asp Phe
290                 295                 300

Val Lys Leu Val Ser Trp Tyr Asp Asn Glu Trp Gly Tyr Ser
305                 310                 315

<210> SEQ ID NO 123
<211> LENGTH: 332
<212> TYPE: PRT
<213> ORGANISM: Saccharomyces cerevisiae

<400> SEQUENCE: 123

Met Val Arg Val Ala Ile Asn Gly Phe Gly Arg Ile Gly Arg Leu Val
1               5                   10                  15

Met Arg Ile Ala Leu Ser Arg Pro Asn Val Glu Val Val Ala Leu Asn
            20                  25                  30

Asp Pro Phe Ile Thr Asn Asp Tyr Ala Ala Tyr Met Phe Lys Tyr Asp
            35                  40                  45

Ser Thr His Gly Arg Tyr Ala Gly Glu Val Ser His Asp Asp Lys His
```

```
                50                  55                  60
Ile Ile Val Asp Gly Lys Lys Ile Ala Thr Tyr Gln Glu Arg Asp Pro
 65                  70                  75                  80

Ala Asn Leu Pro Trp Gly Ser Ser Asn Val Asp Ile Ala Ile Asp Ser
                 85                  90                  95

Thr Gly Val Phe Lys Glu Leu Asp Thr Ala Gln Lys His Ile Asp Ala
            100                 105                 110

Gly Ala Lys Lys Val Val Ile Thr Ala Pro Ser Ser Thr Ala Pro Met
        115                 120                 125

Phe Val Met Gly Val Asn Glu Val Lys Tyr Thr Ser Asp Leu Lys Ile
    130                 135                 140

Val Ser Asn Ala Ser Cys Thr Thr Asn Cys Leu Ala Pro Leu Ala Lys
145                 150                 155                 160

Val Ile Asn Asp Ala Phe Gly Ile Glu Glu Gly Leu Met Thr Thr Val
                165                 170                 175

His Ser Leu Thr Ala Thr Gln Lys Thr Val Asp Gly Pro Ser His Lys
            180                 185                 190

Asp Trp Arg Gly Gly Arg Thr Ala Ser Gly Asn Ile Ile Pro Ser Ser
        195                 200                 205

Thr Gly Ala Ala Lys Ala Val Gly Lys Val Leu Pro Glu Leu Gln Gly
    210                 215                 220

Lys Leu Thr Gly Met Ala Phe Arg Val Pro Thr Val Asp Val Ser Val
225                 230                 235                 240

Val Asp Leu Thr Val Lys Leu Asp Lys Glu Thr Thr Tyr Asp Glu Ile
                245                 250                 255

Lys Lys Val Val Lys Ala Ala Glu Gly Lys Leu Lys Gly Val Leu
            260                 265                 270

Gly Tyr Thr Glu Asp Ala Val Val Ser Ser Asp Phe Leu Gly Asp Ser
        275                 280                 285

His Ser Ser Ile Phe Asp Ala Ser Ala Gly Ile Gln Leu Ser Pro Lys
    290                 295                 300

Phe Val Lys Leu Val Ser Trp Tyr Asp Asn Glu Tyr Gly Tyr Ser Thr
305                 310                 315                 320

Arg Val Val Asp Leu Val Glu His Ile Ala Lys Ala
                325                 330

<210> SEQ ID NO 124
<211> LENGTH: 341
<212> TYPE: PRT
<213> ORGANISM: Artificial Sequence
<220> FEATURE:
<223> OTHER INFORMATION: Consensus sequence derived from various
      organisms
<220> FEATURE:
<221> NAME/KEY: misc_feature
<222> LOCATION: (1)..(1)
<223> OTHER INFORMATION: Xaa, if present, is Met
<220> FEATURE:
<221> NAME/KEY: misc_feature
<222> LOCATION: (2)..(2)
<223> OTHER INFORMATION: Xaa, if present, is Ser
<220> FEATURE:
<221> NAME/KEY: misc_feature
<222> LOCATION: (3)..(3)
<223> OTHER INFORMATION: Xaa, if present, is Ala
<220> FEATURE:
<221> NAME/KEY: misc_feature
<222> LOCATION: (4)..(4)
<223> OTHER INFORMATION: Xaa, if present, is Asp or Met
<220> FEATURE:
<221> NAME/KEY: misc_feature
```

-continued

```
<222> LOCATION: (5)..(5)
<223> OTHER INFORMATION: Xaa, if present, can be Ala, Pro, or Met
<220> FEATURE:
<221> NAME/KEY: misc_feature
<222> LOCATION: (7)..(7)
<223> OTHER INFORMATION: Xaa, if present, can be Ile, Ser, Lys, or Arg
<220> FEATURE:
<221> NAME/KEY: misc_feature
<222> LOCATION: (8)..(8)
<223> OTHER INFORMATION: Xaa, if present, can be Met, Leu, or Val
<220> FEATURE:
<221> NAME/KEY: misc_feature
<222> LOCATION: (27)..(27)
<223> OTHER INFORMATION: Xaa can be Thr, His, Asn, or Arg
<220> FEATURE:
<221> NAME/KEY: misc_feature
<222> LOCATION: (29)..(29)
<223> OTHER INFORMATION: Xaa can be Asn, Asp, Gln, or Glu
<220> FEATURE:
<221> NAME/KEY: misc_feature
<222> LOCATION: (31)..(31)
<223> OTHER INFORMATION: Xaa can be Lys, Thr, Asn, or Glu
<220> FEATURE:
<221> NAME/KEY: misc_feature
<222> LOCATION: (42)..(42)
<223> OTHER INFORMATION: Xaa can be Leu, Pro, Thr, or Asn
<220> FEATURE:
<221> NAME/KEY: misc_feature
<222> LOCATION: (48)..(48)
<223> OTHER INFORMATION: Xaa can be Leu, Gln, or Met
<220> FEATURE:
<221> NAME/KEY: misc_feature
<222> LOCATION: (57)..(57)
<223> OTHER INFORMATION: Xaa can be Pro, Thr, or Arg
<220> FEATURE:
<221> NAME/KEY: misc_feature
<222> LOCATION: (58)..(58)
<223> OTHER INFORMATION: Xaa can be Phe or Tyr
<220> FEATURE:
<221> NAME/KEY: misc_feature
<222> LOCATION: (59)..(59)
<223> OTHER INFORMATION: Xaa can be Lys, Ser, Gly, or Ala
<220> FEATURE:
<221> NAME/KEY: misc_feature
<222> LOCATION: (61)..(61)
<223> OTHER INFORMATION: Xaa can be Thr, Asp, or Glu
<220> FEATURE:
<221> NAME/KEY: misc_feature
<222> LOCATION: (64)..(64)
<223> OTHER INFORMATION: Xaa can be Ile, Phe, or His
<220> FEATURE:
<221> NAME/KEY: misc_feature
<222> LOCATION: (65)..(65)
<223> OTHER INFORMATION: Xaa can be Lys, Glu, or Asp
<220> FEATURE:
<221> NAME/KEY: misc_feature
<222> LOCATION: (66)..(66)
<223> OTHER INFORMATION: Xaa can be Asn, Asp, Gln, or Glu
<220> FEATURE:
<221> NAME/KEY: misc_feature
<222> LOCATION: (72)..(72)
<223> OTHER INFORMATION: Xaa can be Asn, Gly, or Asp
<220> FEATURE:
<221> NAME/KEY: misc_feature
<222> LOCATION: (76)..(76)
<223> OTHER INFORMATION: Xaa can be Ile or Val
<220> FEATURE:
<221> NAME/KEY: misc_feature
<222> LOCATION: (79)..(79)
<223> OTHER INFORMATION: Xaa can be Phe or Tyr
<220> FEATURE:
<221> NAME/KEY: misc_feature
<222> LOCATION: (83)..(83)
<223> OTHER INFORMATION: Xaa can be Asn, Asp, Gln, or Glu
<220> FEATURE:
<221> NAME/KEY: misc_feature
<222> LOCATION: (85)..(85)
<223> OTHER INFORMATION: Xaa can be Ser, Glu, or Ala
<220> FEATURE:
```

```
<221> NAME/KEY: misc_feature
<222> LOCATION: (86)..(86)
<223> OTHER INFORMATION: Xaa can be Asn or Glu
<220> FEATURE:
<221> NAME/KEY: misc_feature
<222> LOCATION: (92)..(92)
<223> OTHER INFORMATION: Xaa can be Asn, Val, Glu, or Ser
<220> FEATURE:
<221> NAME/KEY: misc_feature
<222> LOCATION: (95)..(95)
<223> OTHER INFORMATION: Xaa can be Glu, Gln, or Asp
<220> FEATURE:
<221> NAME/KEY: misc_feature
<222> LOCATION: (99)..(99)
<223> OTHER INFORMATION: Xaa can be Asn, Asp, Gln, or Glu
<220> FEATURE:
<221> NAME/KEY: misc_feature
<222> LOCATION: (107)..(107)
<223> OTHER INFORMATION: Xaa can be Ala, Ile, Thr, or Leu
<220> FEATURE:
<221> NAME/KEY: misc_feature
<222> LOCATION: (108)..(108)
<223> OTHER INFORMATION: Xaa can be Asn, Asp, Gln, or Glu
<220> FEATURE:
<221> NAME/KEY: misc_feature
<222> LOCATION: (115)..(115)
<223> OTHER INFORMATION: Xaa can be Arg, Asn, Lys, or Asp
<220> FEATURE:
<221> NAME/KEY: misc_feature
<222> LOCATION: (122)..(122)
<223> OTHER INFORMATION: Xaa can be Ile or Val
<220> FEATURE:
<221> NAME/KEY: misc_feature
<222> LOCATION: (128)..(128)
<223> OTHER INFORMATION: Xaa can be Lys, Ala, or Ser
<220> FEATURE:
<221> NAME/KEY: misc_feature
<222> LOCATION: (130)..(130)
<223> OTHER INFORMATION: Xaa, if present, is Asp
<220> FEATURE:
<221> NAME/KEY: misc_feature
<222> LOCATION: (134)..(134)
<223> OTHER INFORMATION: Xaa can be Phe or Tyr
<220> FEATURE:
<221> NAME/KEY: misc_feature
<222> LOCATION: (142)..(142)
<223> OTHER INFORMATION: Xaa can be Asp, Thr, Leu, or Lys
<220> FEATURE:
<221> NAME/KEY: misc_feature
<222> LOCATION: (144)..(144)
<223> OTHER INFORMATION: Xaa can be Asp, Ser, Glu, or Thr
<220> FEATURE:
<221> NAME/KEY: misc_feature
<222> LOCATION: (146)..(146)
<223> OTHER INFORMATION: Xaa can be Glu, Ala, Asn, or Asp
<220> FEATURE:
<221> NAME/KEY: misc_feature
<222> LOCATION: (147)..(147)
<223> OTHER INFORMATION: Xaa, if present, is Met or Leu
<220> FEATURE:
<221> NAME/KEY: misc_feature
<222> LOCATION: (148)..(148)
<223> OTHER INFORMATION: Xaa can be Asp, Thr, His, or Lys
<220> FEATURE:
<221> NAME/KEY: misc_feature
<222> LOCATION: (149)..(149)
<223> OTHER INFORMATION: Xaa can be Ile or Val
<220> FEATURE:
<221> NAME/KEY: misc_feature
<222> LOCATION: (150)..(150)
<223> OTHER INFORMATION: Xaa can be Thr, Phe, or Val
<220> FEATURE:
<221> NAME/KEY: misc_feature
<222> LOCATION: (169)..(169)
<223> OTHER INFORMATION: Xaa can be Asn, Asp, Gln, or Glu
<220> FEATURE:
<221> NAME/KEY: misc_feature
<222> LOCATION: (170)..(170)
<223> OTHER INFORMATION: Xaa can be Asn, Glu, Lys or Ala
```

```
<220> FEATURE:
<221> NAME/KEY: misc_feature
<222> LOCATION: (181)..(181)
<223> OTHER INFORMATION: Xaa can be Ile or Val
<220> FEATURE:
<221> NAME/KEY: misc_feature
<222> LOCATION: (184)..(184)
<223> OTHER INFORMATION: Xaa can be Met, Gly, Val, or Leu
<220> FEATURE:
<221> NAME/KEY: misc_feature
<222> LOCATION: (197)..(197)
<223> OTHER INFORMATION: Xaa, if present, is Gly or Arg
<220> FEATURE:
<221> NAME/KEY: misc_feature
<222> LOCATION: (208)..(208)
<223> OTHER INFORMATION: Xaa can be Gly, Leu, Cys or Ser
<220> FEATURE:
<221> NAME/KEY: misc_feature
<222> LOCATION: (211)..(211)
<223> OTHER INFORMATION: Xaa can be Val, Leu, or Ile
<220> FEATURE:
<221> NAME/KEY: misc_feature
<222> LOCATION: (230)..(230)
<223> OTHER INFORMATION: Xaa can be Asn, Asp, Gln, or Glu
<220> FEATURE:
<221> NAME/KEY: misc_feature
<222> LOCATION: (252)..(252)
<223> OTHER INFORMATION: Xaa can be Cys, Ile, Ala, or Val
<220> FEATURE:
<221> NAME/KEY: misc_feature
<222> LOCATION: (254)..(254)
<223> OTHER INFORMATION: Xaa can be Ile, Thr, or Leu
<220> FEATURE:
<221> NAME/KEY: misc_feature
<222> LOCATION: (258)..(258)
<223> OTHER INFORMATION: Xaa can be Asn, Val, Ala, or Thr
<220> FEATURE:
<221> NAME/KEY: misc_feature
<222> LOCATION: (275)..(275)
<223> OTHER INFORMATION: Xaa can be Leu or Met
<220> FEATURE:
<221> NAME/KEY: misc_feature
<222> LOCATION: (278)..(278)
<223> OTHER INFORMATION: Xaa can be Ile or Val
<220> FEATURE:
<221> NAME/KEY: misc_feature
<222> LOCATION: (284)..(284)
<223> OTHER INFORMATION: Xaa can be Asn, Asp, Gln, or Glu
<220> FEATURE:
<221> NAME/KEY: misc_feature
<222> LOCATION: (289)..(289)
<223> OTHER INFORMATION: Xaa can be Asn, Gln, or Ser
<220> FEATURE:
<221> NAME/KEY: misc_feature
<222> LOCATION: (294)..(294)
<223> OTHER INFORMATION: Xaa can be Asn, Asp, Gln, or Glu
<220> FEATURE:
<221> NAME/KEY: misc_feature
<222> LOCATION: (295)..(295)
<223> OTHER INFORMATION: Xaa can be Thr, Pro, or Ser
<220> FEATURE:
<221> NAME/KEY: misc_feature
<222> LOCATION: (296)..(296)
<223> OTHER INFORMATION: Xaa can be Asn, Arg, or His
<220> FEATURE:
<221> NAME/KEY: misc_feature
<222> LOCATION: (311)..(311)
<223> OTHER INFORMATION: Xaa can be Thr, Asn, Asp, or Lys
<220> FEATURE:
<221> NAME/KEY: misc_feature
<222> LOCATION: (316)..(316)
<223> OTHER INFORMATION: Xaa can be Ile or Val
<220> FEATURE:
<221> NAME/KEY: misc_feature
<222> LOCATION: (334)..(334)
<223> OTHER INFORMATION: Xaa can be Cys, Ile, or Glu
<220> FEATURE:
<221> NAME/KEY: misc_feature
<222> LOCATION: (337)..(337)
```

```
<223> OTHER INFORMATION: Xaa can be Lys, Ser, or Ala
<220> FEATURE:
<221> NAME/KEY: misc_feature
<222> LOCATION: (338)..(338)
<223> OTHER INFORMATION: Xaa can be Ser, Gly, or Lys
<220> FEATURE:
<221> NAME/KEY: misc_feature
<222> LOCATION: (339)..(339)
<223> OTHER INFORMATION: Xaa can be Thr, Lys, or Ala
<220> FEATURE:
<221> NAME/KEY: misc_feature
<222> LOCATION: (340)..(340)
<223> OTHER INFORMATION: Xaa, if present, is Gly
<220> FEATURE:
<221> NAME/KEY: misc_feature
<222> LOCATION: (341)..(341)
<223> OTHER INFORMATION: Xaa, if present, is Lys

<400> SEQUENCE: 124

Xaa Xaa Xaa Xaa Xaa Val Xaa Xaa Gly Ile Asn Gly Phe Gly Arg Ile
1               5                   10                  15

Gly Arg Leu Val Met Arg Ala Ala Leu Glu Xaa Pro Xaa Val Xaa Val
            20                  25                  30

Val Ala Val Asn Asp Pro Phe Leu Thr Xaa Asp Tyr Ala Ala Tyr Xaa
        35                  40                  45

Leu Lys Tyr Asp Ser Val His Gly Xaa Xaa Xaa Gly Xaa Val Ser Xaa
    50                  55                  60

Xaa Xaa Gly Asn Leu Val Val Xaa Gly Lys Lys Xaa Arg Val Xaa Ser
65                  70                  75                  80

Glu Arg Xaa Pro Xaa Xaa Ile Pro Trp Gly Glu Xaa Gly Val Xaa Ile
                85                  90                  95

Val Cys Xaa Ser Thr Gly Val Phe Thr Thr Xaa Xaa Lys Ala Gln Ala
            100                 105                 110

His Ile Xaa Gly Gly Ala Glu Lys Val Xaa Ile Ser Ala Pro Ser Xaa
        115                 120                 125

Asp Xaa Ala Pro Met Xaa Val Met Gly Val Asn His Glu Xaa Tyr Xaa
    130                 135                 140

Gly Xaa Xaa Xaa Xaa Xaa Ser Asn Ala Ser Cys Thr Thr Asn Cys Leu
145                 150                 155                 160

Ala Pro Leu Ala Lys Val Ile Asn Xaa Xaa Phe Gly Ile Val Glu Gly
                165                 170                 175

Leu Met Thr Thr Xaa His Ala Xaa Thr Ala Thr Gln Leu Thr Val Asp
            180                 185                 190

Gly Pro Ser Lys Xaa Gly Lys Asp Trp Arg Ala Gly Arg Ser Ala Xaa
        195                 200                 205

Ala Asn Xaa Ile Pro Ser Ser Thr Gly Ala Ala Lys Ala Val Gly Lys
    210                 215                 220

Val Ile Pro Glu Leu Xaa Gly Lys Leu Thr Gly Met Ala Phe Arg Val
225                 230                 235                 240

Pro Thr Ala Asp Val Ser Val Val Asp Leu Thr Xaa Arg Xaa Glu Lys
            245                 250                 255

Pro Xaa Ser Tyr Glu Glu Ile Lys Ala Ala Leu Lys Ala Ala Ser Glu
        260                 265                 270

Asn Glu Xaa Lys Gly Xaa Leu Gly Tyr Thr Glu Xaa Ala Val Val Ser
    275                 280                 285

Xaa Asp Phe Val Gly Xaa Xaa Ser Ser Ile Phe Asp Ala Ser Ala
290                 295                 300

Gly Ile Ala Leu Asn Asp Xaa Phe Val Lys Leu Xaa Ser Trp Tyr Asp
305                 310                 315                 320
```

```
Asn Glu Trp Gly Tyr Ser Thr Arg Leu Val Asp Leu Ala Xaa Tyr Ile
            325                 330                 335

Xaa Xaa Xaa Xaa Xaa
        340

<210> SEQ ID NO 125
<211> LENGTH: 500
<212> TYPE: DNA
<213> ORGANISM: Artificial Sequence
<220> FEATURE:
<223> OTHER INFORMATION: Chemically synthesized actin promoter (KpnI)

<400> SEQUENCE: 125
cactcacatt ggtagtctgt agacatgatt tggaccttct gtaggcagag agtacctact    60
aggagcgtct tccaataatc gcctcgattt ccccaacctg gatgatgctg gtggctcaac   120
ttgaactaaa acctgaggat gaaggagcca ctcgattcca cgcacaccct tcaggtggtc   180
atttgcaggt tagcgataga ggtatctctc acaaacactg taaatagttt tgtgagtaaa   240
tacacacacg agcactccta taaagggtgt gtaagctaag gaaaatcccc tcgcaacaca   300
ctgagtatca aaagaggaac ctacgactaa gaaggttatc ataaatggat gtaatcagag   360
gaggtaacac tgtaaattta tggagacagt ggagggtctt tgggcacgaa gatctgcaag   420
cgcgccatca gcagatccgc aaccttcgag ctcaagaagc aactcaacag tagaagaaca   480
agcacccaac tagcaaaatg                                               500

<210> SEQ ID NO 126
<211> LENGTH: 500
<212> TYPE: DNA
<213> ORGANISM: Artificial Sequence
<220> FEATURE:
<223> OTHER INFORMATION: Chemically synthesized actin promoter (EcoRI)
<220> FEATURE:
<221> NAME/KEY: misc_feature
<222> LOCATION: (277)..(277)
<223> OTHER INFORMATION: n is a, c, g, or t

<400> SEQUENCE: 126
taattcatgt atggtaggta tgtagatagg taggtgggaa gtagtctgga tgttttatca    60
ttaaaggttg gactagacgc acatgttttt atttaaagga cacaactgga agtcagtcaa   120
tcttagctgg ggttctcacc ttttcaaat tgattgcccc ttgcaactag ctatctagct    180
atagctggct agtagatttt tggaagtcgg gtattgaagg tatgcgcaca cgtgcaaatc   240
cctcctacaa tcactgcctc ctaaacccett ccctcancaa gacctccaga tattactcca   300
aagtgaacaa agtattggt gcaccctcac aataatacaa acgctaaa atgtgctaga     360 gggcccccac tgagaaaggt aagtgataga ggagtgtctt cgggcacgaa gatctgcaag   420
cgcgccatca gcagaaccgc aaccttcgag cccaagaagc aactcaacag tagcagaaca   480
agctcccaac tagcaaaatg                                               500

<210> SEQ ID NO 127
<211> LENGTH: 512
<212> TYPE: DNA
<213> ORGANISM: Artificial Sequence
<220> FEATURE:
<223> OTHER INFORMATION: Chemically synthesized consensus sequences
<220> FEATURE:
<221> NAME/KEY: misc_feature
<222> LOCATION: (11)..(11)
<223> OTHER INFORMATION: n, if present, is a
<220> FEATURE:
```

```
<221> NAME/KEY: misc_feature
<222> LOCATION: (18)..(18)
<223> OTHER INFORMATION: n, if present, is g
<220> FEATURE:
<221> NAME/KEY: misc_feature
<222> LOCATION: (31)..(31)
<223> OTHER INFORMATION: n, if present, is a
<220> FEATURE:
<221> NAME/KEY: misc_feature
<222> LOCATION: (32)..(32)
<223> OTHER INFORMATION: n, if present, is t
<220> FEATURE:
<221> NAME/KEY: misc_feature
<222> LOCATION: (33)..(33)
<223> OTHER INFORMATION: n, if present, is t
<220> FEATURE:
<221> NAME/KEY: misc_feature
<222> LOCATION: (101)..(101)
<223> OTHER INFORMATION: n, if present, is c
<220> FEATURE:
<221> NAME/KEY: misc_feature
<222> LOCATION: (102)..(102)
<223> OTHER INFORMATION: n, if present, is t
<220> FEATURE:
<221> NAME/KEY: misc_feature
<222> LOCATION: (118)..(118)
<223> OTHER INFORMATION: n, if present, is c
<220> FEATURE:
<221> NAME/KEY: misc_feature
<222> LOCATION: (123)..(123)
<223> OTHER INFORMATION: n, if present, is c
<220> FEATURE:
<221> NAME/KEY: misc_feature
<222> LOCATION: (134)..(134)
<223> OTHER INFORMATION: n, if present, is a
<220> FEATURE:
<221> NAME/KEY: misc_feature
<222> LOCATION: (135)..(135)
<223> OTHER INFORMATION: n, if present, is c
<220> FEATURE:
<221> NAME/KEY: misc_feature
<222> LOCATION: (148)..(149)
<223> OTHER INFORMATION: n, if present, is c
<220> FEATURE:
<221> NAME/KEY: misc_feature
<222> LOCATION: (150)..(151)
<223> OTHER INFORMATION: n, if present, is t
<220> FEATURE:
<221> NAME/KEY: misc_feature
<222> LOCATION: (165)..(165)
<223> OTHER INFORMATION: n, if present, is g
<220> FEATURE:
<221> NAME/KEY: misc_feature
<222> LOCATION: (202)..(202)
<223> OTHER INFORMATION: n, if present, is t
<220> FEATURE:
<221> NAME/KEY: misc_feature
<222> LOCATION: (246)..(246)
<223> OTHER INFORMATION: n, if present, is t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (299)..(299)
<223> OTHER INFORMATION: n, if present, is g
<220> FEATURE:
<221> NAME/KEY: misc_feature
<222> LOCATION: (300)..(300)
<223> OTHER INFORMATION: n, if present, is a
<220> FEATURE:
<221> NAME/KEY: misc_feature
<222> LOCATION: (301)..(301)
<223> OTHER INFORMATION: n, if present, is t
<220> FEATURE:
<221> NAME/KEY: misc_feature
<222> LOCATION: (368)..(368)
<223> OTHER INFORMATION: n, if present, is c
```

```
<220> FEATURE:
<221> NAME/KEY: misc_feature
<222> LOCATION: (374)..(374)
<223> OTHER INFORMATION: n, if present, is a

<400> SEQUENCE: 127
tmaytcayrt ntggtagntm tgtagayakg nnntrgrysk kmwgtagkcw grrwgtwyyw      60
wcwwkrarsg tykkmcwaka mkcmcmtskw tttmyyyaam nnggayrmwr ctggwrgntc    120
arntyrawct warnnctgrg gwtswmrnnn nkwkcmamty gattnccmck yrcamcywkc    180
wrkykrkcww twgcwggyta gnmgatwkwk gkawstcksr yawwsamkgt awryrswywy    240
gtgmrnaawy mcwcmyacra kcactscywy mwarrsystk ymmkcwnmrr rammtccmnn    300
nmtyrcwmca mastgaryaw marwakwggw rcmymckmmy aakaakrywa wcayrmwwrr    360
atgtrmtnag aggngsymmc actgwraawk kwwrgwgaya gwggagkgtc ttygggcacg    420
aagatctgca agcgcgccat cagcagawcc gcaaccttcg agcycaagaa gcaactcaac    480
agtagmagaa caagcwccca actagcaaaa tg                                 512
```